US009491935B2

(12) United States Patent
Kohtz

(10) Patent No.: US 9,491,935 B2
(45) Date of Patent: *Nov. 15, 2016

(54) ANIMAL MODELS OF NEUROLOGICAL DISORDERS

(71) Applicant: Ann & Robert H. Lurie Children's Hospital of Chicago, Chicago, IL (US)

(72) Inventor: Jhumku Kohtz, Chicago, IL (US)

(73) Assignee: Ann & Robert H. Lurie Children's Hospital of Chicago, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/532,860

(22) Filed: Nov. 4, 2014

(65) Prior Publication Data

US 2015/0296756 A1    Oct. 22, 2015

Related U.S. Application Data

(62) Division of application No. 13/383,539, filed as application No. PCT/US2010/042373 on Jul. 17, 2010, now Pat. No. 8,884,095.

(60) Provisional application No. 61/226,394, filed on Jul. 17, 2009.

(51) Int. Cl.

| A61K 49/00 | (2006.01) |
|---|---|
| A01K 67/00 | (2006.01) |
| C12N 15/85 | (2006.01) |
| A01K 67/027 | (2006.01) |
| C12N 15/113 | (2010.01) |

(52) U.S. Cl.
CPC ......... *A01K 67/0276* (2013.01); *C12N 15/113* (2013.01); *C12N 15/8509* (2013.01); *A01K 2217/054* (2013.01); *A01K 2217/056* (2013.01); *A01K 2227/105* (2013.01); *A01K 2267/0356* (2013.01); *C12N 2310/17* (2013.01); *C12N 2830/36* (2013.01)

(58) Field of Classification Search
None
See application file for complete search history.

(56) References Cited

U.S. PATENT DOCUMENTS

| 6,028,245 A | 2/2000 | Wasylyk et al. |
| 6,455,757 B1 | 9/2002 | Mucke et al. |

OTHER PUBLICATIONS

Costa FF, Gene 2007, 386(1-2)1-10.*
Kohtz, Jhumku D. et al.; "Regulatory long non-coding RNAs and neuronal disorders"; Physiology & Behavior, vol. 100, No. 3; pp. 250-254; XP027027547; Jun. 1, 2010.
Mehler, Mark F. et al.; "Noncoding RNAs and RNA Editing in Brain Development, Functional Diversification, and Neurological Disease"; Physiological Reviews, vol. 87, No. 3; pp. 799-823; XP055187443; Jul. 1, 2007.
Qureshi, Irfan A. et al.; "Long non-coding RNAs in nervous system function and disease"; Brain Research, vol. 1338; Jun. 1, 2010; XP055187442; Jun. 1, 2010.
Acampora, D., Merlo, G., Paleari, L., Zerega, B., Mantero, S., Barbieri, 0., Postiglione, M.P., Simeone, A., Levi, G., 1999. Craniofacial, vestibular and bone defects in mice lacking the Distal-less-related gene Dlx5; Development 126, 3795-3809.
Amrein H and Axel R (Feb. 21, 1997) Genes expressed in neurons of adult male *Drosophila*. Cell, 88:459-469.
Anderson SA, Eisenstat DD, Shi L, Rubenstein JL. Related Articles, Links (Oct. 17, 1997) Interneuron migration from basal forebrain to neocortex: dependence on Dlx genes. Science 278:474-6.
Anderson SA, Qui, M., Bulfone, A., Eisenstat, D., Meneses, J., Pedersen, R., Rubenstein, J.L. (Jul. 1997) Mutations of the homeobox genes Dlx-I and Dlx-2 disrupt the striatal subventricular zone and differentiation of late born striatal neurons. Neuron 19, 27-37.
Arney, K.L.; "*H19* and *Igf2*—enhancing the confusion?"; Trends in Genetics, vol. 19, No. 1; Jan. 2003; pp. 17-23.
Bejerano G., Pheasant M., Makunin L, Stephen S., Kent W.J., Mattick J.5., Haussler D.; May 28, 2004. Ultraconserved elements in the human genome. Science 304: 1321-1325.
Bienvenu, T. & Chelly, J. Molecular genetics ofRett syndrome: when DNA methylation goes unrecognized. Nat. Rev. Genet. 7, 415-426 (Jun. 2006).
Bierut LJ, Madden PA, Breslau N, Johnson EO, Hatsukami D, Pomerleau OF, Swan GE, Rutter J, Bertelsen S, Fox L, Fugman D, Goate AM, Hinrichs AL, Konvicka K, Martin NG, Montgomery GW, Saccone NL, Saccone SF, Wang JC, Chase GA, Rice JP, Ballinger DGNovel genes identified in a high-density genome wide association study for nicotine dependence. Hum Mol Genet. Jan. 1, 2007 ;16(I):24-35. Epub Dec. 7, 2006.
Blatt et al.; Density and Distribution of Hippocampal Neurotransmitter Receptors in Autism: An Autoradiographic Study; Journal of Autism and Developmental Disorders; vol. 31, No. 6; Dec. 2001; pp. 537-543.
Boffelli D., Nobrega MA, Rubin E.M. Jun. 2004. Comparative genomics at the vertebrate extremes. Nat. Rev. Genet. 5: 456-465.
Bond, Allison M. et al.; "Balanced gene regulation by an embryonic brain ncRNA is critical for adult hippocampal GABA circuitry"; Nature Neuroscience, vol. 12, No. 8; Aug. 2009; pp. 1020-1027; XP002601250; unnumbered pages from Online Methods (2 pages).
Bond, Allison M. et al.; "Balanced gene regulation by an embryonic brain non-coding RNA is critical for GABA circuitry in adult hippocampus"; Nature Neuroscience Supplementary Text and Figures; Aug. 2009; XP002604372; Retrieved from the internet at http://www.nature.com/neuro/journal/v12/n8/extref/nn.2371-S1. pdf (4 pages).

(Continued)

*Primary Examiner* — Doug Schultz
(74) *Attorney, Agent, or Firm* — Brinks Gilson & Lione

(57) ABSTRACT

The present invention relates to the field of neurological disorders and more particularly to the field of neuropsychiatric disorders. The invention provides non-human, transgenic animal models for brain disorders such as schizophrenia, bipolar disorders, compulsive disorders, addictive disorders and the like. The animals also have applications in the field of GABA neurotransmission and other disorders in which GABA-dependent gene regulation has a role.

17 Claims, 39 Drawing Sheets

(56) References Cited

OTHER PUBLICATIONS

Bulfone A, Wang F, Hevner R, Anderson S, Cutforth T, Chen S, Meneses J, Pedersen R, Axel R, Rubenstein JL. (Dec. 1998) An olfactory sensory map develops in the absence of normal projection neurons or GABAergic interneurons. Neuron. 2: 1273-82.
Bunney et al.; "The Precise Localization of Nigral Afferents in the Rat as Determined by a Retrograde Tracing Technique"; Brain Research, 117; 1976; pp. 423-435.
Caine SB, Negus SS, Mello NK, Patel S, Bristow L, Kulagowski J, Vallone D, Saiardi A, Borrelli E.; Role of dopamine D2-like receptors in cocaine self-administration: studies with D2 receptor mutant mice and novel D2 receptor antagonists. J Neurosci. Apr. 2002; 22(7) :2977-88.
Casanova et al.; "Minicolumnar Pathology in Autism"; Neurology; Feb. 2002; 58; pp. 428-432.
Casarosa, S., Fode, C, Guiellemot, F. (1999) MASH-I regulates neurogenesis in the ventral telencephalon. Development 126, 525-534.
Cassiday, L.A and Maher, L.J. (2002) Having it both ways: transcription factors that bind DNA and RNA Nucleic Acids Research 30: 4118-4126.
Centonze D, Picconi B, Baunez C, Borrelli E, Pisani A, Bernardi G, Calabresi P. (2002) Cocaine and amphetamine depress striatal GABAergic synaptic transmission through D2 dopamine receptors. Neuropsychopharmacology;26: 164-75.
Chahrour, M. et al. MeCP2, a key contributor to neurological disease, activates and represses transcription. Science 320, 1224-1229 (May 30, 2008).
Chahrour, M. & Zoghbi, H.Y. The story of Rett syndrome: from clinic to neurobiology. Neuron 56, 422-437 (Nov. 8, 2007).
Chiang, C, Litingtung, Y., Lee, E., Young, K.E., Gorden, J.L., Westphal, H., and Beachy, PA (Oct. 3, 1996). Cyclopia and defective axial patterning in mice lacking Sonic Hedgehog gene function. Nature 383, 407-413.
Chomczynski, P. & Sacchi, N. Single-step method of RNA tsctatcn by acid guanidinium thiocyanate-phenol-chloroform extraction. Anal. Biochem. 162, 156-159 (1987).
Clark et al.; Nature Reviews; 4:825-833; Oct. 2003.
Clemens, K.R., Wolf, V., McBryant, S.J., Zhang, P., Liao, X., Wright, P.E. and Gottesfeld, J.M. (Apr. 23, 1993) Molecular basis for specifc recognition of both RNA and DNA by a zinc finger protein. Science, 260, 530-533.
Cobos I, Calcagnotto ME, Vi lay thong AJ, Thwin MT, Noebels JL, Baraban SC, Rubenstein JL. (Aug. 2005) Mice lacking Dlx 1 show subtype-specific loss of interneurons, reduced inhibition and epilepsy. Nat Neurosci.8: 1059-68.
Corbin, J., Gaiano, N., Machold, R.P., Langston, A., Fishell, G. (2000) The Gsh-2 homeodomain gene controls multiple aspects of telencephalic development. Development 127, 5007-5020.
Cossette, et al.; "Mutation of *GABRA1* in an autosomal dominant form of juvenile myoclonic epilepsy"; Nature Genetics, vol. 31; Jun. 2002; pp. 184-189.
Cowles, C. R., Hirschhorn, J.N., Altshuler, D. & Lander, E.S. Detection of regulatory variation in mouse genes. Nat. Genet. 32, 432-437 (Nov. 2002).
Crandall JE, Hackett HE, Tobet SA, Kosofsky BE, Bhide PG. (Jun. 2004) Cocaine exposure decreases GABA neuron migration from the ganglionic eminence to the cerebral cortex in embryonic mice. Cereb Cortex. 14(6):665-75.
Crandall JE, McCarthy DM, Araki KY, Sims JR, Ren JQ, Bhide PG. (Apr. 4, 2007) Dopamine receptor activation modulates GABA neuron migration from the basal forebrain to the cerebral cortex. J Neuroscience 27:3813-22.
Cuzon, V.C., Yeh, PW., Cheng, Q. & Yeh, H.H. Ambient GABA promotes cortical entry of tangentially migrating cells derived from the medial ganglionic eminence. Cereb. Cortex 16, 1377-1388 (Oct. 2006).

Dailey JW, Fryer TD, Brichard L, Robinson ES, Theobald DE, Laane K, Peiia Y, Murphy ER, Shah Y, Probst K, Abakumova I, Aigbirhio FI, Richards HK, Hong Y, Baron JC, Everitt BJ, Robbins TW. (Mar. 2, 2007) Nucleus accumbens D2/3 receptors predict trait impulsivity and cocaine reinforcement. Science 315(5816): 1267-70.
Dani, Y.5. et al. Reduced cortical activity due toa shi ft in the balance between excitation and inhibition in a mouse model of Rett syndrome. Proc. Natl. Acad. Sci. USA 102, 12560-12565 (Aug. 30, 2005).
Depew, M. I., Liu, J.K., Long, J.E., Presley, R., Meneses, J.1., Pedersen, R., Rubenstein, J.L.R., 1999. Dlx5 regulates regional development of the branchial arches and sensory capsules. Development 126, 3831-3846.
DePrimo, S. E., Stambrook, P. J. & Stringer, J. R. (1996) Human placental alkaline phosphatase as a histochemical marker of gene expression in transgenic mice. Transgenic Res. 5, 459-466.
Dewey SL, Chaurasia CS, Chen CE, Volkow ND, Clarkson FA, Porter SP, Straughter-Moore RM, Alexoff DL, Tedeschi D, Russo NB, Fowler JS, Brodie JD. (1997) GABAergic attenuation of cocaine-induced dopamine release and locomotor activity. Synapse. 25(4):393-8.
Dewey SL, Smith GS, Logan J, Brodie JD, Yu DW, Ferrieri RA, King PT, MacGregor RR, Martin TP, WoIfAP, et al. (Oct. 1992) GABAergic inhibition of endogenous dopamine release measured in vivo with 11 C-raclopride and positron emission tomography. J Neurosci. 12(10):3773-80.
DiCicco-Bloom et al.; "The Developmental Neurobiology of Autism Spectrum Disorder"; The Journal of Neuroscience; Jun. 28, 2006; 26(26):6897-6906.
Di Cristo, G. Development of cortical GABAergic circuits and its implications for neurodevelopmental disorders. Clin. Genet. 72, 1-8 (2007).
Doss, S., Schadt, E. E., Drake, I.A. & Lusis, AJ. Cis-acting expression Quantitative trait loci in mice. Genome Res. 15, 681-691 (2005).
Drake, R.E.; A. I. Alterman; and S.R. Rosenberg. (Apr. 1993) "Detection of Substance Use Disorders in Severely Mentally Ill Patients." Community Mental Health Journal 29: 175-192.
Dubnau, J., and Struhl, G. (Feb. 22, 1996) RNA recognition and translational regulation by a homeodomain protein. Nature 379, 694-699.
Engelke, D.R., Ng, S. -Y., Shastry, B.5. and Roeder, R. G. (Mar. 1980) Specific interaction of a purified transcription factor with an internal control region of 5S RNA genes. Cell, 19, 717-728.
Erdmann, VA, Barciszewska, M.Z., Hochberg, A., deGroot, N., Barciszewski, J. (2001) Regulatory RNAs. Cellular and Moelcular Life Sciences 58: 960-977.
Faedo, Andrea et al.; "Identification and characterization of a novel transcript down-regulated in D1x1/D1x2 and up-regulated in Pax6 mutant telencephalon"; Developmental Dynamics: An Official Publication of the American Association of Anatomists, vol. 231, No. 3; Nov. 2004; pp. 614-620; XP002601249.
Feng, J. et al. Synergistic and antagonistic roles of the Sonic hedgehog N- and C-terminal lipids. Development 131, 4357-4370 (2004).
Feng, J., Bi, C, Clark, B., Mady, R., Shah, P., Kohtz, J.D. (May 2006) The Evf- 2 non-coding RNA is transcribed from the Dlx 5/6 ultraconserved region and functions as a Dlx-2 homeodomain transcriptional coactivator. Genes and Development, 20: 1470-1484.
Gerfen CR.(1992) The neostriatal mosaic: multiple levels of compartmental organization. Trends Neurosci.15(4): 133-9.
Ghanem, N., Jarinova 0., Amores, A., Long, Q., Hatch, G., Park, BK, Rubenstein, J.L.R., Ekker, M. (2003) Regulatory Roles of Conserved Intergenic Domains in Vertebrate Dlx Bigene Clusters. Genome Research 13: 533-543.
Giacometti, E., Luikenhuis, S., Beard, C & Jaenisch, R. Partial rescue of MeCP2 deficiency by postnatal activation of MeCP2. Proc. Natl. Acad. Sci. USA 104, 1931-1936 (Feb. 6, 2007).
Gilligan, P., Brenner, S., Venkatesh, B. (2002) Fugu and human sequence comparison identifies novel human genes and conserved non-coding sequences. Gene 294, 35-44.

(56) References Cited

OTHER PUBLICATIONS

Giros B, Jaber M, Jones SR, Wightman RM, Caron MG. (Feb. 15, 1996) Hyperlocomotion and indifference to cocaine and amphetamine in mice lacking the dopamine transporter. Nature 379 :606-12.

Graham DL, Edwards S, Bachtell RK, DiLeone RJ, Rios M, SelfDW. (Aug. 2007) Dynamic BDNF activity in nucleus accumbens with cocaine use increases self-administration and relapse. Nat Neurosci. 10: 1029-37.

Graves, L.E., Segal, S. and Goodwin, E.B. (Jun. 24, 1999) TRA-I regulates the cellular distribution of the tra-2 mRNA in C elegans. Nature, 399, 802-805.

Guillemot, F. and Joyner, A. (1993) Dynamic expression of the murine Achaete^ Scute homologue Mash-1 in the developing nervous system. Mech. Dev. 42, 171-185.

Guy, J., Gan, J., Selfridge, J., Cobb, S. & Bird, A. Reversal of neurological defects in a mouse model of Rett syndrome. Science 315, 1143-1147 (Feb. 23, 2007).

Hark, A. T. et al. (May 25, 2000) CTCF mediates methylation-sensitive enhancer-blocking activity at the H19/Igf2 locus. Nature 405, 486-489.

Hatchell EC, Colley SM, Beveridge DJ, Epis MR, Stuart LM, Giles KM, Redfern AD, Miles LE, Barker A, MacDonald LM, Arthur PG, Lui JC, Golding JL, McCulloch RK, Metcalf CB, Wilce JA, Wilce MC, Lanz RB, O'Malley BW, Leedman PJ. (Jun. 9, 2006) SLIRP, a small SRA binding protein, is a nuclear receptor corepressor. Mol Cell. 22(5) :657-68.

Heng, J.I., Moonen, G. & Nguyen, L. Neurotransmitters regulate cell migration in the telencephalon. Eur. J. Neurosci. 26, 537-546 (2007).

Ho et al., "Site-directed mutagenesis by overlap extension using the polymerase chain reaction"; 1989, Gene 77:51-59.

Horike S, Cai S, Miyano M, Cheng JF, Kohwi-Shigematsu T. (Jan. 2005) Loss of silent-chromatin looping and impaired imprinting of DLX5 in Rett syndrome. Nat Genet.37:31-40.

Hyman SE, Malenka RC, Nestler EJ. (2006) Neural mechanisms of addiction: the role of reward-related learning and memory. Annu Rev Neurosci. 29:565-98.

Hyman SE. (Aug. 2005) Addiction: a disease of learning and memory. Am J Psychiatry. 162: 1414-22.

Ikemoto S, Qin M, Liu ZH. (May 18, 2005) The functional divide for primary reinforcement of D-amphetamine lies between the medial and lateral ventral striatum: is the division of the accumbens core, shell, and olfactory tubercle valid? J Neurosci. 25:5061-5.

Ikemoto S. (2002) Ventral striatal anatomy of locomotor activity induced by cocaine, D-amphetamine, dopamine and Dl/o2 agonists. Neuroscience.113:939-55.

Ikemoto S. (Oct. 15, 2003) Involvement of the olfactory tubercle in cocaine reward: intracranial self-administration studies. J Neurosci. 23:9305-11.

Ingham, PW., and McMahon, A.P. 2001. Hedgehog signaling in animal development: paradigms and principles. Genes & Development 15: 3059- 3087.

Jaber M, Cador M, Dumartin B, Normand E, Stinus L, Bloch B. (1995) Acute and chronic amphetamine treatments differently regulate neuropeptide messenger RNA levels and Fos immunoreactivity in rat striatal neurons. Neuroscience. 65(4): 1041-50.

Jeong, Juhee et al.; "Dlx genes pattern mammalian jaw primordium by regulating both lower jaw-specific and upper jaw-specific genetic programs"; Development 135 (17); pp. 2905-2916; Sep. 2008.

Juan, V., Crain, C, Wilson, C. (2000) Evidence for evolutionarily conserved secondary structure in the H 19 tumor suppressor RNA. Nucleic Acids Research 28: 1221-1227.

Kageyama Y. Mengus G. Gilfillan G. Kennedy HG. Stuckenholz C. Kelley RL. Becker PB. Kuroda MI. (2001) Association and spreading of the *Drosophila* dosage compensation complex from a discrete roXl chromatin entry site. EMBO Journal. 20, 2236-45.

Kamman, M. et al., Rapid insertional mutagenesis of DNA by polymerase chain reaction (PCR); 1989; Nucl. Acids Res. 17; p. 5404.

Kellendonk C, Simpson EH, Polan HJ, Malleret G, Vronskaya S, Winiger V, Moore H, Kandel ER. (Feb. 16, 2006) Transient and selective overexpression of dopamine D2 receptors in the striatum causes persistent abnormalities in prefrontal cortex functioning. Neuron. 49:603-15.

Kelly MA, Rubinstein M, Phillips TJ, Lessov CN, Burkhart-Kasch S, Zhang G, Bunzow JR, Fang Y, Gerhardt GA, Grandy DK, Low MJ. (May 1, 1998) Locomotor activity in D2 dopamine receptor-deficient mice is determined by gene dosage, genetic background, and developmental adaptations J Neurosci. 18(9):3470-9.

Keown et al.; "Methods for Introducing DNA into Mammalian Cells"; Methods in Enzymology, vol. 185; 1990; pp. 527-537.

Kishi, N. & Macklis, J.D. MECP2 is progressively expressed in post- migratory neurons and is involved in neuronal maturation rather than cell fate decisions. Mol. Cell. Neurosci. 27, 306-321 (2004).

Kohtz, J.D. and Fishell, G. 2004. Developmental Regulation of EVF-I, a Novel Non-coding RNA Transcribed Upstream of the Mouse Dlx6 Gene. Mechanisms of Development Gene Expression Patterns 4: 407-412.

Kohtz, J.D., Baker, D.P. Cortes, G., Fishell, G. (1998) Regionalization within the mammalian telencephalon is mediated by changes in responsiveness to Shh. Development 125, 5079-5089.

Kohtz, J.D., Lee, H. Y., Gaiano, N., Segal, J.D., Ng, E., Larson, TA, Baker, D.P., Garber, EA, Williams, K.P., Fishell, G. (2001) N-terminal fatty- acylation of Sonic Hedgehog enhances the induction of rodent ventral forebrain neurons. Development 128 :2351-2363.

Kunkel, T. A. et al., "Rapid and efficient site-specific mutagenesis without phenotypic selection"; Jan. 1985; Proc. Natl. Acad. Sci. USA, vol. 82, pp. 488-492.

Kuwabara T, Hsieh J, Nakashima K, Taira K, Gage FH. (Mar. 19, 2004) A small modulatory dsRNA specifies the fate of adult neural stem cells. Cell: 19;116:779-93.

Lanz, R.B., McKenna, N.J., Onate, SA, Albrecht, U., Wong, J., Tsai, S.Y., Tsai, MJ. , O'Malley, B. Apr. 2, 1999. A Steroid Receptor Coactivator, SRA, Functions as an RNA and Is Present in an SRC-I Complex. Cell 97: 17-27.

Le, TN, Du, G., Fonseca, M., Zhou, O.P., Wiglell, JT, Eisenstat, o.o. (Jun. 29, 2007) Dlx Homeobox Genes Promote Cortical Interneuron Migration from the Basal Forebrain by Direct Repression of the Semaphorin Receptor Neuropilin-2. J. Biol. Chem., 282: 19071-19081.

Lee M.P., DeBaun, MR, Mitsuya, K., Galonek, H.L., Brandenburg, S., Oshimura, M. et al. (Apr. 1999) Loss of imprinting of a paternally expressed transcript with anti-'sense oritntation to KVLQTI occurs frequently in Beckwith- Wiedemann syndrome and is independent of insulin-like growth factor II imprinting. Proc. Natl Acad Sci. USA 96: 5203-5208.

Lee, EC, Yu, D, de Velasco, JM, Tessarollo, L., Sing, DA, Court, D., Jenkins, NA, Copeland, NG. (2001) A highly efficient *E.coli* based chromosome engineering system adapted for recombinogenic targeting and subcloning of BAC DNA. Genomics 73: 56-65.

Lee, J.T., Davidov, L.5., and Varshawsky, D. (Apr. 1999) Tsix, a gene antisense to Xist at the X-inactivation centre. Nat. Genet. 21 : 400-404.

Levi, G., Puche, A.C., Mantero, S., Barbieri, 0., Trombino, S., Paleari, L., Egeo, A., Merlo, G.R., 2003. The Dlx5 homeodomain gene is essential for olfactory development and connectivity in the mouse. Mol. Cell. Neurosci. 22, 530-543.

Lewis, D.A., Hesturncto.T. & Yolk, OW. Cortical inhibitory neurons and schizophrenia. Nat. Rev. Neurosci. 6, 312-324 (Apr. 2005).

Liu JK, Ghattas I, Liu S, Chen S, Rubenstein JL. (1997) Dlx genes encode DNA-binding proteins that are expressed in an overlapping and sequential pattern during basal ganglia differentiation. Developmental Dynamics, 210, 498-512.

Liu J, Wang J, Hu J, Tian B. (Apr. 7, 2005) A method for aligning RNA secondary structures and its application to RNA motif detection BMC Bioinformatics. I 0.1186/1471-21 May 6, 1989.

(56) References Cited

OTHER PUBLICATIONS

Liu P, Jenkins NA & Copeland NG. A highly efficient recombineering- based method for generating conditional knockout mutations. Genome Res. 13, 476-484 (2003).
Lois C and Alvarez-Buylla A. (May 20, 1994). Long-distance neuronal migration in the adult mammalian brain. Science 264, 1145-1148.
Long JE, Garel S, Depew MJ, Tobet S, Rubenstein JLR. Jan. 15, 2003. DLX5 regulates development of peripheral and central components of the olfactory system. J. Neurosci. 23, 568-578.
Lopez-Bendito, G. et al. Blockade of GABA(B) receptors alters the tangential migration of cortical neurons. Cereb. Cortex 13, 932-942 (Sep. 2003).
Lou XY, Ma JZ, Sun D, Payne T J, Li MD. Fine mapping of a linkage region on chromosome 17pl3 reveals that GABARAP and DLG4 are associated with vulnerability to nicotine dependence in European- Americans. Hum Mol Genet. Jan. 15, 2007;16(2): 142-53. Epub Dec. 12, 2006.
Ma et al.; "Identification of Significant Association and Gene-Gene Interaction of GABA Receptor Subunit Genes in Autism"; Am. J. Hum. Genet. 77:377-388; 2005.
Mancini-DiNardo D, Steele SJ, Levorse JM, Ingram RS & Tilghman SM. Elongation of the Kcnq lot I transcript is required for genomic imprinting of neighboring genes. Genes Dev. 20, 1268-1282 (2006).
Marin O and Rubenstein JL. (2003)Cell migration in the forebrain. Annu Rev Neurosci. 26:441-83.
Marin O, Anderson SA, Rubenstein JL. (Aug. 15, 2000) Origin and specification of striatal interneurons. J. Neuroscience 20, 6063-6076.
Martinez D, Brott A, Foltin RW, Slifstein M, Hwang DR, Huang Y, Perez A, Frankie WG, Cooper T, Kleber HD, Fischman MW, Laruelle M.(2004) Cocaine dependence and d2 receptor availability in the functional subdivisions of the striatum: relationship with cocaine-seeking behavior. Neuropsychopharmacology.29(6): 1190-202.
Martinho RG, Kunwar PS, Casanova J, and Lehmann R. (Jan. 20, 2004) A Noncoding RNA Is Required for the Repression of RNApolII-Dependent Transcription in Primordial Germ Cells Current Biology, 14, 159-165.
Mattick JS. (2007) A new paradigm for developmental biology. The Journal of Experimental Biology 210, 1526-1547.
Maxwell IH, Harrison GS, Wood WM, and Maxwell F. (1989) A DNA cassette containing a trimerized SV40 polyadenylationj signal hich efficiently blocks spurious plasmid-initiated transcription. Biotechniques 7, 276-280.
Meller VH, Wu KH, Roman G, Kuroda MI, Davis RL. (Feb. 21, 1997) roXl RNA paints the X chromosome of male *Drosophila* and is regulated by the dosage compensation system. Cell 88, 445-457.
Mercer TR, Dinger ME, Sunkin SM, Mehler ME & Mattick JS. Specific expression oflong ncnccnng RNAs in the mouse brain. Proc. Natl. Acad. Sci. USA 105, 716-721 (Jan. 15, 2008).
Montzka Wassarman, and K., Storz, G. (Jun. 9, 2000) 6S RNA Regulates *E. coli* RNA Polymerase Activity. Cell, 101, 613-623.
Moretti, P. & Zoghbi, H.Y. MeCP2 dysfunction in Rett syndrome and related disorders. Curr. Opin. Genet. Dev. 16, 276-281 (2006).
Mrzljak L, Bergson C, Pappy M, Huff R, Levenson R, Goldman-Rakic PS. (May 16, 1996) Localization of dopamine D4 receptors in GABAergic neurons of the primate brain.) Nature. May 16, 1996;381(6579):245-8.
Nader MA, Morgan D, Gage HD, Nader SH, Calhoun TL, Buchheimer N, Ehrenkaufer R, Mach RH. (Aug. 2006) PET imaging of dopamine D2 receptors during chronic cocaine self-administration in monkeys. Nat Neurosci. 9(8): 1050-6.
Nan, X., Campoy, EJ. & Bird, A. MeCP2 is a transcriptional repressor with abundant binding sites in genomic chromatin. Cell 88, 471-481 (Feb. 21, 1997).
National Association of State Mental Health Program Directors and National Association of State Alcohol and Drug Abuse Directors. National Dialogue on Co-Occurring Mental Health and Substance Abuse Disorders. Alexandria, Va.: NASMHPD and NASADAD, Mar. 1999.
NCI-Frederick: Recombineering Information; "Recombineering Reagent"; downloaded from http://web.ncifcrf.gov/research/brb/recombineeringInformation.aspx on Apr. 16, 2012.
Nemes JP, Benzow KA, and Koob MD. (2000) The SCA8 transcript is an anti-sense RNA to a brain-specific transcript encoding a novel actin- binding protein. Hum. Mol. Genet. 9: 1543-1551.
Nery S, Fishell G, Corbin JG (Dec. 2002) The caudal ganglionic eminence is a novel source of distinct cortical and subcortical cell populations. Nat Neurosci 5: 1279-1282.
Nguyen VT, Kiss T, Michels AA, Bensaude (Nov. 15, 2001) 7SK small nuclear RNA binds to and inhibits the activity of CDK9/cyclin T complexes. Nature 414, 322-325.
Ninomiya et al. (1996) Isolation of a testis-specific cDNA on chromosome 17q from a region adjacent to the breakpoint of t(12, 17) observed in a patient with acampomelic campomelic dysplasia and sex reversal. Hum. Mol. Genet. 5: 69-72.
Noebels, "The Biology of Epilepsy Genes"; Annu. Rev. Neurosci; 2003; 26:599-625.
Panganiban G. Rubenstein JL. (2002) Developmental functions of the Distalless/Dlx homeobox genes. Development 129, 4371-86.
Panganiban G, Sebring A, Nagy L, and Carroll S. (Nov. 24, 1995). The development of crustacean limbs and the evolution of arthropods. Science 270, 1363-1366.
Piazza PV, Rouge-Pont F, Derniniere JM, Kharoubi M, Le Moal M, Simon H. (1991) Dopaminergic activity is reduced in the prefrontal cortex and increased in the nucleus accumbens of rats predisposed to develop amphetamine self administration. Brain Research 567(1 ): 169-74.
Pleasure SJ, Anderson S, Hevner R, Bagri A, Marin 0, Lowenstein DH, Rubenstein JL. (Dec. 2000) Cell migration from the ganglionic eminences is required for the development of hippocampal GABAergic interneurons. Neuron 28:727-40.
Potier B, Jcwenceau A, Epelbaum J & Dutar P. Age-related alterations of GABAer' gc input toCAI pyramidal neurons and its control by nicotinic acetylcholine receptors in rat hippocampus. Neuroscience 142, 187-201 (2006).
Prasanth KV, Spector DL (2007) Eukaryotic regulatory RNAs: an answer to the 'genome complexity' conundrum Genes & Development 21 : 11-42.
Qui et al.; "Null mutation of Dlx-2 results in abnormal morphogenesis of proximal first and second branchial arch derivatives and abnormal differentiation in the forebrain"; Genes & Development 9:2523-2538; 1995.
Ritz MC, Lamb RJ, Goldberg SR, Kuhar MJ. (Sep. 4, 1987) Cocaine receptors on dopamine transporters are related to self-administration of cocaine. Science. 237: 1219-23.
Robledo RF, Rajan L, Li X, Lufkin T. (2002) The Dlx5 and Dlx6 homeobox genes are essential for craniofacial, axial, and appendicular skeletal development. Genes and Development 16: 1089-1101.
Sabarinadh C, Subramanian S, Tripathi A, Mishra RK; Oct. 6, 2004. Extreme conservation of noncoding DNA near HoxD complex of vertebrates. BMC Genomics 5: 75.
Saccone SF, Hinrichs AL, Saccone NL, Chase GA, Konvicka K, Madden PA, Breslau N, Johnson EO, Hatsukami D, Pomerleau 0, Swan GE, Goate AM, Rutter J, Bertelsen S, Fox L, Fugman D, Martin NG, Montgomery GW, Wang JC, Ballinger DG, Rice JP, Bierut LJ Cholinergic nicotinic receptor genes implicated in a nicotine dependence association study targeting 348 candidate genes with 3713 SNPs. Hum Mol Genet. Jan. 1, 2007 : 16(1 ):36-49. Epub Nov. 29, 2006.
Sanchez -Eisner T, Gou D, Kremmer E, Sauer F. (Feb. 24, 2006) Noncoding RNAs of trithorax response elements recruit *Drosophila* Ashl to Ultrabithorax. Science 311 : 1118-23.
Sandelin A, Bailey P, Bruce S, Engstrom PG, Klos JM, Wasserman WW, Ericson J, Lenhard B.; Dec. 21, 2004. Arrays of ultraconserved non-coding regions span the loci of key developmental genes in vertebrate genomes. BMC Genomics 5: 99.

(56) References Cited

OTHER PUBLICATIONS

Santini S., Boore J.L., Meyer A 2003. Evolutionary conservation of regulatory elements in vertebrate Hox gene clusters. Genome Res. 13: 1111-1122.
Sasaki, H., Hui, CC, Nakafuku, M., Kondoh, H. (1997) A binding site for Gli proteinms is essential for the HNF-3b floor plate enhancer activity in transgenics and can respond to Shh in vitro. Development 124, 1313-1322.
Schaeren-Wiemers, N. and Gerfin-Moser, A (1993) A single protocol to detect transcripts of various types and expression levels in neural tissue and cultured cells; in situ hybridization using digoxigenin- labeled cRNA probes. Histochemistry 100, 431-440.
Schmidt, J. V., Levorse, J. M. & Tilghman, S. M. (Aug. 1999) Enhancer competition between H19 and IgI2 does not mediate their imprinting. Proc. Natl Acad. Sci. USA 96, 9733-9738.
Schule, B., Li, H.H., Fisch-Kohl, C, Purmann, C. & Francke, U. DLX5 and DLX6 expression is biallelic and not modulated by MeCP2 deficiency. Am. J. Hum. Genet. 81, 492-506 (Sep. 2007).
Shamovsky, 1. & Nudler, E. Gene control by large noncoding RNAs. Sci. STKE 2006, pe40 (Oct. 3, 2006).
Sleutels, F., Zwart, R., Barlow, D. P. (Feb. 14, 2002) The non-coding Air RNA is required for silencing autosomal imprinted genes. Nature 415, 810-813.
Small et al.; "Analysis of a Transgenic Mouse Containing Simian Virus 40 and v-myc Sequences"; Apr. 1985; Mol. Cell. Biol. 5:642-648.
Snyder E.Y., Deitcher, D.L., Walsh, C, Arnold-Aldea, S., Hartwieg, EA, Cepko, CL. (Jan. 10, 1992). Mutipotential neural cell lines can engraft and participate in development of mouse cerebellum. Cell 68, 33-51.
Soriano P. (1999) Generalized IacZ expression with the ROSA26 Cre reporter strain. Nat. Genet. 21 : 70-71.
Spitz et al.; "A Global Control Region Defines a Chromosomal Regulatory Landscape Containing the HoxD Cluster"; Cell; vol. 113, pp. 405-417; May 2, 2003.
Stuhmer T, Anderson SA, Ekker M, Rubenstein JL. 2002. Ectopic expression of the Dlx genes induces glutamic acid decarboxylase and Dlx expression. Development. 129 :245-52.
Sui, G., Soohoo, C, Ajar el, B., Gay, F., Shi, Y. and Forrester, W.C. (Apr. 16, 2002)A DNA vector basede RNAi technology to suppress gene expression in mammalian cells. Proc. Natl. Acad. Sci. USA 99, 5515-5520.
Sung et al.; Journal of Biochemistry and Molecular Biology; vol. 37, No. 1; Jan. 2004; pp. 122-132.
Sussel, L., Marin, 0., Kimura, S., Rubenstein, J.L. (1999) Loss of Nkx2.1 homeobox gene function results in a ventral to dorsal molecular respecification within the basal telencephalon: evidence for a transformation of the pallidum into the striatum. Development 126, 3359-3370.
Sutherland, HF, Wadey, R., McKie J.M., Taylor C, Atif U., Johnstone KA, et. al. (1996) Identification of a novel transcript disrupted by a balanced translocation associated with DiGeorge Syndrome. Am. J.Hum. Genet. 59: 23-31.
Szucsik, J.C., Witte, D.P., Li, H., Pixley, SK, Small, K.M. and Potter, S.5. (1997) Altered forebrain and hindbrain development in mice mutant for the Gsh-2 homeobox gene. Dev. Biol. 191, 230-242.
Thomson, A.M., J.T., Rogers, Walker, CE. , Staton, J.M., Leedman, PJ. (Nov. 1999) Opitimized RNA Gel-shift and UV cross-linking assays for characterization of cytoplasmic RNA-Protein interactions. Biotechniques 27: 1032-1039.
Torreson, H., Potter, S.5., Campbell, K. (2000) Genetic control of dorsal-ventral identity in the telencephalon: opposing roles of Gsh2 and Pax6. Development 127, 4361-4371.
Trantham-Davidson H, Neely LC, Lavin A, Seamans JK. (Nov. 24, 2004) Mechanisms underlying differential D 1 versus D2 dopamine receptor regulation of inhibition in prefrontal cortex. J Neurosci.24: 10652-9.
Volkow ND, Fowler JS, Wang GJ, Hitzemann R, Logan J, Schlyer DJ, Dewey SL, WolfAP (1993) Decreased dopamine D2 receptor availability is associated with reduced frontal metabolism in cocaine abusers. Synapse 14(2): 169-77.
Washietl S, Hofacker IL, Lukasser M, Huttenhofer A, Stadler PF. (Nov. 2005) Mapping of conserved RNA secondary structures predicts thousands of functional noncoding RNAs in the human genome. Nat Biotechnol. 23: 1383-90.
Wichterle, H., Turnbull, D.H., Nery, S., Fishell, G., and Alvarez-Buylla, A. (2001). In utero fate mapping reveals distinct migratory pathways and fates of neurons born in the mammalian basal forebrain. Development 128, 3759-3771.
Woloshin, P., K. Song, C. Degnin, A. M. Killary, D. J. Goldhamer, D. Sassoon, and M. J. Thayer. Aug. 25, 1995. MSXI inhibits MyoD expression in fibroblast 3X 10T1/2 cell hybrids. Cell 82:611-620.
Woolfe A, Goodson M, Goode DK, Snell P, McEwen GK, Vavouri T, Smith SF, North P, Callaway H, Kelly K, Walter K, Abnizova I, Gilks W, Edwards YJ, Cooke JE, Elgar G. 2005. Highly conserved non-coding sequences are associated with vertebrate development. PLoS Bio 1.3(1 ):e7; 26 pages.
Wutz, A. et al. (2001) Non-imprinted Igf2r expression decreases growth and rescues the Tme mutation in mice. Development 128, 1881-1887.
Xu, C, Cui, C. & Alkon, D. L. Age-dependent enhancement of inhibitory synaptic transmission in CAI pyramidal neurons via GluR5 kainate receptors. Hippocampus (2009).
Yan, H., Yuan, W., Veiculescu, V.E., Vogel stein, B. & Kinzler, KW. Allelic variation in human gene expression. Science 297, 1143 (Aug. 16, 2002).
Yang, Z., Zhu, Q., Luo, K., Zhou, Q. (Nov. 15, 2001) The 7SK small nuclear RNA inhibits the CDK9/cyclin TI kinase to control transcription. Nature 414, 317-322.
Yelin, R. et al. Widespread occurrence of antisense transcription in the human genome. Nat. Biotechnol. 21, 379-386 (2003).
Yun, K., Potter, S., Rubenstein, J.L. (2001) Gsh2 and Pax6 play complementary roles in dorsal ventral patterning of the mammalian telencephalon. Development 128, 193-205.
Zerucha, T. et al. A highly conserved enhancer in the Dlx5/Dlx6 intergenic region is the site of cross-regulatory interactions between Dlx genes in the embryonic forebrain. J. Neurosci. 20, 709-721 (Jan. 15, 2000).
Zhang H. Hu G. Wang H. Sciavolino P. Her N. Shen MM. Abate-Shen C. Heterodimerization of Msx and Dlx homeoproteins results in functional antagonism. (May 1997) Molecular & Cellular Biology. 17:2920-32.
Zhou, Q. P. et al. roentncencn of a direct Dlx homeodomain target in the developing mouse forebrain and retina by optimization of chromatin immunoprecipitation. Nucleic Acids Res. 32, 884-892 (2004).
Zwart, R., Sleutels, F., Wutz, A., Schinkel, A. H. & Barlow, D. P. (2001) Bidirectional action of the Igf2r imprint control element on upstream and downstream imprinted genes. Genes Dev. IS, 2361-2366.
International Search Report completed Sep. 24, 2010 for International Application No. PCT/US2010/042373.
Written Opinion of the International Searching Authority completed Sep. 24, 2010 for International Application No. PCT/US2010/042373.
International Preliminary Report on Patentability completed Jun. 8, 2011 for International Application No. PCT/US2010/042373.

\* cited by examiner

ANIMAL MODELS OF NEUROLOGICAL DISORDERS

RELATED APPLICATIONS

This application is a divisional application of U.S. application Ser. No. 13/383,539, filed Mar. 29, 2012, which claims the benefit under 35 U.S.C. §371 of International Application No. PCT/US2010//042373, filed Jul. 17, 2010, which claims the benefit of U.S. Provisional Application Ser. No. 61/226,394, filed Jul. 17, 2009. These references are incorporated herein in their entirety.

REFERENCE TO SEQUENCE LISTING SUBMITTED VIA EFS-WEB

This application is being filed electronically via EFS-WEB and includes an electronically submitted Sequence Listing in .txt format. The .txt file contains a sequence listing created on Feb. 11, 2014 and is 20 kb in size. The sequence listing contained in the .txt file is part of the specification and is hereby incorporated by reference herein in its entirety.

FIELD OF THE INVENTION

The present invention relates to the field of neurological disorders and more particularly to the field of neuropsychiatric disorders. The invention provides non-human, transgenic animal models for neurological disorders such as schizophrenia, drug addiction, autism, learning disorders, mood disorders, behavioral disorders and the like. The animals also have applications in the field of GABAergic interneuron development related disorders and other disorders in which GABA-dependent neurotransmission has a role.

BACKGROUND

The balance between excitation and inhibition in the brain is important for proper function and is maintained by two major classes of neurons: excitatory projection neurons and inhibitory local circuit interneurons. While excitation is primarily mediated by the neurotransmitter glutamate, GABA primarily mediates inhibition. Recently, multiple regulatory roles of GABAergic interneurons have been identified (Di Cristo, 2007). GABAergic interneurons regulate neuronal proliferation, migration and differentiation during development, as well as excitability, temporal synchrony and refinement of local cortical circuits. The dysfunction of GABA-regulated circuits has been implicated in different psychiatric disorders such as schizophrenia, autism, and Tourette's syndrome, as well as epilepsy (Blatt et al. 2001; Casanova et al. 2002; Cossette et al., 2002; DiCicco-Bloom et al. 2006; Ma et al. 2005; Noebels, 2003). In methyl CpG-binding protein (Mecp2) mutant mice (Bienvenu and Chelly, 2006; Chahrour and Zoghbi, 2007; Moretti and Zoghbi, 2006), a model for the human autism spectrum disorder (ASD) Rett syndrome, GABA-dependent inhibitory cortical activity decreases (Dani et al. 2005). In dorsal lateral prefrontal cortex of schizophrenic patients, one of the most consistent findings is a reduction in GAD67, the enzyme responsible for GABA synthesis (Lewis et al. 2005). Therefore, multiple lines of evidence implicate alterations of GABAergic function in a variety of neurological diseases.

Yet, despite this knowledge of brain function, there remains a need for the development of animal models for the discovery of therapeutic agents for use in preventing or treating such neurological diseases.

SUMMARY

In one embodiment, the present invention provides a non-human transgenic animal characterized by having reduced expression of a functional non-coding RNA Evf1 and/or Evf2.

In another embodiment, the present invention provides methods for the production of an animal model of autism, comprising transforming an animal cell with a recombinant nucleic acid construct capable of reducing or eliminating the expression of a functional ncRNA Evf2 in the animal, and regenerating a mutant animal having reduced expression of a functional ncRNA Evf2 in a brain tissue.

The present invention also provides methods for the production of an animal model of drug addiction or schizophrenia, comprising transforming an animal cell with a recombinant nucleic acid construct capable of reducing or eliminating the expression of a functional ncRNA Evf1 in the animal; and regenerating a mutant animal having reduced expression of a functional ncRNA Evf1 in a brain tissue.

In still another embodiment, the present invention provides methods for the production of an animal model of brain disorders, comprising: crossing a first transgenic non-human animal having reduced expression of a functional non-coding RNA Evf1 and/or Evf2 with a second non-human animal; and selecting from the first generation offspring a transgenic non-human animal having a genome comprising at least one recombinant nucleic acid comprising a sequence for introducing a transcription stop sequence into an exon of an Evf sequence.

The present invention also provides methods for identifying a therapeutic agent for treating a brain disorder, comprising administering a test agent to a non-human transgenic animal having reduced expression of a functional non-coding RNA Evf1 and/or Evf2, and analyzing the response of the non-human transgenic animal to the test agent, where alleviation of at least one brain disorder symptom is indicative of a therapeutic effect.

The present invention also provides methods for determining the therapeutic efficacy of a test agent, comprising: administering a test agent to a first non-human transgenic animal having reduced expression of a functional non-coding RNA Evf1 and/or Evf2; measuring the levels of a symptom of a brain disorder; and comparing the levels of the symptom with levels of a second non-human transgenic animal of the same type to which the test agent has not been administered, where an improvement in symptoms in the first non-human animal is indicative of the efficacy of the test agent.

In another embodiment, the present invention provides methods for screening agents for preventing or treating drug addiction, comprising administering a test agent to a first non-human transgenic animal having reduced expression of a functional ncRNA Evf1; measuring a response of the first animal to a psychostimulatory drug; and comparing the response with the response of a second non-human transgenic animal of the same type to which the test agent has not been administered, where an improvement in the response to a psychostimulatory drug in the first non-human animal is indicative of the efficacy of the test agent for treating or preventing drug addiction.

In still a further embodiment, the present invention provides methods for screening agents for treating a mood disorder, comprising administering a test agent to a first non-human transgenic animal having reduced expression of a functional ncRNA Evf2; measuring at least one symptom of the mood disorder; and comparing the measurement of the at least one symptom to the measurement of the at least one symptom of a second non-human transgenic animal of the same type to which the test agent has not been administered, where an improvement in the at least one symptom measurement in the first non-human animal is indicative of the efficacy of the test agent for treating a mood disorder.

In still a further embodiment, the present invention provides methods for screening agents for treating an autism spectrum disorder, comprising administering a test agent to a first non-human transgenic animal having reduced expression of a functional ncRNA Evf2; measuring at least one symptom of the autism spectrum disorder; and comparing the measurement of the at least one symptom to the measurement of the at least one symptom of a second non-human transgenic animal of the same type to which the test agent has not been administered, where an improvement in the at least one symptom measurement in the first non-human animal is indicative of the efficacy of the test agent for treating an autism spectrum disorder.

BRIEF DESCRIPTION OF THE DRAWINGS

FIG. 1(a) provides a schematic drawing of an example of the targeting of a triple polyadenylation transcription stop site into Evf exon 1, truncating Evf2 transcripts from 3.7 kb to 101 bp (Evf2TS), but not Evf1, which is transcribed starting from exon 3. Truncated Evf2TS transcript (101 bp) completely lacks the ultraconserved ei region. Only the distance from the triple polyadenylation signal insertion to the Dlx5 (1310.2 kb) and Evf1 (1310.4 kb) transcription start sites are shown to scale. FIG. 1(b) provides one embodiment of ES cells that were used for making Evf2TS/TS mice contained correctly targeted transcription stop into Evf exon 1, as verified by Southern analysis. FIGS. 1(c-h) provides the results of an RNA in situ hybridization of E13.5 coronal sections of wild-type (WT) and Evf2TS/TS mutant telencephalon, probed with anti-sense Evf2 (c,d), anti-sense Evf1 (e,f) or anti-sense Dlx5 (g,h). FIG. 1(i) provides a representation of one embodiment of the present invention showing that gene expression changes in the Evf2 TS/TS E13.5 MGE. Triple polyA insertion knocks down expression of Evf2. While Dlx 5 and 6 are upregulated, Evf1 and neurpilin2 do not change. Quantitative real-time RT-PCR analysis of pooled E13.5 MGE tissue from wt (wild-type littermate controls, n=4), and Evf2 TS/TS (n=6 for all by Evf2 analysis where n=3) embryos. Student's t-test analysis, * p<0.05. Error bars represent s.e.m. Statistical analysis: Mann Whitney U-test, P<0.05: Evf2=0.0055, Dlx5=0.044, Dlx6=0.0055; n=4 for wild type, n=6 for Evf2TS/TS. FIG. 1(j) provides the results of a quantitative Q21 real-time RT-PCR analysis of E12.5 Evf2TS/TS mutant MGE electroporated with 2 mg pcNDA (control), 1 μg pcDNA-Evf2 and 1 μg pcDNA), and 2 μg pcDNA-Evf2. Error bars represent s.e.m. Statistical analysis, ANOVA Dunnett's two-sided test, P<0.05 values: Dlx5, (0 μg, 1 μg Evf2=0.05, 0 μg, 2 μg Evf2=0.001), ANOVA Tukey test, P<0.05 values, Dlx6 (0 μg, 2 μg Evf2=0.041, 1 μg Evf2, 2 μg Evf2=0.033); n=4. * P<0.05; t-test, Mann Whitney, or ANOVA.

FIG. 2(a) provides an example of a schematic representation showing the region in mouse chromosome 6qA1 surrounding Dlx 5/6 and Evf1/2. FIGS. 2(b-d) provides the results of a quantitative ChIP of E13.5 MGE from wild types (black bars) and Evf2 TS/TS mutants (gray bars) using primers 1-6 across the Dlx5/6 region and panantibody to DLX (p<0.05 values: 3=0.025, 5=0.025; b), antibody to MECP2 (p<0.05 values: 2=0.025, 3=0.025, 5=0.025; c) or antibody to HDAC1 (P<0.05 values: 5=0.025, 6=0.025; d) qChIP-PCR was performed on optimized primer sets using previously defined primer sets (1=15, 2=24, 4=27) and newly defined sets for ei (3, red), eii (5, red) and external primer (6). Primer 2 (green) was identified as a MECP2/HDAC-binding site for transcriptional repression in adult cortex. Error bars represent s.e.m. *P<0.05, Mann Whitney U test. The schematic in (a) is reversed from that shown for Evf2 transcription-stop insertion (FIG. 1) to align with previously published primers.

FIG. 3(a) provides Western blot analysis of DLX2 protein after transfection of a construct containing Dlx2 cDNA and/or Evf2 cDNA. Transfection was performed in C17 mouse neural stem cells in the presence or absence of Evf2 RNA, showing equal levels of DLX2 protein. It was determined that Evf2 RNA was stable after transfection by RT-PCR (data not shown). FIG. 3(b) provides Western analysis of Evf2TS/TS and wild-type E13.5 ganglionic eminence extracts probed with antibody to DLX2 (gift of D. Eisentstat) showing that loss of Evf2 did not affect DLX2 protein levels. FIGS. 3(c-h) Pan-antibody to DLX (green) stained nuclei that were counterstained with DAPI (blue) in both wild-type and Evf2TS/TS E13.5 MGE SVZ, subventricular zone; VZ, ventricular zone. Scale bars represent 200 μm (c,f), 20 μm (d,g) and 10 μm (e,h). FIGS. 3(i,j) provide immuno-histochemistry using antibodies to MECP2 (green) and DAPI (blue nuclei) showing similar nuclear localization in both wild-type and Evf2TS/TS MGE cells. Scale bar represents 20 mm.

FIG. 4(a) provides RNA in situ hybridization analysis of Evf2 expression in the subventricular zone and cells lining the lateral ventricle as they migrate to the hippocampus and dentate gyrus. Scale bar represents 130 μm. DG, dentate gyrus; DGC, dentate granule cell layer; LMol, lacunosum molecular; LV, lateral ventricle; Mol, molecular layer of the dentate gyrus; Or, oriens; Py, pyramidal; Rad, radiatum. FIG. 4(b) provides quantification of the number of GAD67-expressing GABAergic interneurons in the dentate gyrus and hippocampal CA1 and CA3 regions. Error bars represent s.e.m. P=0.025 for dentate gyrus, CA3 and CA1, Mann Whitney U test (n=3 for wild type, n=3 for Evf2TS/TS). FIGS. 4 (c,d) provides RNA in situ hybridization of Gad 1-expressing interneurons in the hippocampus. Scale bar represents 135 μm. FIGS. 4(e,f) provide results of immunohistochemistry with antibodies to GABA (green) and DAPI (blue nuclei). Scale bar represents 200 μm. FIGS. 4(g,h) provide RNA in situ hybridization of vGlut1-expressing neurons in the hippocampal CA3 region showing similar expression in wild type and Evf2TS/TS. Scale bar represents 80 μm. FIGS. 4(i,j) provide immunohistochemistry using the apoptosis TUNEL assay (green) and DAPI (blue nuclei) in the hippocampal CA3 region. Scale bar represents 10 μm. FIG. 4(k) provides quantification of the number of TUNEL-positive cells in the dentate gyrus and hippocampal CA1 and CA3 regions showing no difference in cell death between wild types and Evf2TS/TS mutants. Error bars represent s.e.m.

P<0.05 for dentate gyrus, CA3 and CA1, Student's t test (n=3 for wild types, n=3 for Evf2TS/TS). * P<0.05 (t test or Mann Whitney U test).

Figures 5A, 5B, 5C, 5D:
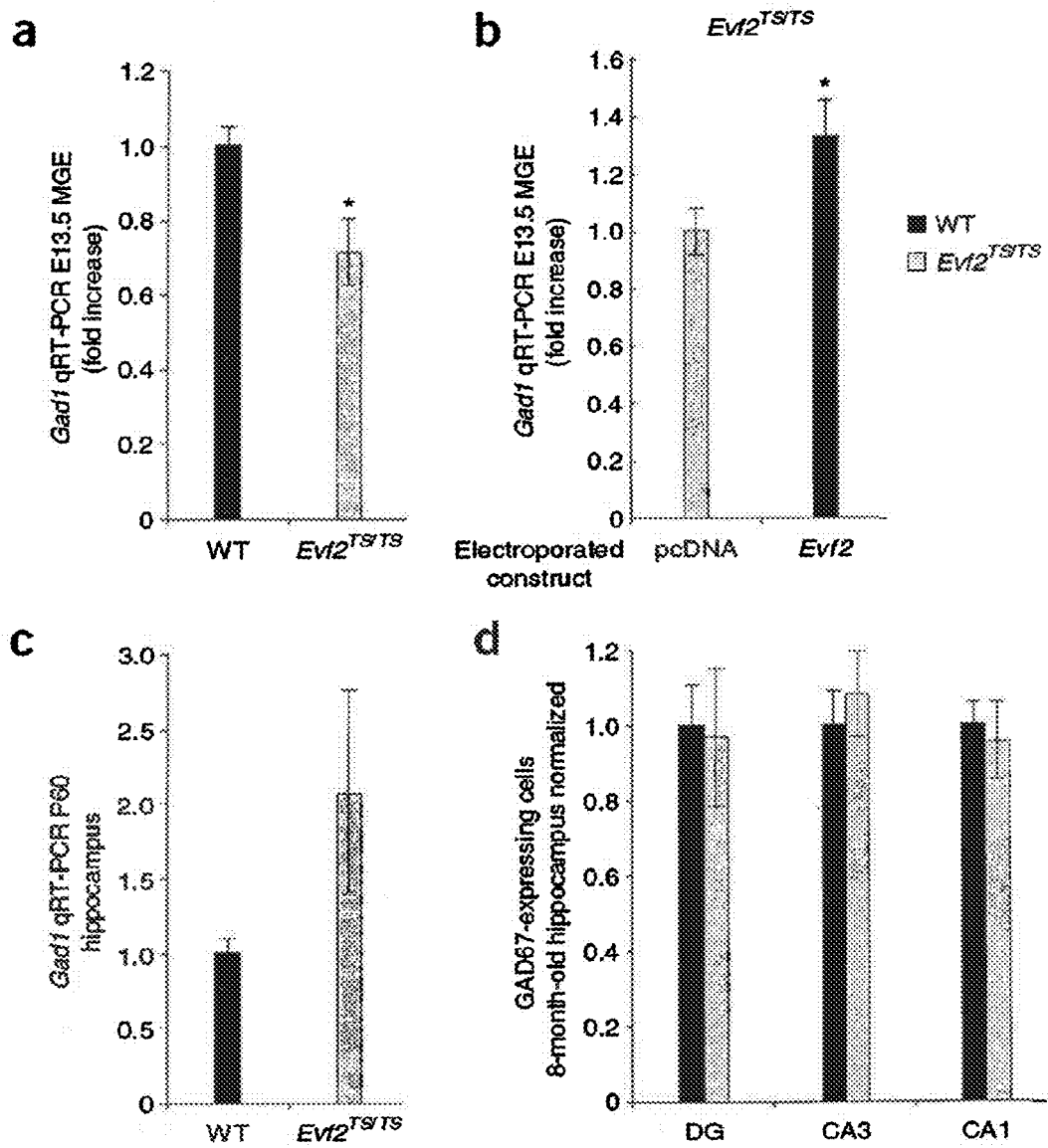

FIGS. 5a-5d provide an example of data of Evf2 trans-positively regulates Gad1 expression in E13.5 MGE, but not adult hippocampus. FIG. 5(a) provides quantitative real-time RT-PCR analysis of Gad1 in E13.5 MGE from wild types and Evf2TS/TS mutants. Error bars represent s.e.m. P=0.031, Student's t-test (n=3 for wild types, n=5 for Evf2TS/TS). FIG. 5(b) provides quantitative real-time RT-PCR analysis of Gad1 in E12.5 Evf2TS/TS mutant MGE electroporated with control (pcDNA, 2 mg) and 2 mg pcDNA-Evf2. Error bars represent s.e.m. P=0.0375, Student's t-test (n=4). FIG. 5(c) provides quantitative real-time RT-PCR analysis of Gad1 in P60 hippocampus from wild types and Evf2TS/TS mutants. Error bars represent s.e.m. P=0.031, Student's t test (n=2 for wt, n=2 for Evf2TS/TS). FIG. 5(d) provides quantification of the number of GAD67-expressing GABAergic interneurons in 8-month-old dentate gyrus and hippocampal CA3 and CA1 regions. Error bars represent s.e.m. P>0.05 for dentate gyrus, CA3 and CA1, Student's t test (n=3 for wild types, n=3 for Evf2TS/TS). * P<0.05, t test.

Figures 6A, 6B, 6C, 6D, 6E, 6F:
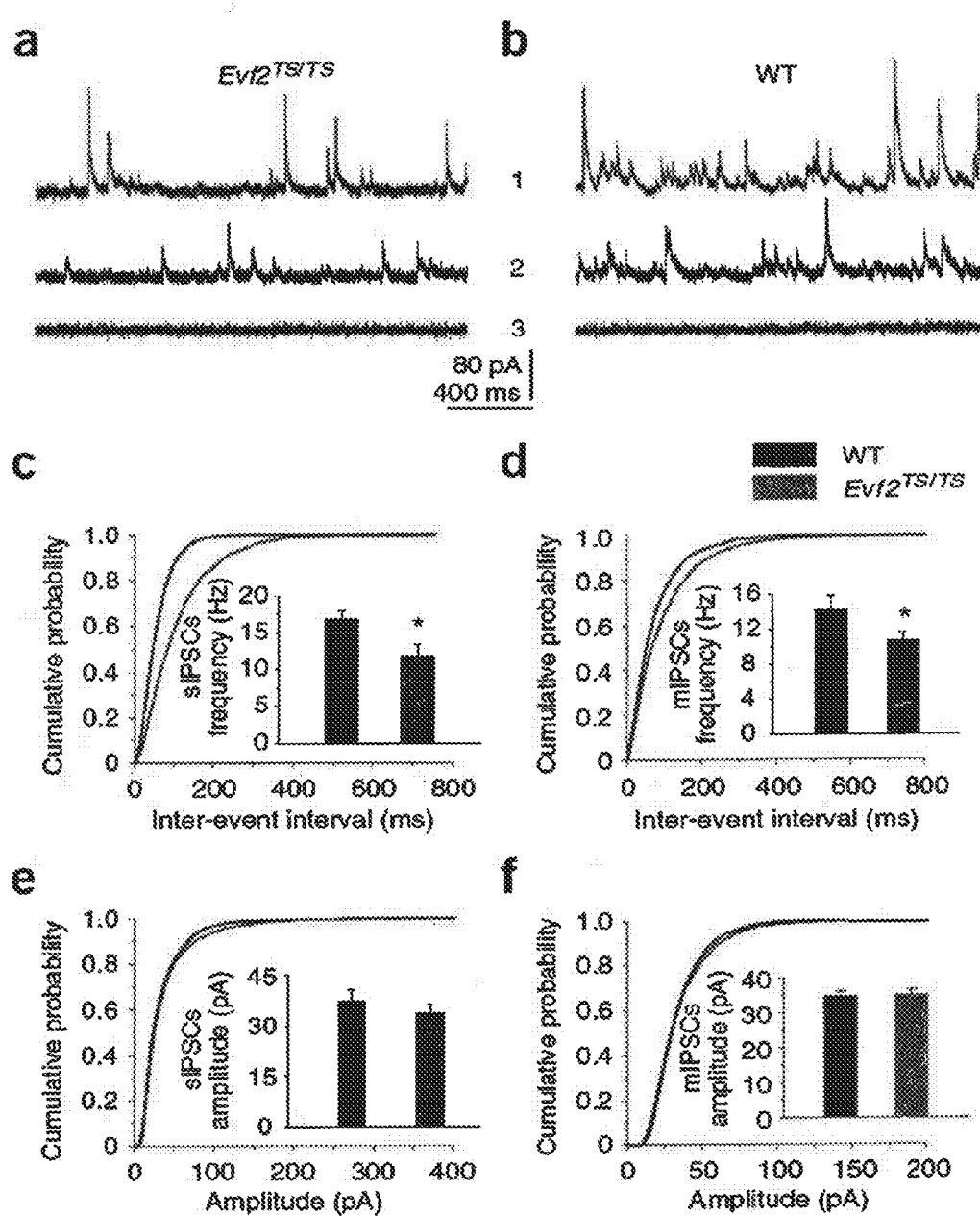
Figure 6G:
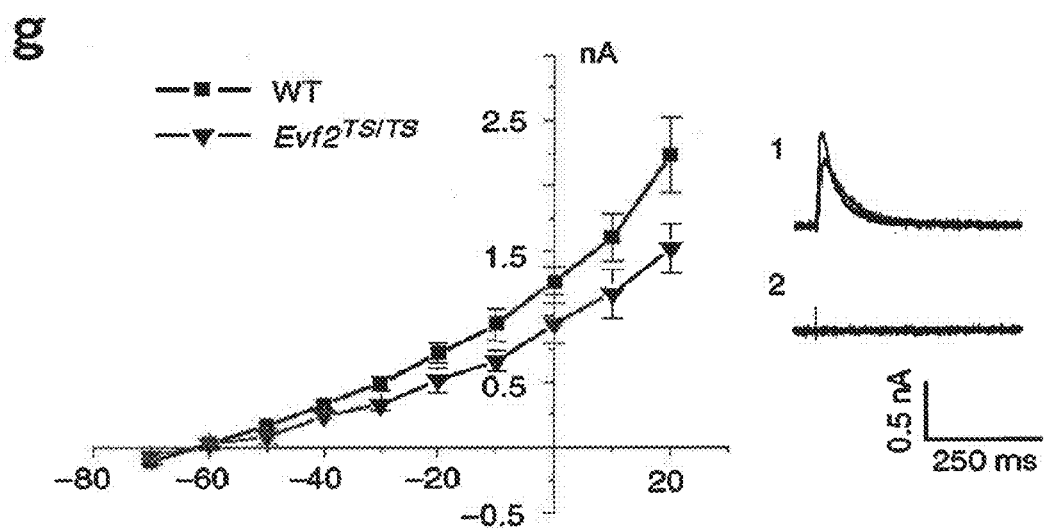

FIGS. 6a-6g provide an example of data showing that GABAergic synaptic inhibition is reduced in CA1 layer of the adult hippocampus of Evf2TS/TS mutant mice. FIGS. 6(a,b) provide representative traces of sIPSCs (1) and mIPSCs (2) from CA1 pyramidal cells of wild-type and Evf2TS/TS mice. Picrotoxin 0.25 mM blocked all IPSC activity in Evf2TS/TS and wild-type mice (3). FIGS. 6 (c,d) provide averaged cumulative probability plots of sIPSC and mIPSC inter-event intervals from CA1 pyramidal cells (Evf2TS/TS, red; wild-type, black; Kolmogorov-Smimov test, P<0.001). Insert, sIPSCs and mIPSCs event frequency in adult and old Evf2TS/TS mice was less (sIPSC adult, 11.75±1.73 Hz; sIPSC old, 9.17±0.71; mIPSCs adult, 10.65±1.05 Hz; mIPSCs old, 6.5±0.83 Hz) than in control wild-type mice (sIPSC adult, 16.66±1.26 Hz; sIPSC old, 12.62±0.92 Hz; mIPSCs adult, 14.16±1.67 Hz; mIPSCs old, 9.06±0.77 Hz). FIGS. 6(e,f) provide averaged cumulative probability plots of sIPSCs and mIPSCs amplitude (Evf2TS/TS, red; wild-type, black; sIPSC adult, 33.6±2.7 pA; sIPSC old, 48.50±3.06; mIPSCs adult, 35.26±1.41 pA; mIPSCs old, 34.87±3.76) and wild-type mice (sIPSC adult, 37.4±3.2 pA; sIPSC old, 53.78±3.98; mIPSCs adult, 34.54±1.64 pA; mIPSCs old, 37.03±4.63). FIG. 6(g) provides an I-V plot of evoked IPSCs of GABAergic inhibition in Evf2TS/TS mice (P<0.01, paired t test). IPSC current was normalized to the amplitude of evoked EPSC in ACSF containing no drugs to suppress excitatory synaptic activity. Trace 1 shows representative IPSCs recordings at +20 mV in Evf2TS/TS (red) and wild-type (black) mice (average n=5). Picrotoxin 0.25 mM blocked evoked IPSCs in CA1 neurons from both wild-type and Evf2TS/TS mice (trace 2). Error bars represent s.e.m. *P<0.05, t test.

Figure 7A:
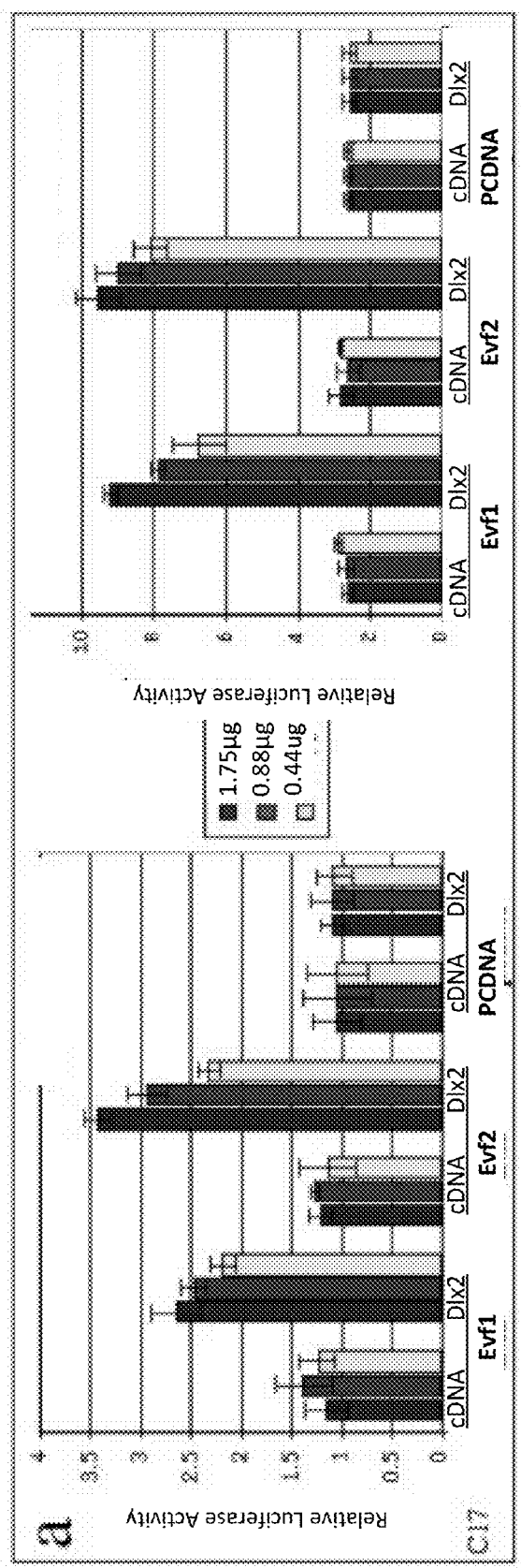
Figure 7B:
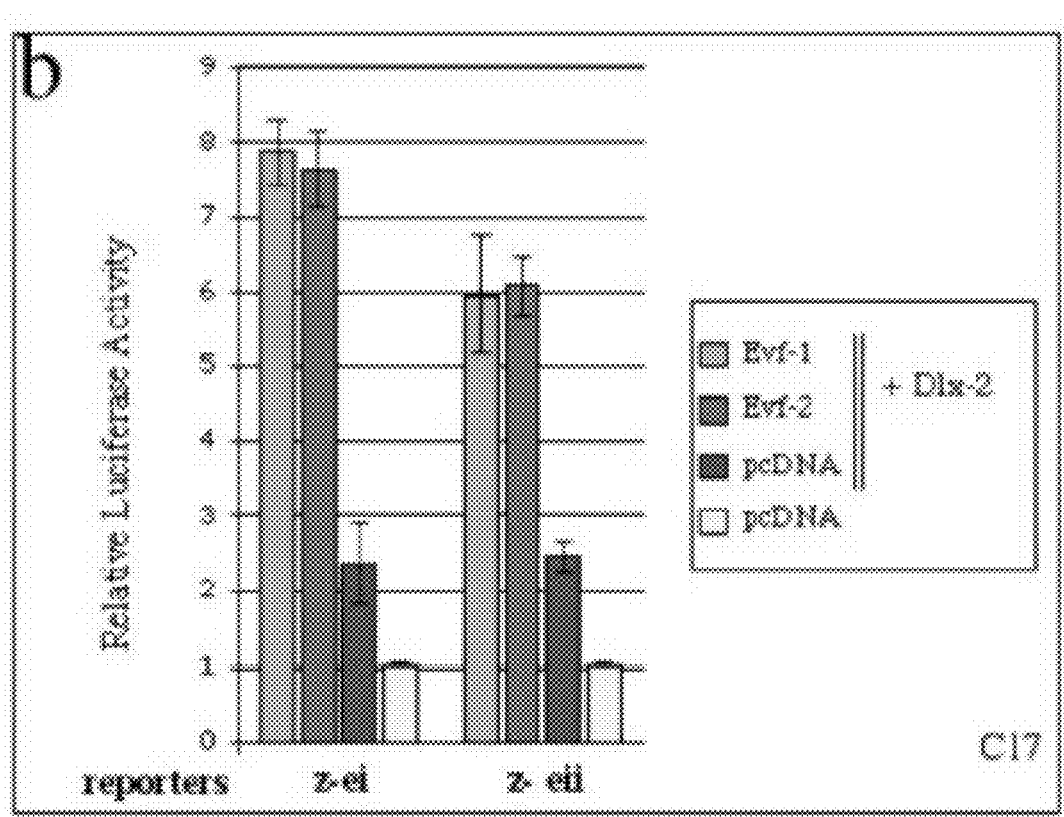
Figures 7C, 7D:
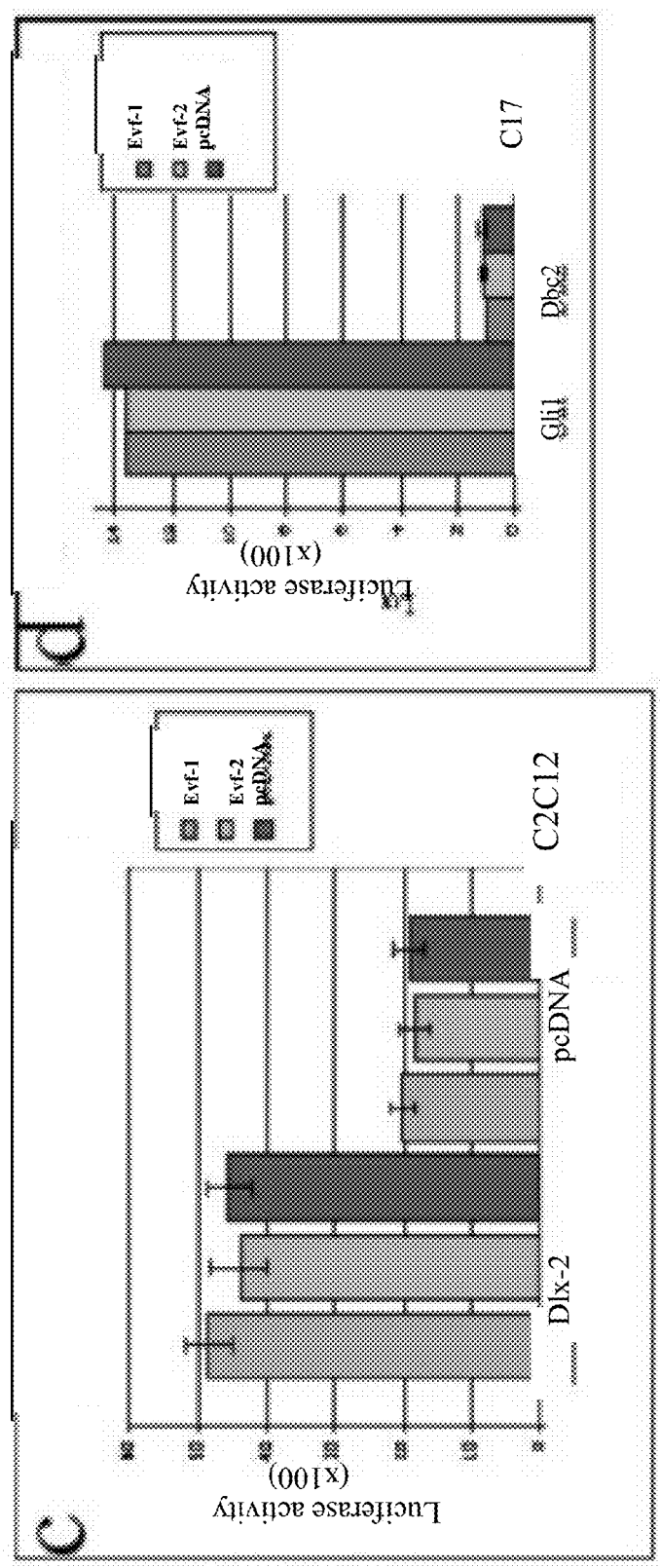
Figure 7E:
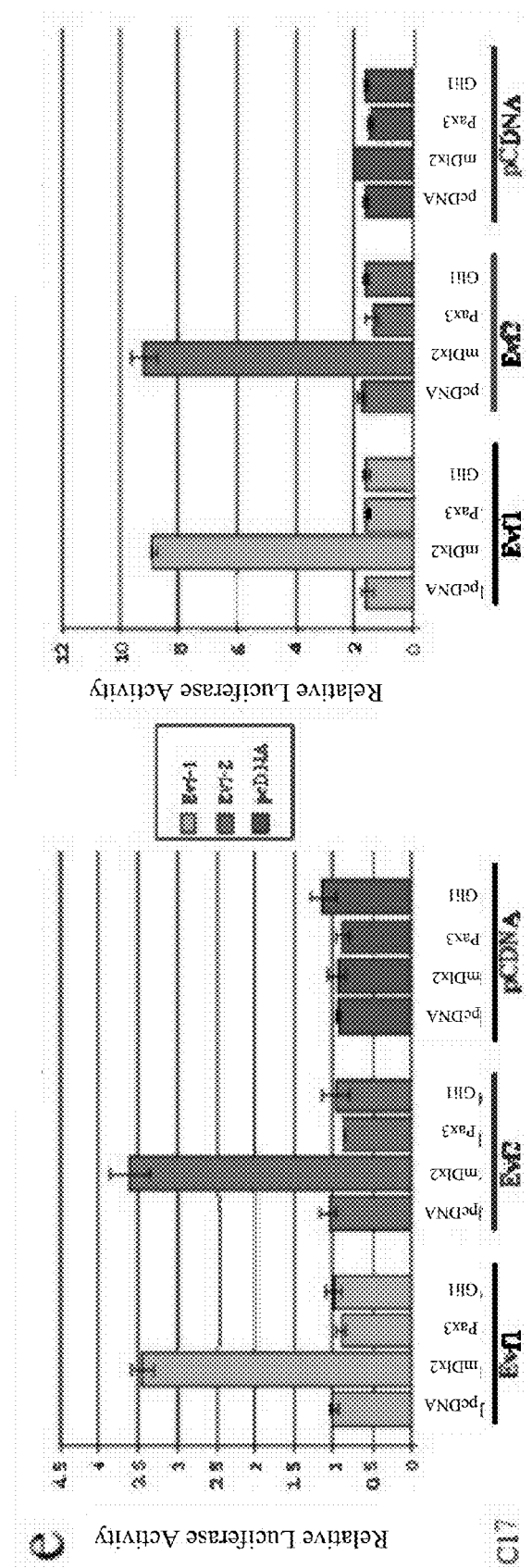
Figure 7F:
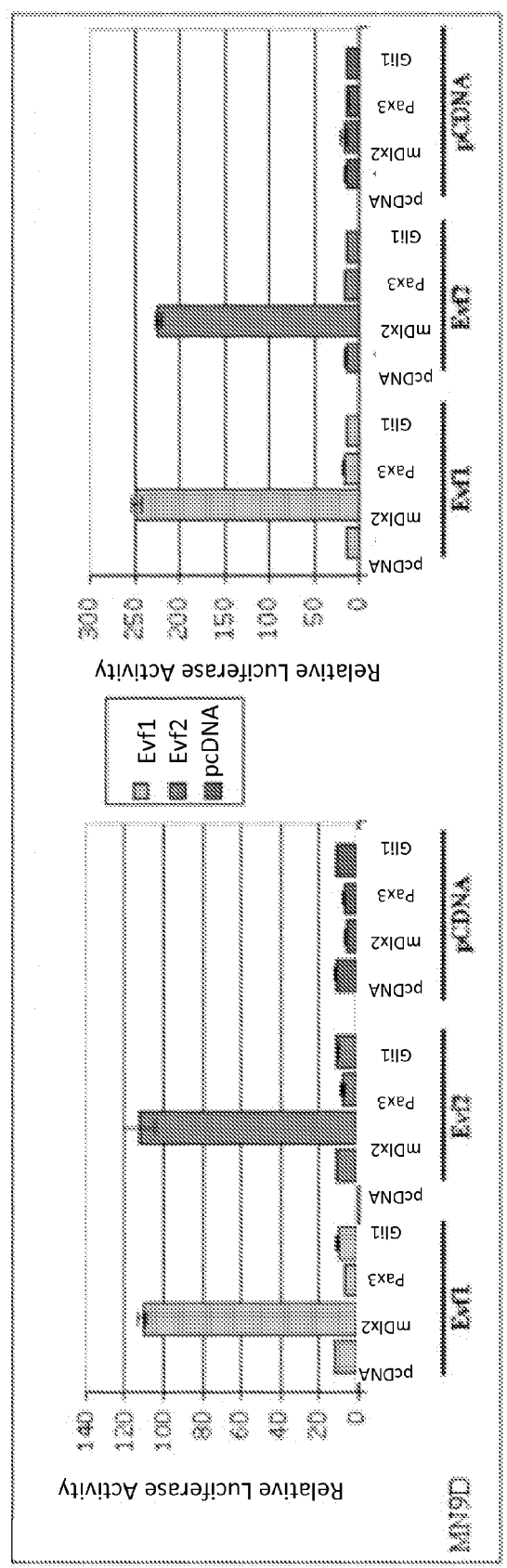
Figure 7G:
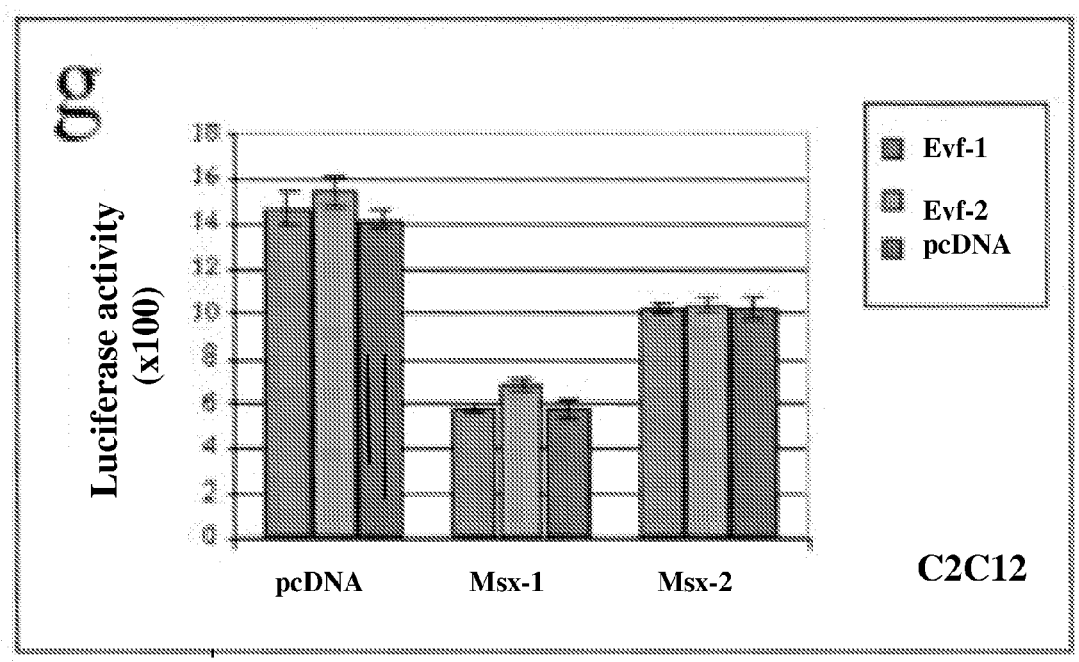
Figure 7H:
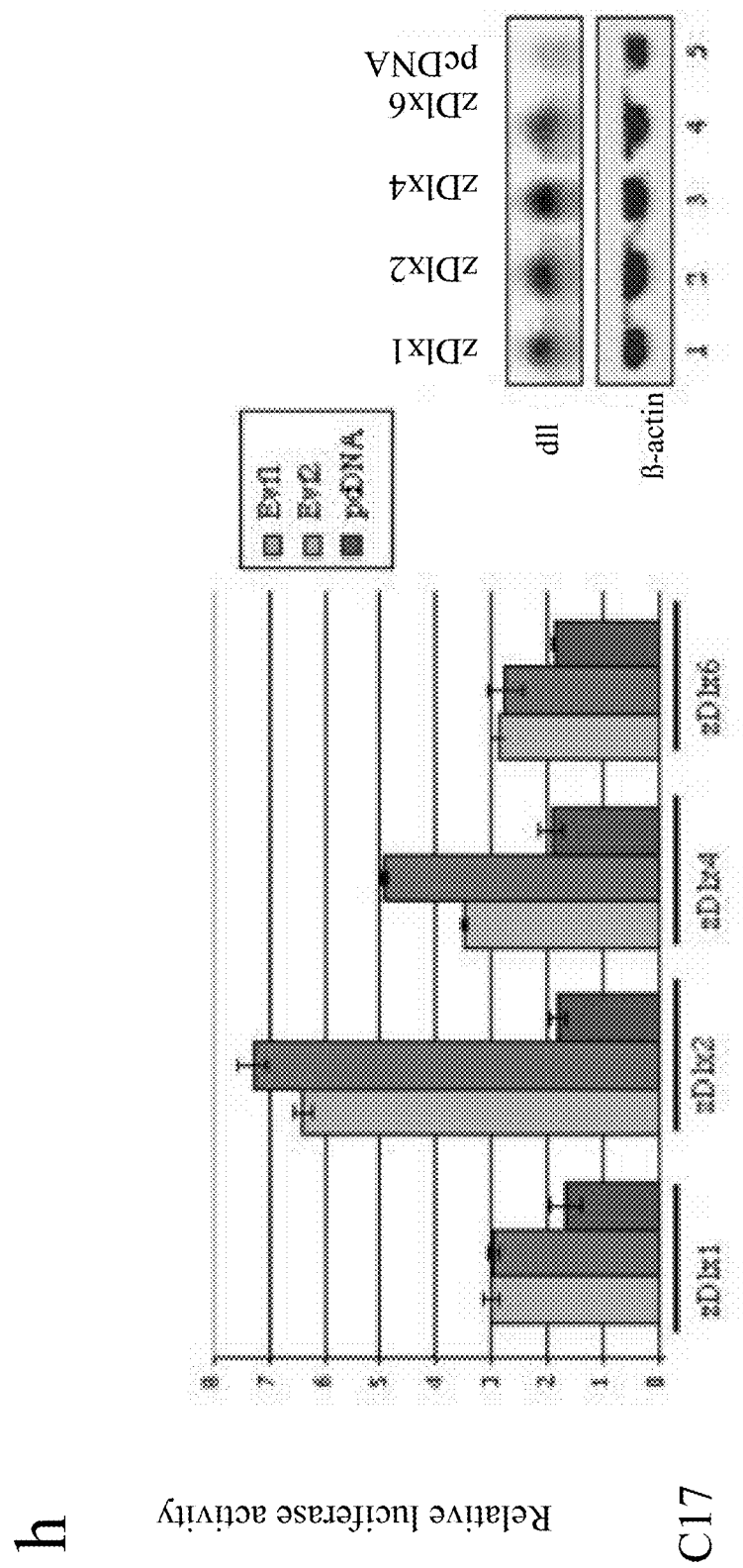
Figure 7I:
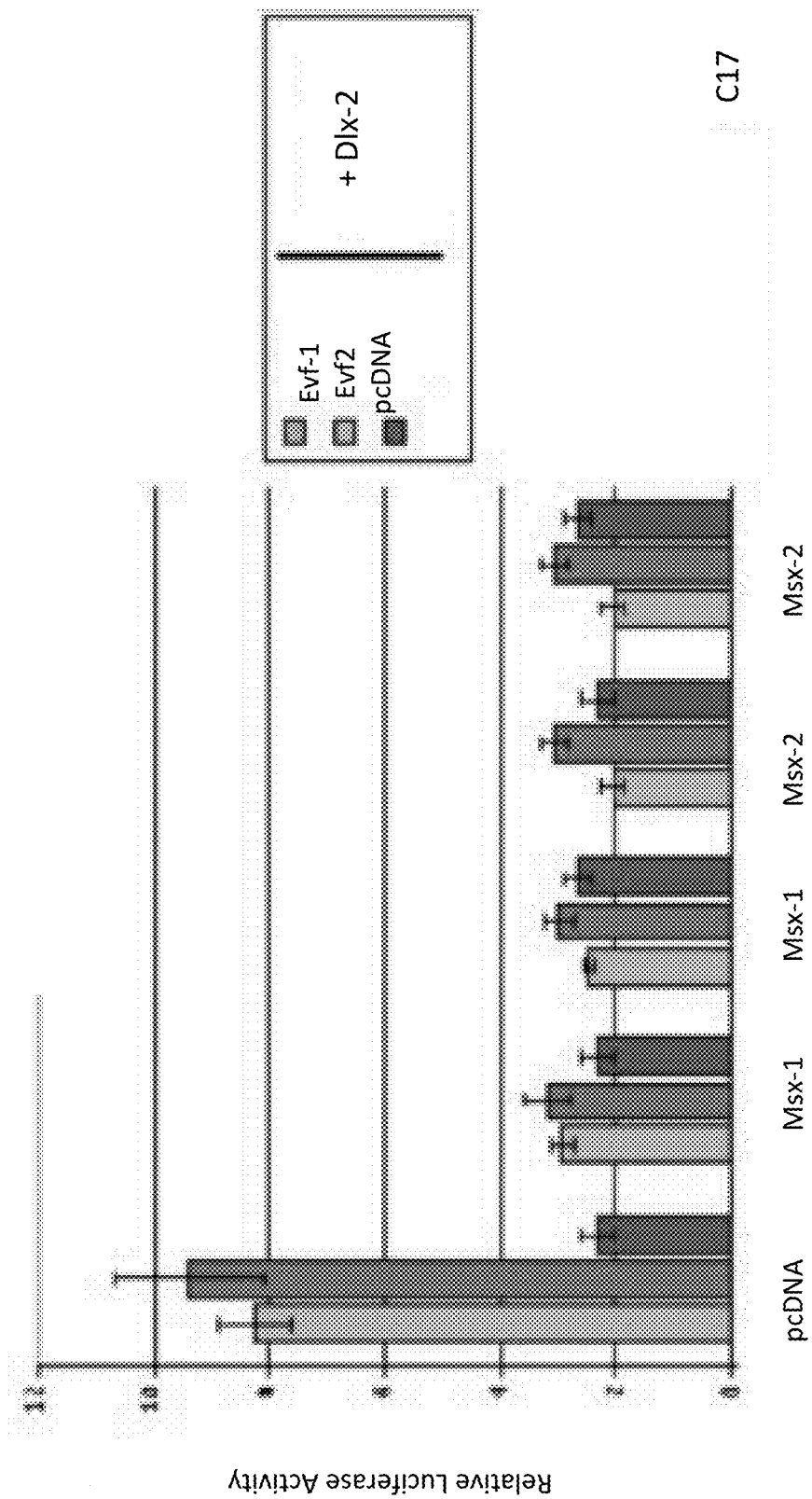
Figure 7J:
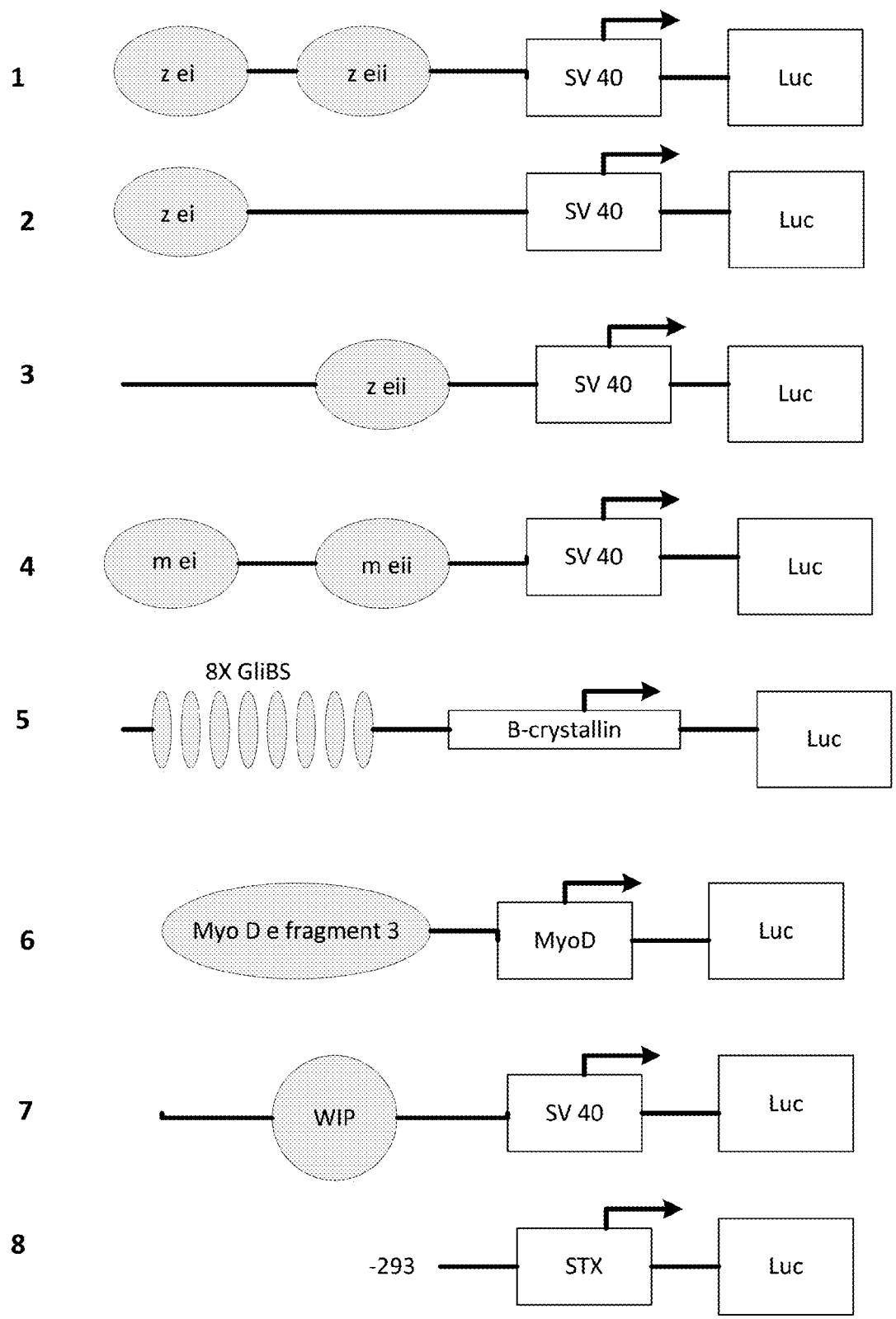

FIGS. 7a-7j provide some examples of data showing that Evf-1 and Evf-2 cooperate with Dlx family members to activate the Dlx 5/6 enhancer activity in a target-specific, homeodomain-specific, and cell-type specific manner. The CI7 and MN9D neural cell lines, or the C2C12 muscle cell line, as indicated, were transfected with pcDNA-containing constructs along with the different reporters as indicated (i). All experiments were performed a minimum of three times in triplicate. The different reporters listed in (i) 1-7 were used as targets to determine the specificity used for cooperative activation by Evf-1, Evf-2, and Dlx-2. Transfection efficiency was normalized by including a Renilla luciferase internal control plasmid. FIG. 7a provides an example of Evf-1 and Evf-2 induce dosage-dependent cooperative activation of the mouse Dlx 5/6 and zebrafish Dlx 4/6 enhancer constructs. 1.75 µg, 0.88 µg, or 0.44 µg of 1 g of Evf-2 was co-transfected with pcDNA-Dlx-2, along with different reporter constructs, Firefly and Renilla luciferase activities were determined, normalized and plotted on the y-axis. FIG. 7b provides an example of both ei and eii as targets of Evf transcription-enhancing activity. FIG. 7c shows that Evfs do not cooperate with Dlx-2 to increase the activation of the Wnt enhancer and d. Evfs do not cooperate with Gli-1 to increase the activation of the floor plate enhancer. FIG. 7e shows that Evfs do not cooperate with Pax3 or Gli-1 to activate Dlx 5/6 enhancer activity in C17 neural cells. FIG. 7f shows that Evfs cooperate with Dlx-2 but not with Pax-3 or Gli-1 to activate Dlx 5/6 enhancer activity in MN9D neural cells. FIG. 7g shows that Evfs do not cooperate with Msx-1 and Msx-2 to suppress the myoD enhancer in the muscle cell line C2C12. FIG. 7h shows that Dlx family members 1, 2, 4 and 6 exhibit cooperative activity with Evfs to different levels, Dlx2>Dlx4>Dlx6>Dlx1. Western analysis of transfected cell extracts probed with pan-anti-dll antibody is shown below. FIG. 7i shows that Evf-2 does not prevent inhibition by Msx-1 and Msx-2. FIG. 7j shows a summary of reporters used in FIGS. 7a-h. 1 shows zebrafish Dlx 4/6 enhancer i+ii Dlx-2 binding sites. 2 shows zebrafish Dlx 4/6 enhancer i Dlx-2 binding sites. 3 shows zebrafish Dlx 4/6 enhancer ii Dlx-2 binding sites. 4 shows mouse Dlx 5/6 enhancer i+ii Dlx-2 binding sites. 5 shows Floor plate enhancer Gli 1 binding sites. 6 shows MyoD enhancer. 7 shows Wnt1 enhancer. 8 shows STX minimal promoter Pax-3 binding site.

Figures 8A, 8B, 8C:
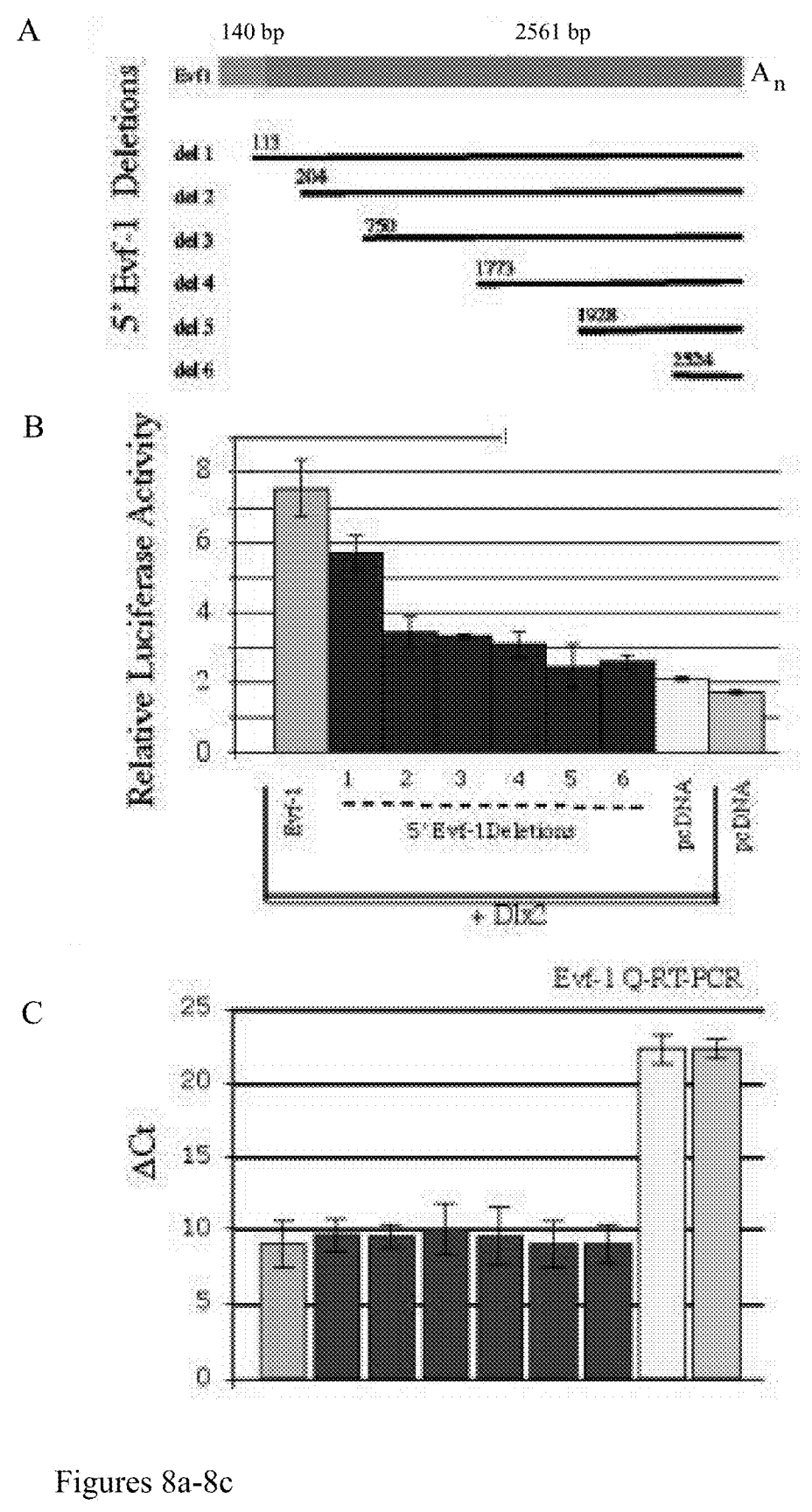
Figures 8D, 8E, 8F:
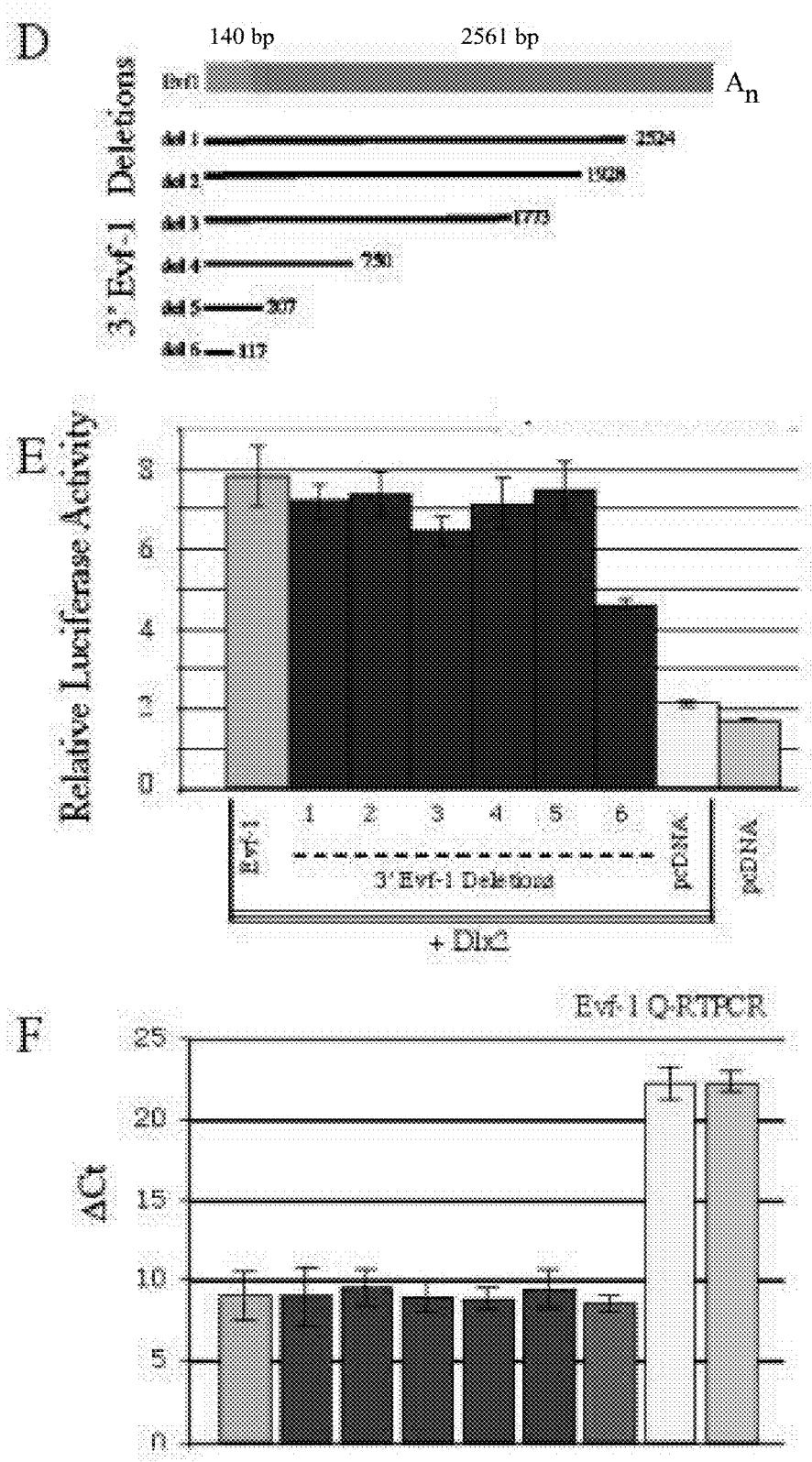
Figure 8G:
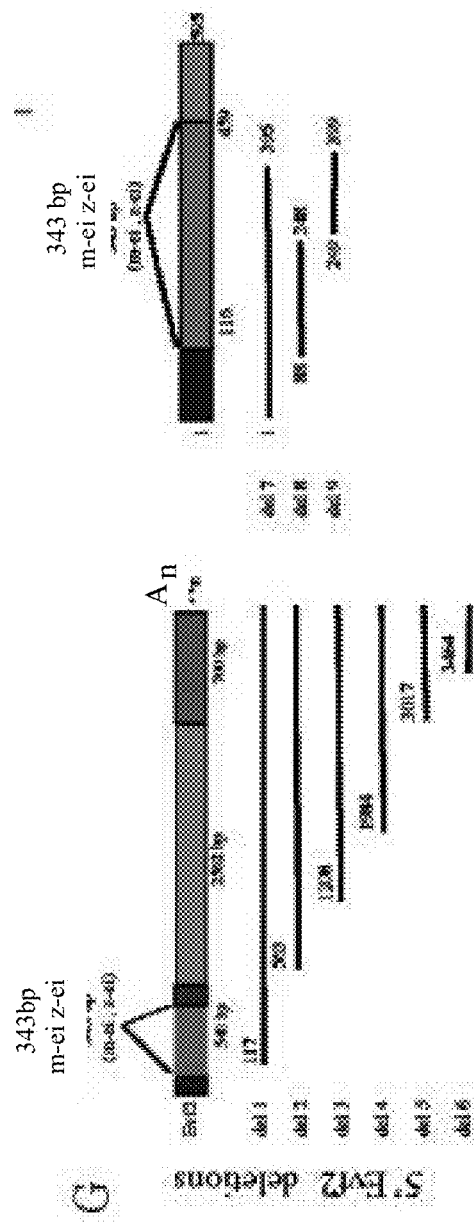
Figure 8H:
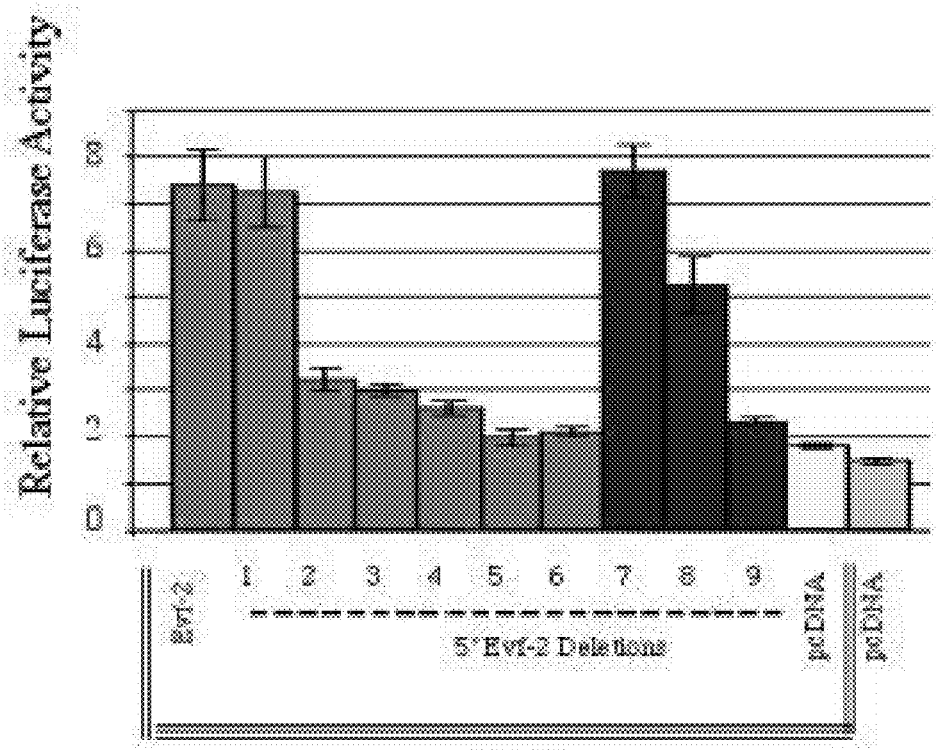
Figure 8I:
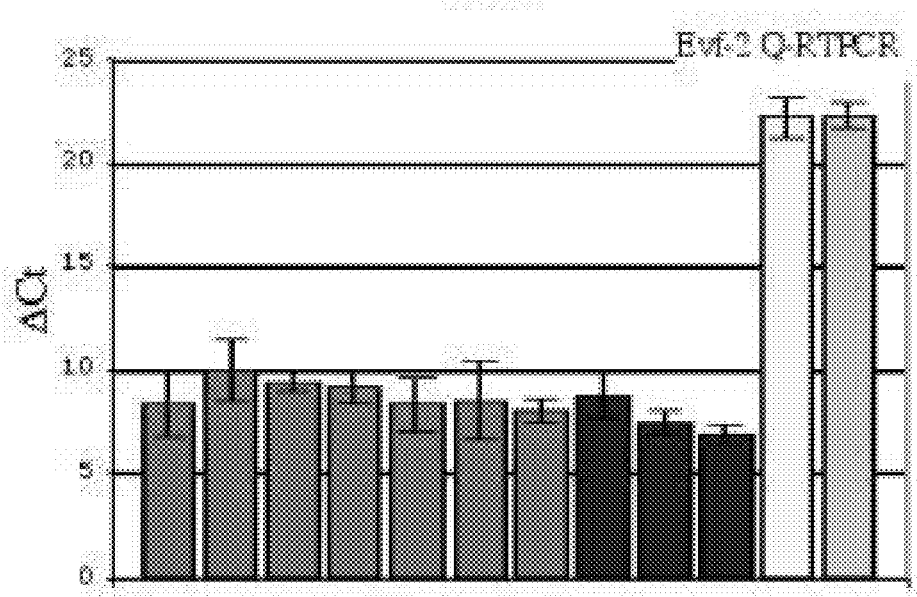
Figure 8J:
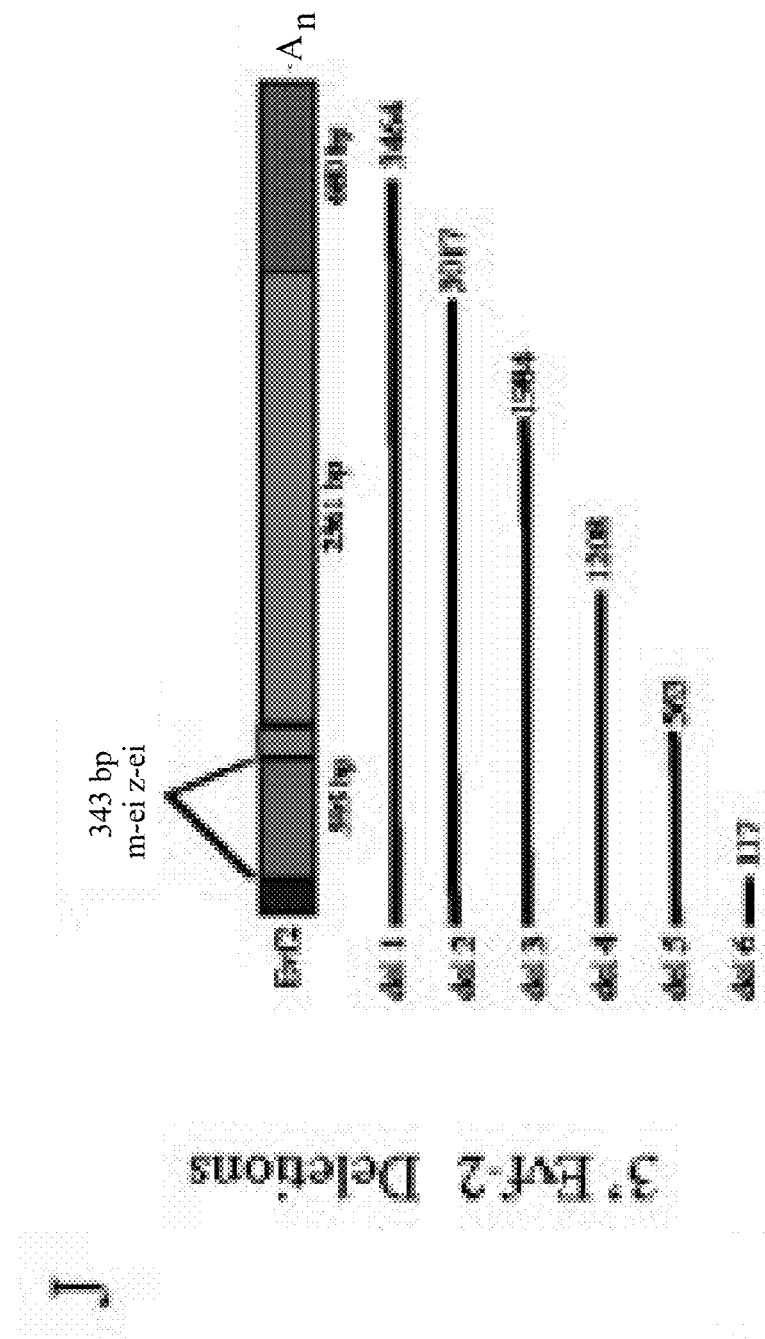
Figure 8K:
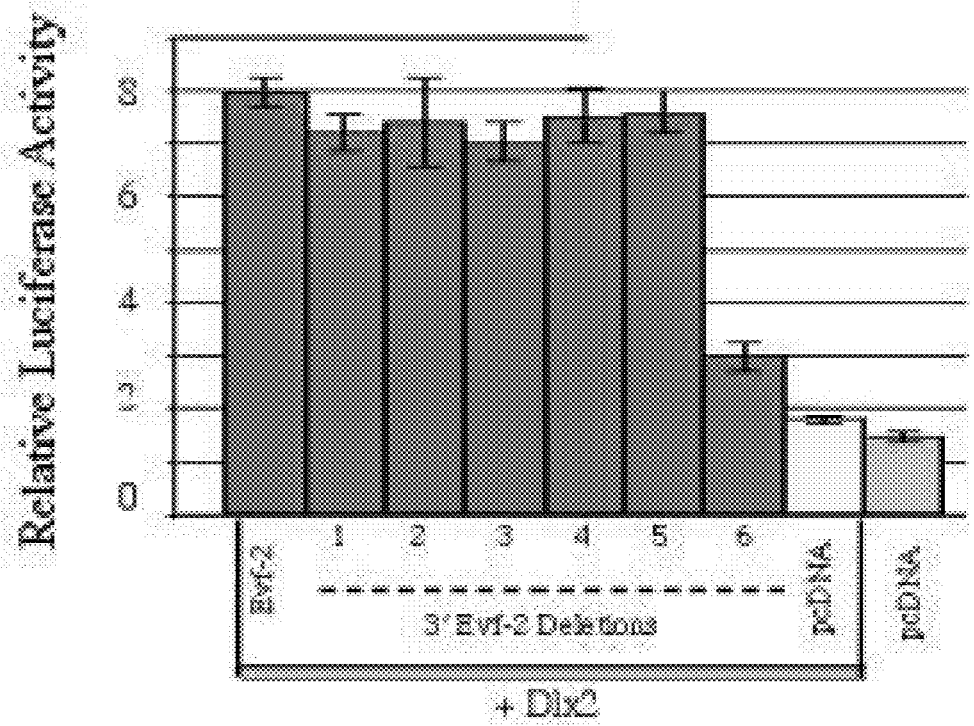
Figure 8L:
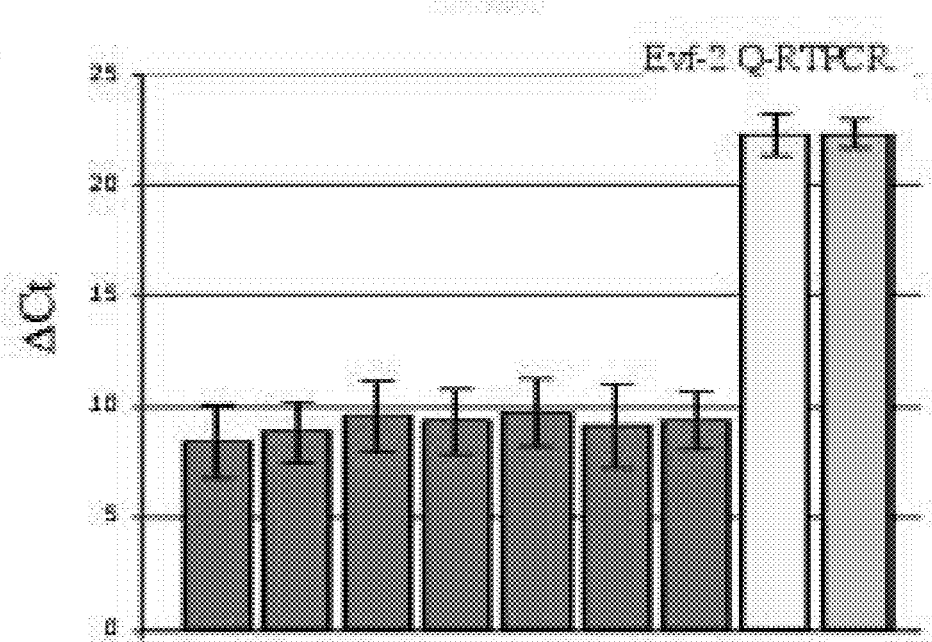

FIGS. 8A-8L provide some additional examples of data showing that Evf-1 and Evf-2 cooperate with Dlx family members to activate the Dlx 5/6 enhancer activity in a target-specific, homeodomain-specific, and cell-type specific manner. FIGS. 8A-L provide 5 prime unique regions of Evf-1 and Evf-2 are both necessary and sufficient for Dlx-2-dependent cooperative activation of the Dlx 5/6 enhancer. Comparison of Dlx 5/6 enhancer activation in C17 neural cell lines by different Evf-2 deletion mutants. FIGS. 8A, G provide a diagram of 5 prime Evf deletions. FIGS. 8B, 8H provide the activity of different 5 prime Evf deletions, FIGS. 8C, 8I provide quantitative RT-PCR of Evf deletions. FIGS. 8D, J provide a diagram of 3' Evf deletions. FIGS. 8E, 8K provide the activity of different 3 prime Evf deletions. FIGS. 8F, 8L provide quantitative RT-PCR of 3' Evf deletions. Quantitative RT-PCR analysis shows that 5- and 3-prime deletions are made in relatively similar amounts. Therefore, loss of function is not the result of Evf RNA degradation or destabilization.

Figure 9:
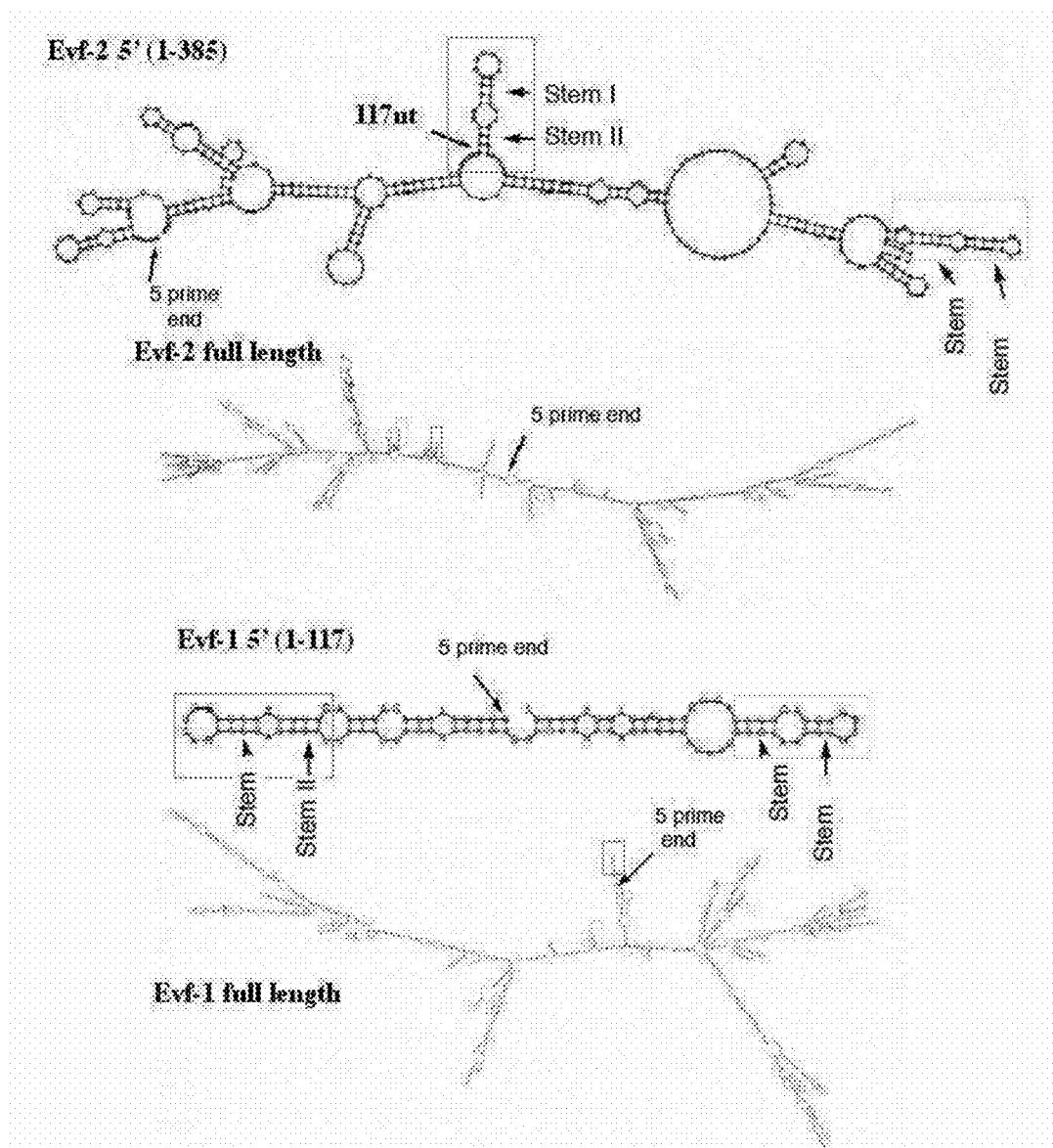

FIG. 9 provides a schematic representation of the secondary structure comparisons between the Evf-1 and Evf-2 transcription-regulating domains. Evf-1 and Evf-2 contain similar stem loop structures in their functional domains as well as in full length folded RNAs. These structures (highlighted by the red and green boxes) contain: red box structure: 6 nucleotide (nt) loop-4 base-pair (bp) stem I-{2nt (Evf-1) or 4 nt (Evf-2)bulge}-4 bp stem II, green box structure: 4 nt loop-3/5 bp stem IV-4/2 bp bulge-4/5 bp stem III. Therefore, despite the lack of sequence similarity, shared secondary structures may explain their similar transcriptional activities. Evf-2 5' (1-385) (SEQ ID NO: 51); Evf-2 full length (SEQ ID NO: 52); Evf-1 5' (1-117) (SEQ ID NO: 53); Evf-1 full length (SEQ ID NO: 54).

Figure 10A:
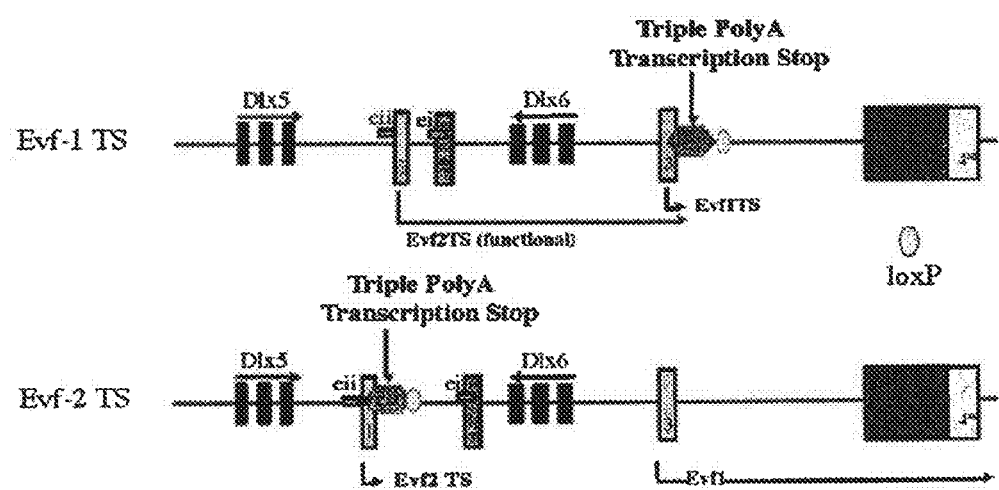
Figure 10B:
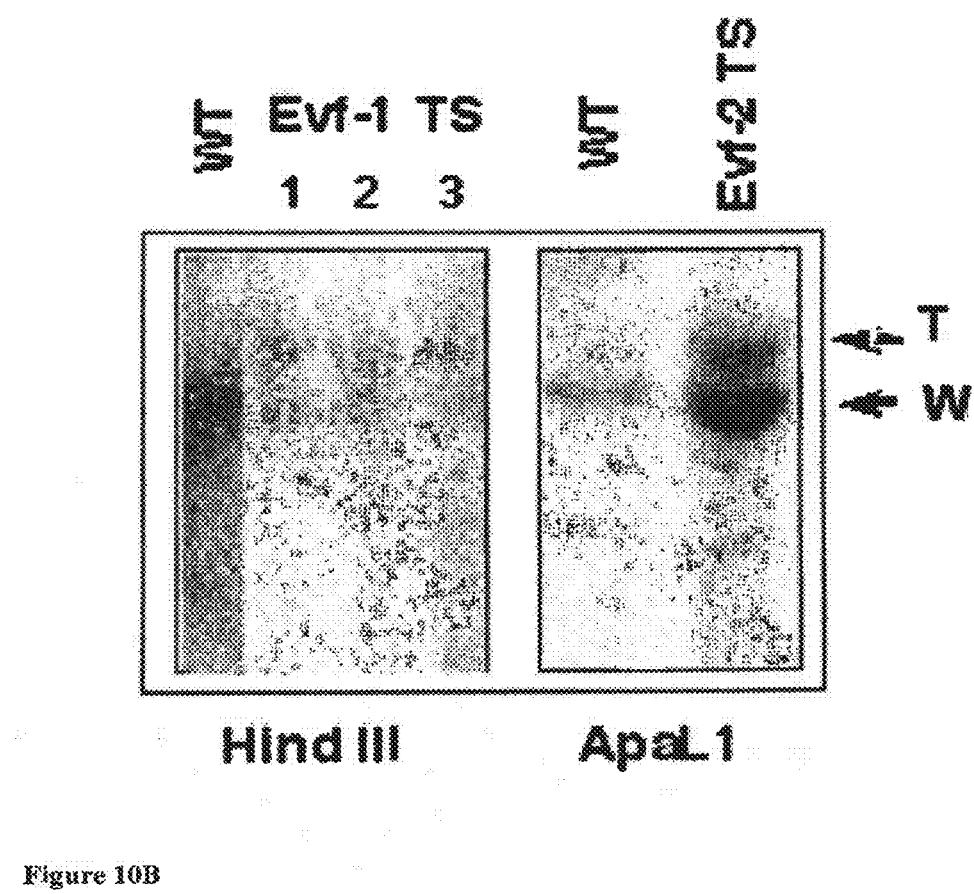

FIGS. 10A-10B. FIG. 10A provides a schematic example of one embodiment of transcription stop site insertions into the Evf-1 and Evf-2, 5' regions by homologous recombination in mouse ES cells. The triple polyA was inserted into exon 1 (Evf-2 TS) or exon 3 (Evf-1 TS) using reagents and protocols obtained from N. Copeland (BAC recombineering, Lee and Copeland, 2000). This prematurely stops endogenous transcription of Evf-2 and Evf-1 RNAs without disrupting enhancer regulatory sequences. Constructs were electroporated into ES cells. FIG. 10B: Southern hybridization shows that ES cells contain correctly targeted alleles. Blastocyst injections with Evf-2 TS and Evf-1 TS ES cells have generated several chimeric mice. Germline transmission for both have been verified by Southern analysis (not shown). After removal of the floxed neo by breeding with EIIAcre mice, one loxP and TS sequence (63 nucleotides) remain. Evf2 TS/TS and Evf1 TS/TS mice are fertile and live to at 1 year old. T, targeted, w, wt.

Figure 11:
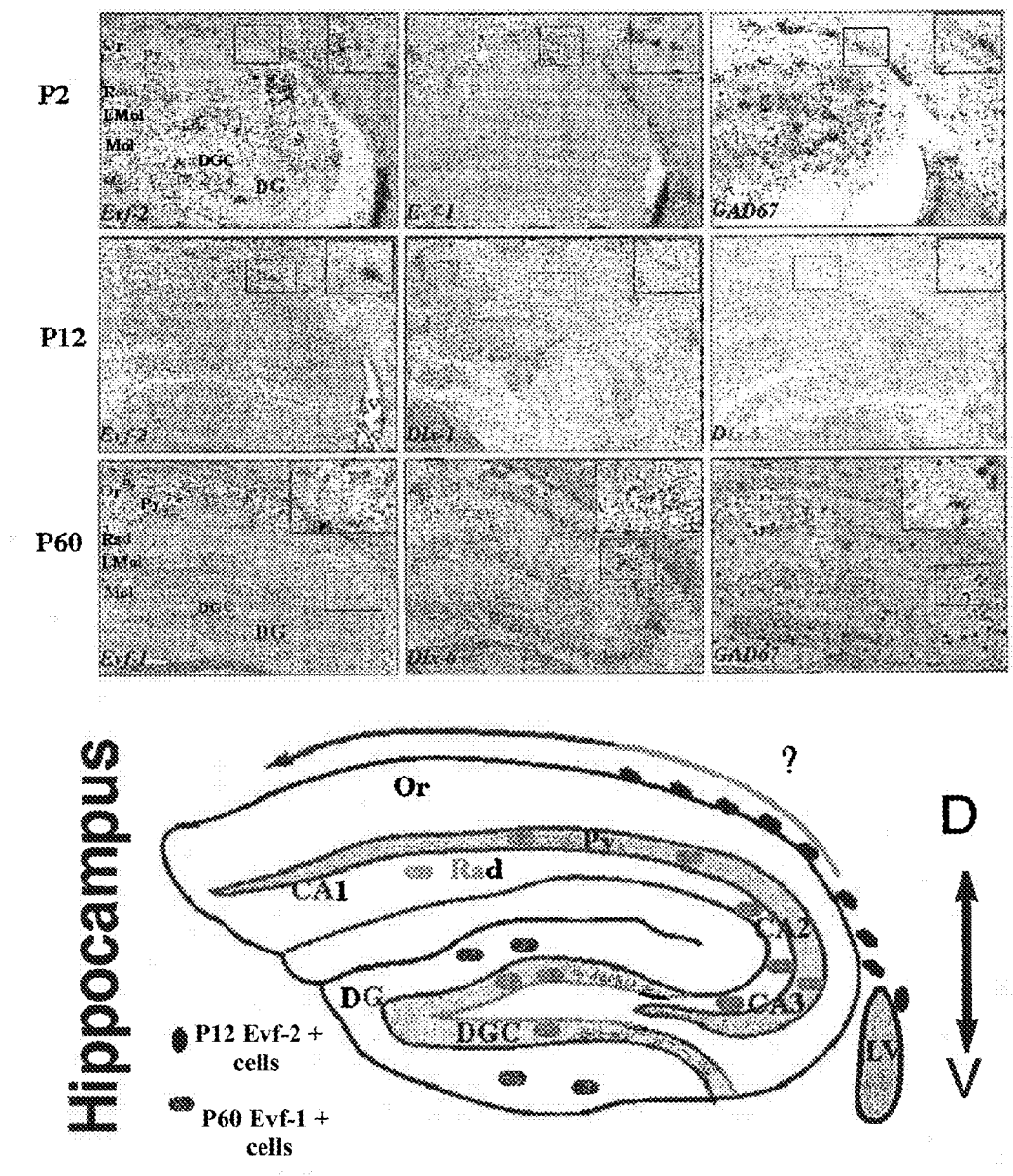

FIG. 11 provides data showing Evf-1 and Evf-2 expression diverge after birth in the hippocampus. RNA in situ hybridization shows that at P2, Evf-1 and Evf-2 expression are similar, with expression in the subventricular zone adjacent to the lateral ventricles, and cells migrating dorsally towards the corpus callosum. At P12, Evf-2 expression (dark blue cells) is similar to Dlx-1 and Dlx-5 expressing cells as they exit the subventricular zone and migrate along the external capsule towards the corpus callosum. Evf-1 and Dlx-6 expression is not detected in these migrating populations. By P60, however, Evf-1 and Dlx-6 are expressed in the hippocampus in distinct patterns. Evf-1 is found in the pyramidal and radiatum layers as well as throughout the dentate gyrus. Evf-2 is not detected in the P60 hippocampus of subventricular zone, Or, oriens, py, pyramidal, rad, radiatum, LMol, lacunosum molecular, Mol, DOC, dentate granule cell layer, LV, lateral ventricle, D, dorsal, V, ventral, P=postnatal day.

Figure 12:
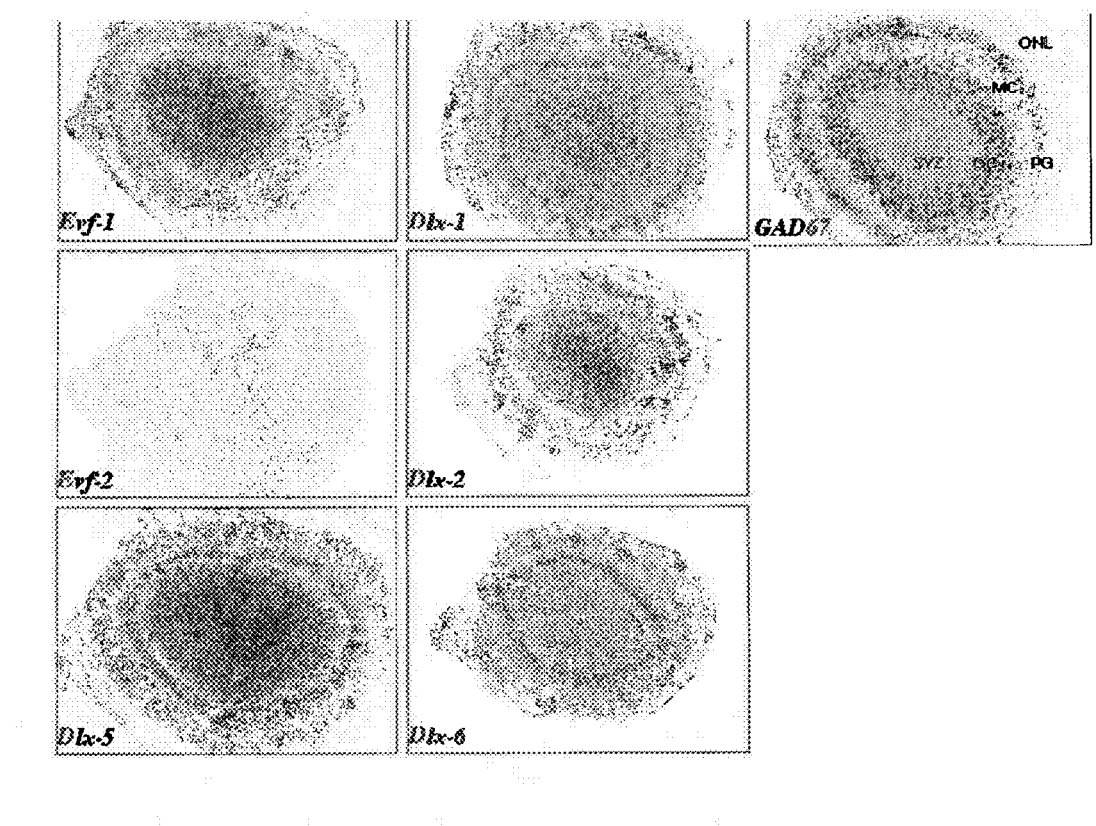

FIG. 12 provides data showing that Evf1, but not Evf2 is expressed in the mouse P2 olfactory bulb. Evf1 but not Evf2 is expressed in the SVZ overlapping with Dlx genes 1, 2, 5, and 6 in the P2 olfactory bulb. Subventricular zone, SVZ, granule cell layer, GC, mitral cell layer, MC, periglomerular layer, PO, outer nerve layer, ONL.

Figure 13:
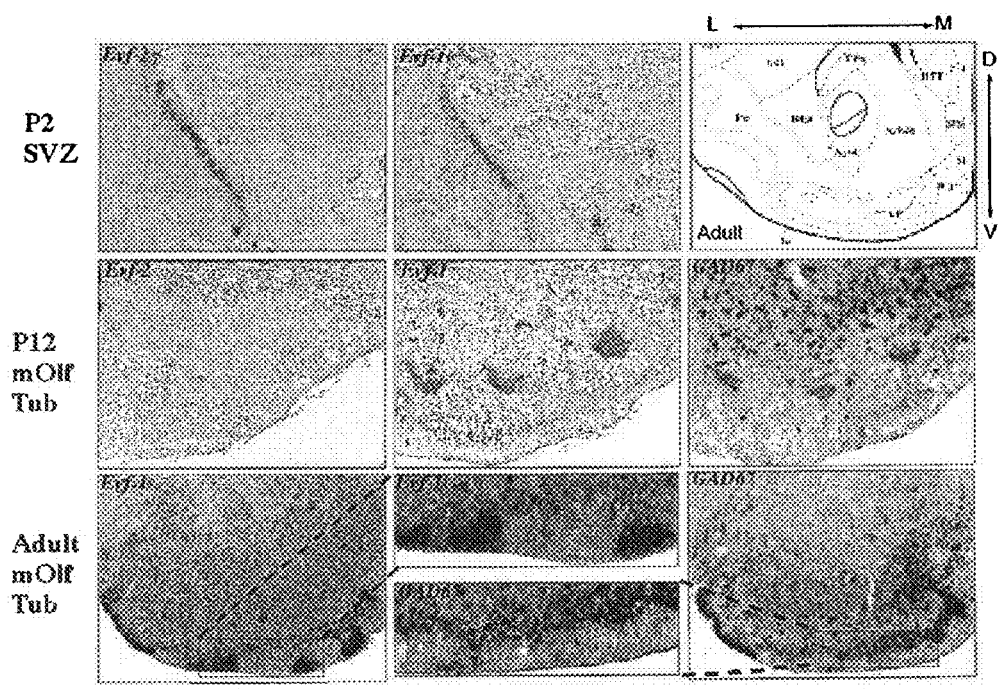

FIG. 13 provides an example of data showing Evf1 and 2 are expressed in the postnatal subventricluar zone, but only Evf1 expression persists in P12 and adult medial olfactory tubercle. RNA in situ hybridization of post-natal day 2 (P2, striatal SVZ), day 12 (P12) or adult using anti-sense RNAs as labeled. Upper right panel is from Paxinos (Mouse Atlas). L, lateral, M, medial, D, dorsal, V, ventral, SVZ, subventricular zone, mOlfTub, medial olfactory tubercle, GAD67, glutamate decarboxylase isoform 67.

Figures 14A, 14B, 14C, 14D, 14E, 14F, 14G, 14H:
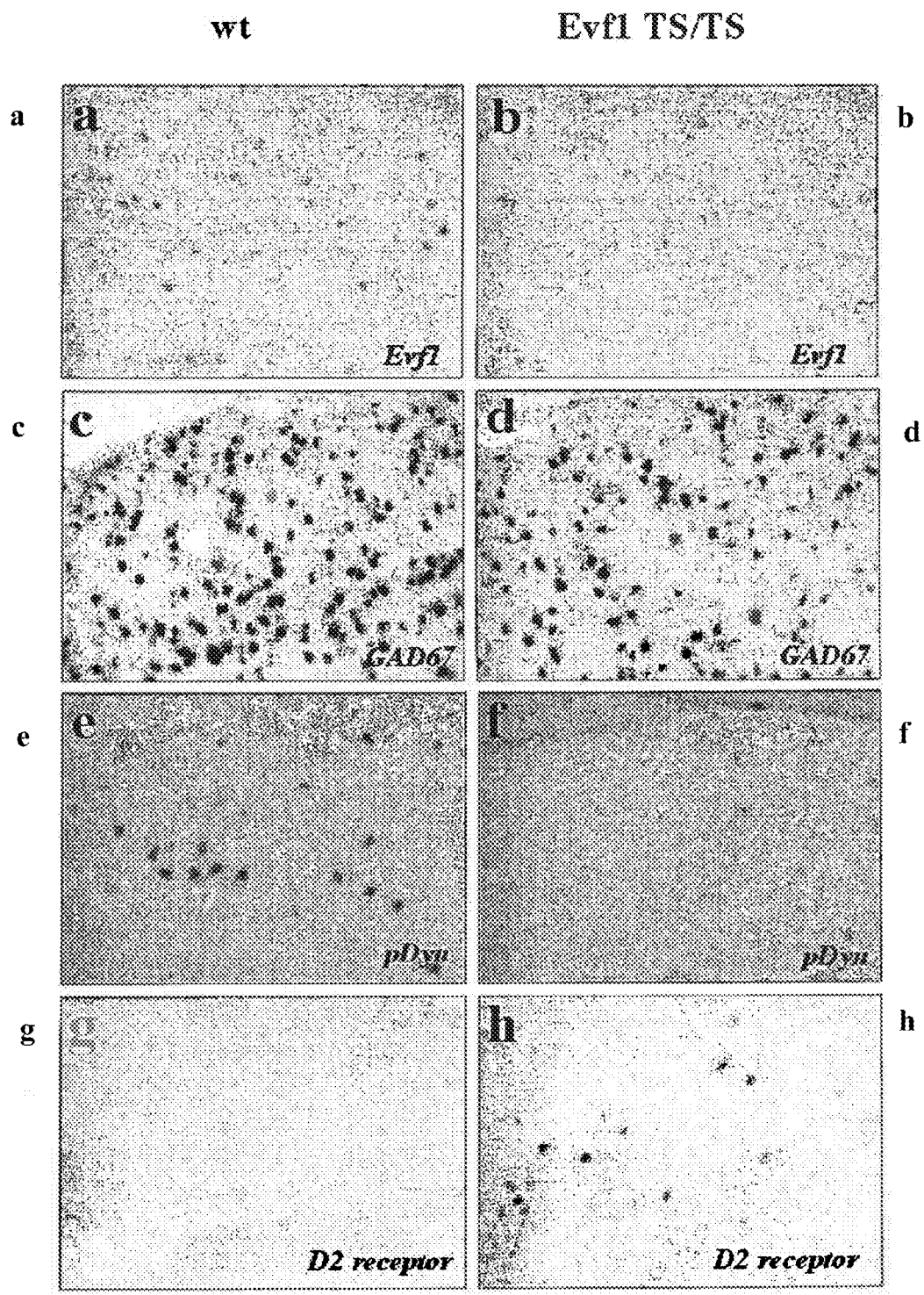
Figure 14I:
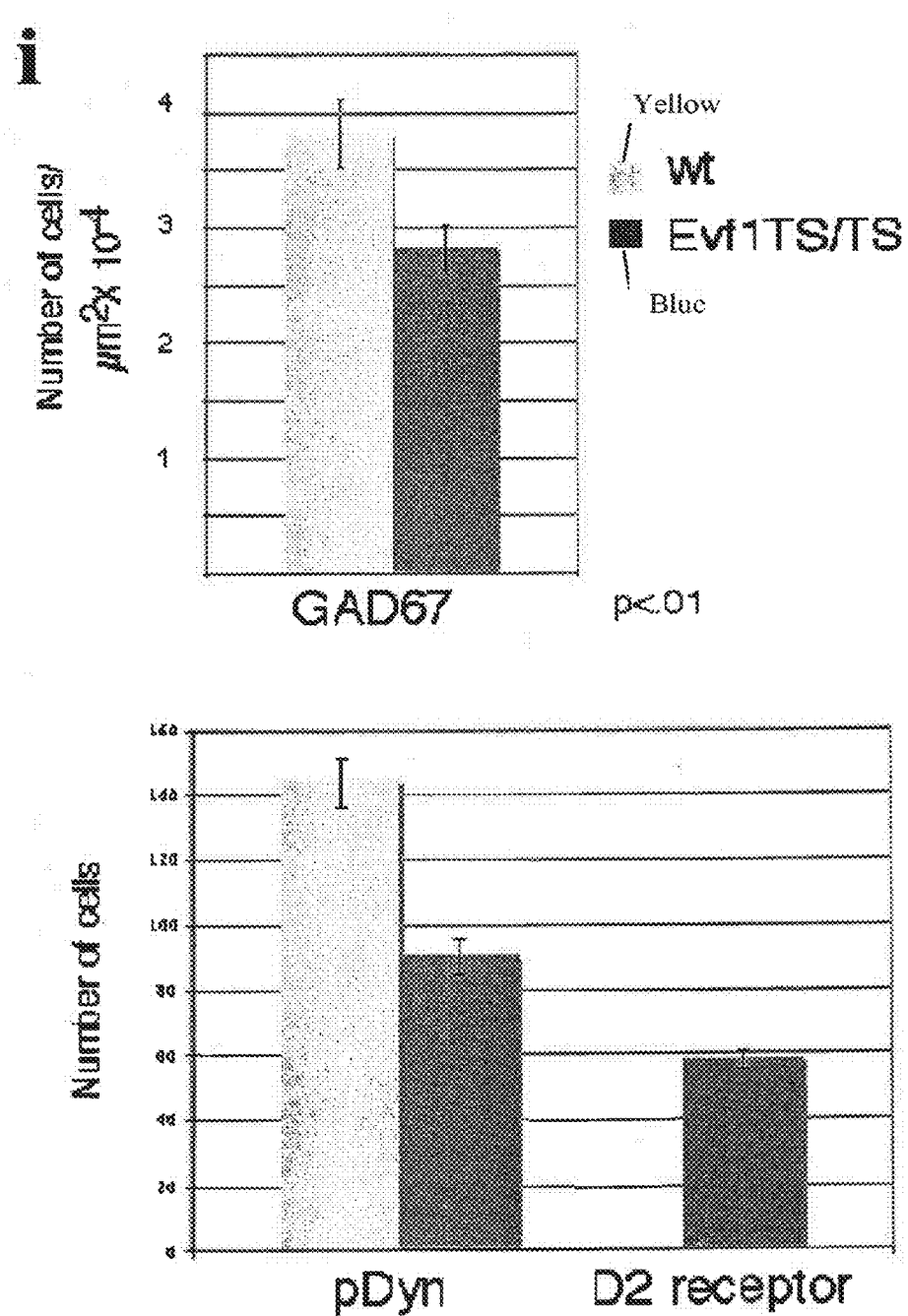

FIGS. 14a-14i provide an example of data showing decreased GABAergic interneurons, decreased numbers of pDyn expressing cells and increased numbers of D2 receptor expressing cells in the adult pre-frontal cortex of Evf1 TS/TS mutants. FIGS. 14a-h provide RNA in situ hybridization on postnatal day 60 coronal sections from Evf1 TS/TS mutants compared to wildtype littermate controls (wt) using Evf1, GAD67, pDyn and D2 receptor probes. FIG. 14i provides quantitation of the numbers of GAD67 expressing interneurons, pDyn and D2 receptor expressing cells in prefrontal cortex 60 days after birth. wt (yellow) Evf1 TS/TS (blue).

Figure 15:
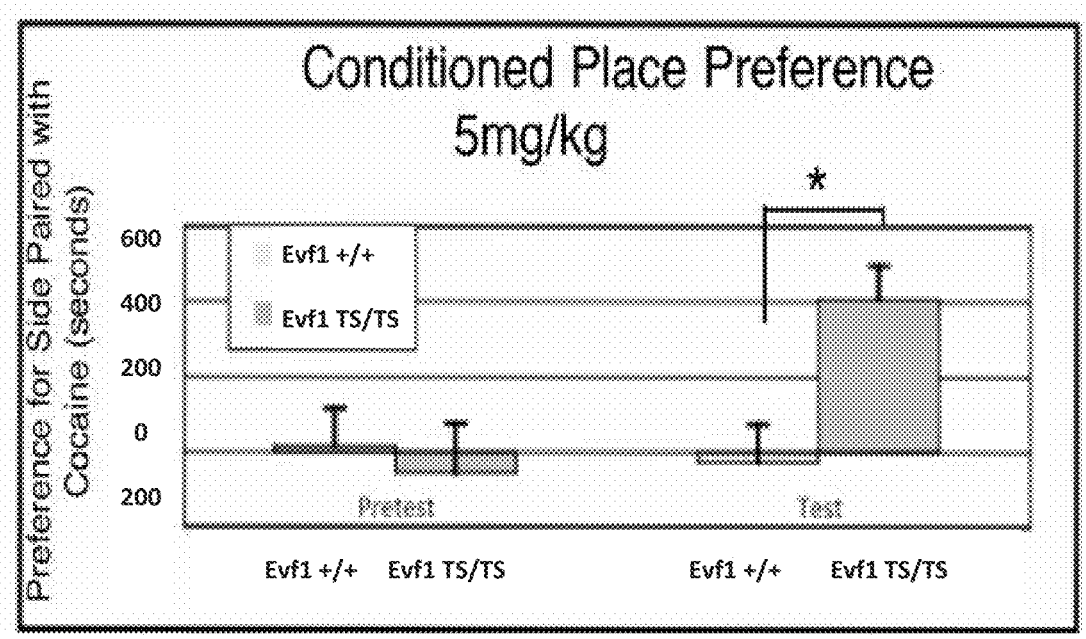

FIG. 15 provides an example of data showing Evf1 TS/TS mutants spend more time than wild-type littermates (Evf1+/+) in the chamber where cocaine is administered. An unbiased conditioned place preference assay using 5 mg/kg cocaine in one chamber and saline in a second chamber compares time spent seeking cocaine. In the pretest situation, mice, regardless of genotype, do not show a preference for the cocaine side. After 4 days alternating cocaine and saline, Evf1 TS/TS mutants (blue) display a preference for cocaine on the test day compared to wild-type littermate controls, Evf1+/+(yellow). n=5 for each genotype, * p=0.023.

Figure 16:
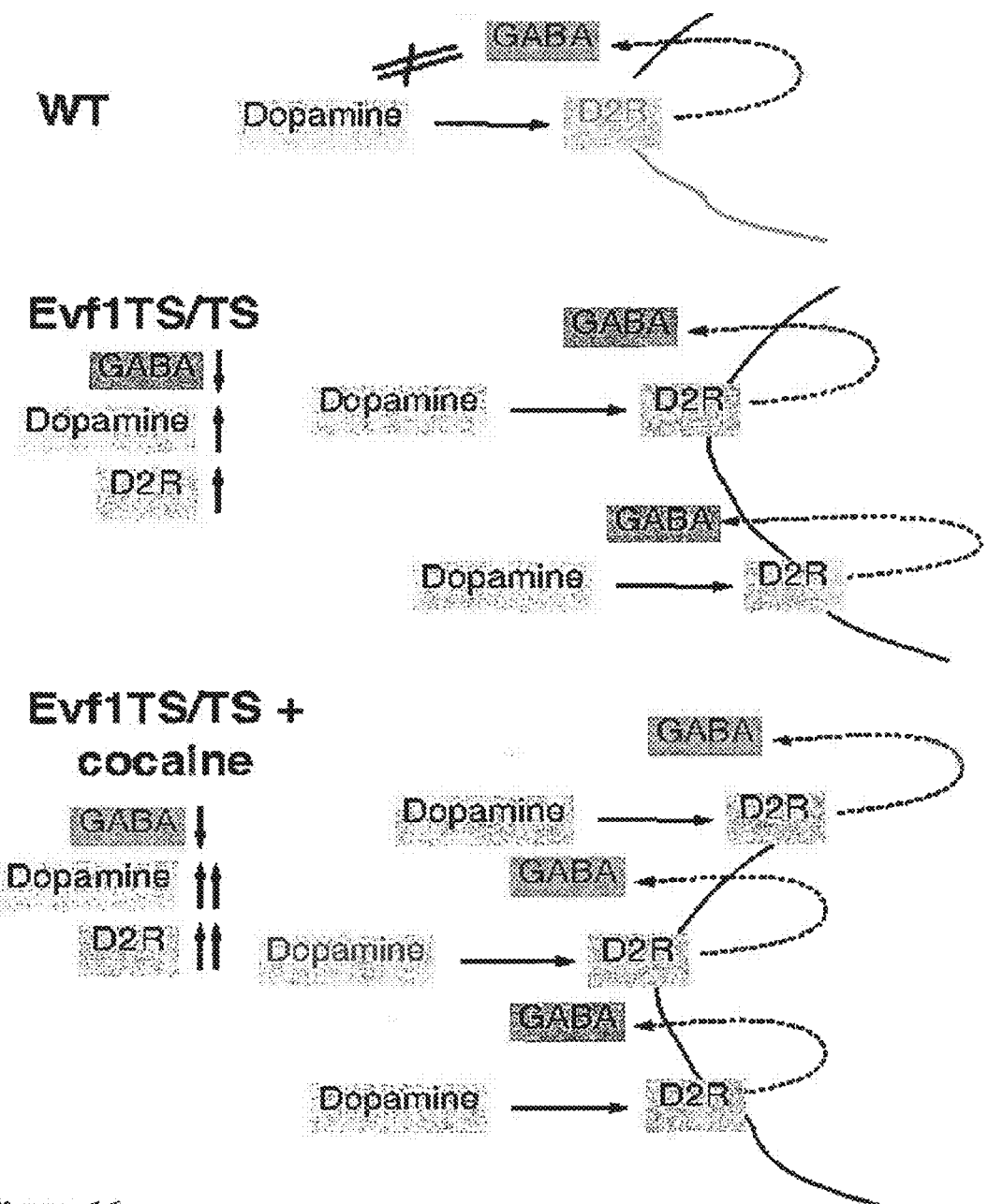

FIG. 16 provides a model of GABAergic interneuron response to cocaine in Evf1 TS/TS prefrontal cortex. PFC GABAergic interneurons have been shown to express D2 family receptors (Mrzljak et al., 1996). Dopamine binding to D2 receptors results in GABA release, increasing inhibition of firing by pyramidal neurons (Bunney and Aghajanian, 1976). GABA can reduce dopamine release (Dewey et al. 1992), thus providing a self-regulatory mechanism. In Evf1 TS/TS mice, PFC GABAergic interneuron numbers are reduced (FIG. 14), lowering GABA levels. This results in increased levels of dopamine and increased expression of D2R's in a subpopulation of interneurons. However, it is unlikely that increased GABA release from this subpopulation of PFC interneurons is sufficient to overcome the loss of GABAergic interneurons observed in the Evf1 TS/TS PFC. Therefore, it is proposed that the Evf1 TS/TS PFC contains higher levels of extracellular dopamine resulting from reduced GABA. By preventing re-uptake of dopamine, cocaine treatment would further increase extracellular dopamine concentrations in Evf1 TS/TS compared to wt control mice. This model predicts that the concentration of cocaine required for an acute response or to elicit cocaine conditioned preference will be lower in Evf1 TS/TS mice than in wt controls. This is in accordance with Dewey et al. (1997), who reported that the GABA agonist GVG, administered 3 hours prior to cocaine, can attenuate locomotor response. Preliminary data shown in FIG. 17 support that Evf1 TS/TS mutants show an increased preference for the cocaine chamber in the CPP assay.

Figure 17:
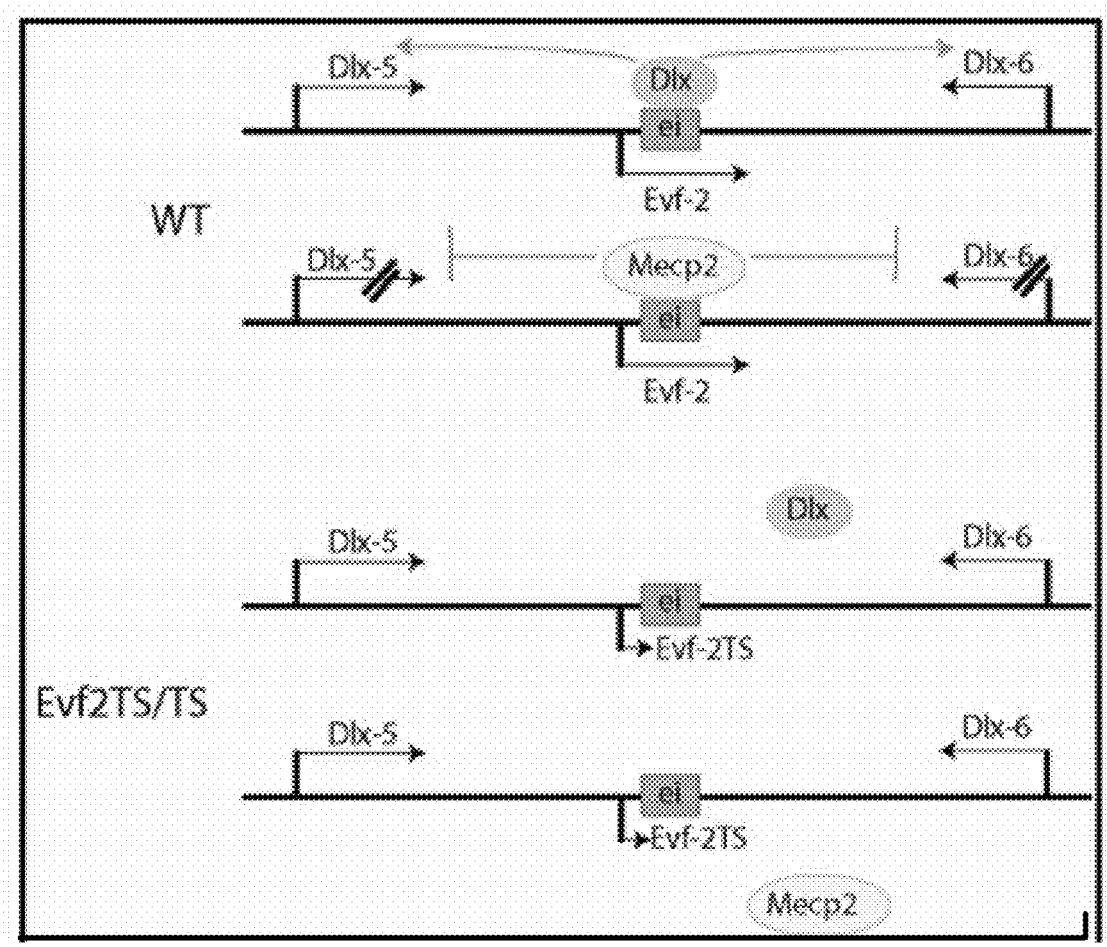

FIG. 17 provides another model for Evf2-dependent recruitment of Dlx and Mecp2 to Dlx 5/6 enhancer ei. CHIP data show that in wildtype E13.5 MGE, ei and eii are bound by Dlx proteins. For simplicity, only ei sites are depicted in this model. While different mechanisms are possible, the model proposes that one allele is bound by Dlx, while the other ei copy is bound by Mecp2. Mecp2 null mice exhibit increased Dlx'5 and 6 expression, supporting the idea that Mecp2 bound to ei suppresses Dlx5 expression (Horike et al. 2005). In Evf2 TS/TS mutants, Dlx5 and Dlx6 are both upregulated, similar to that found in Mecp2 null analysis. CHIP experiments show that loss of Evf2 results in the loss of Dlx recruitment to ei. The model proposes that premature termination of Evf2 (TS) prevents Dlx recruitment to ei on one allele and Mecp2 recruitment to the other ei allele. This model suggests the following: 1. The Evf2 RNA regulates enhancer activity through recruitment of positive and negative transcriptional regulators. 2. Dlx proteins promote Dlx 5/6 ei and eii regulated transcription by preventing Mecp2 binding. 3. Mecp2 represses Dlx 5/6 gene expression by preventing Dlx transcription factor binding.

Figure 18:
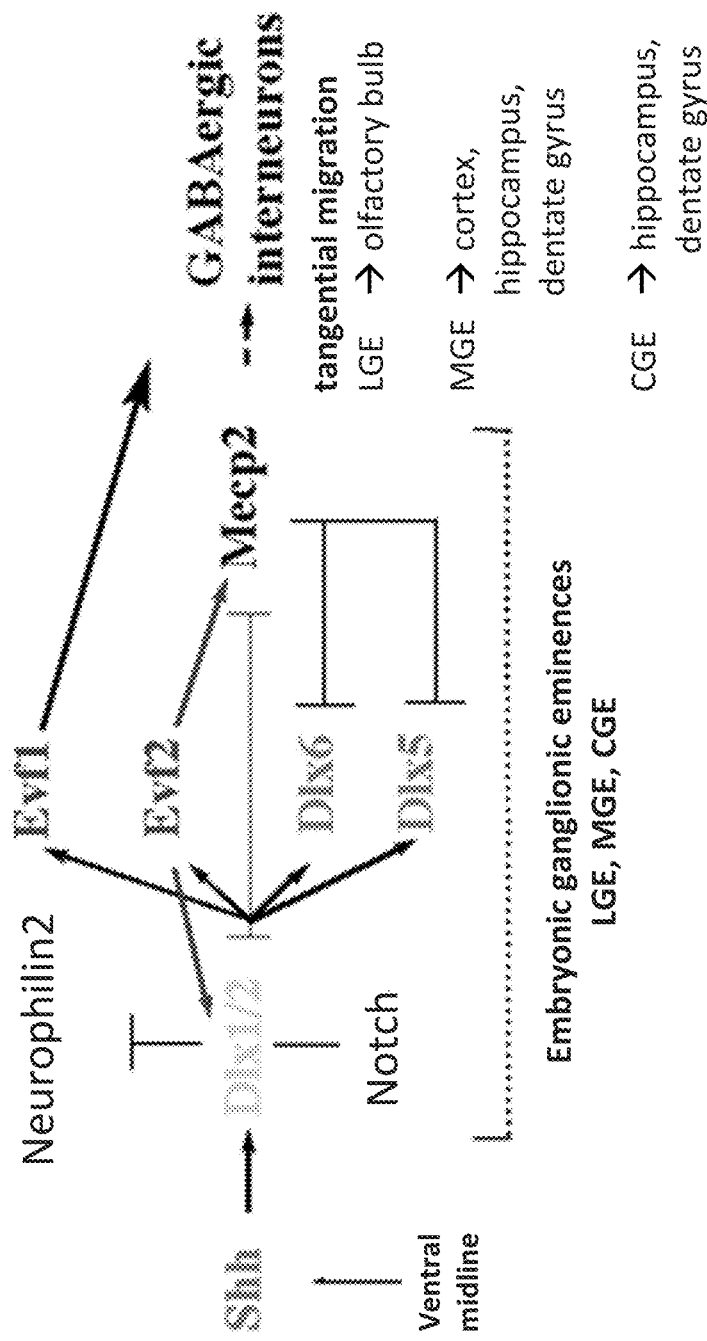

FIG. 18 provides an example of Evf-dependent interactions important for GABAergic interneuron development. Shh secreted by the ventral forebrain midline induces expression of Dlx 1/2 in embryonic ventricular and subventricular zones. Dlx 1/2 suppresses Notch and neuropilin2 and activates Dlx 5/6 and Evf's. Evf2 recruits Dlx1/2 and/or Mecp2 to balance Dlx 5/6 regulation by Dlx 5/6 intergenic enhancers. Precise regulatory control by Dlx's and Evfs is important for some aspects of GABAergic interneuron development.

Figure 19:
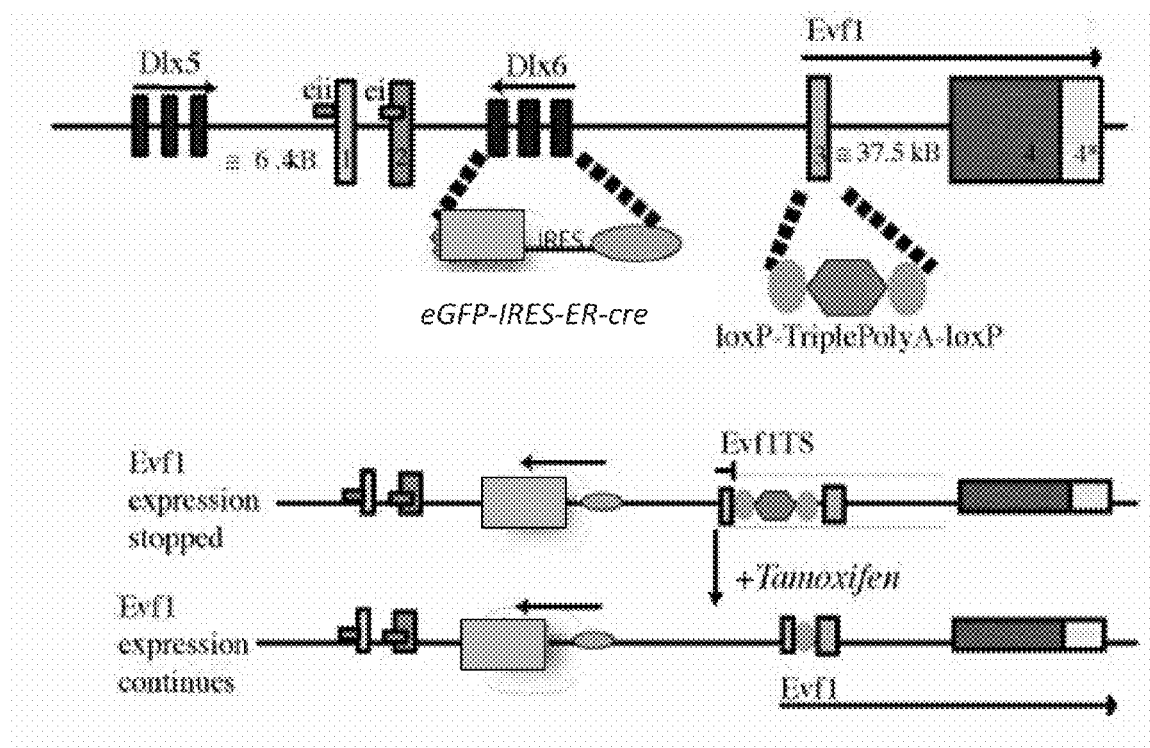

FIG. 19 provides a schematic representation of a scheme for conditional rescue. A BAC containing Evf1 (exons 3 and 4 of the Evf gene) and driven by Dlx 5/6 enhancer regulatory sequences (red) will be constructed so that tamoxifen treatment will induce removal of the triple poly A site, and allow expression of Evf1. Dlx 6 will be replaced by ER-cre (tamoxifen inducible ere) IRES-GFP to allow marking of trangenic lines.

Figure 20:
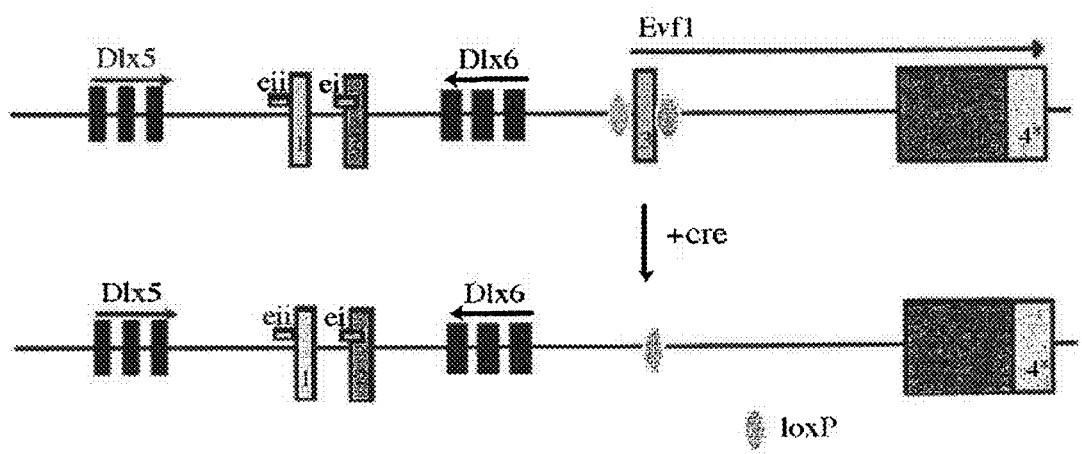

FIG. 20 provides a Scheme for conditional inactivation of Evf1 in vivo. LoxP sites will be introduced 5' and 3' to exon 3. Conditional excision of exon will result in the failure of the 5' functional region of evf1 to be transcribed. Evf1 floxedex3 XROSA-ER-cre mice will be treated at different times (E9.5, E17.5, P30) with tamoxifen to induce removal of exon3.

DETAILED DESCRIPTION

The present invention provides transgenic non-human animals that contain mutations that result in the reduction or elimination of the expression of a non-coding RNA (ncRNA) involved in the regulation of GABAergic function, such as Evf1 or Evf2. Such mutations may be introduced through the use of transgenes capable of providing for the expression of a non-functional ncRNA involved in the regulation of GABAergic activity. The transgenic non-human animals of the exemplified herein contain recombinant constructs that have triple polyadenylation transcription stop sites in exons of Evf1 or Evf2 that prevent the expression of functional Evf1 and/or Evf2. Also provided are methods and compositions for use with the disclosed animals.

Prior to describing the invention in further detail, the following terms will first be defined.
Key Abbreviations and Terms:

A list of abbreviations as used herein are as follows: Shh, sonic hedgehog; Evf, embryonic ventral forebrain; ncRNA, non-coding RNA; trucRNA, transcription regulating ultra-conserved RNA; Dlx, family of vertebrate homeodomain protein members, orthologue of the fly dll homeodomain protein; enhancer—a region of DNA that drives gene expression at a distance, independent of orientation; E11.5-E12.5, embryonic stage in days after conception; P, postnatal day; MGE, LGE, CGE, medial, lateral and caudal ganglionic eminences, respectively; GAD, glutamate decarboxylase; SVZ, subventricular zone; VZ, ventricular zone; qRT-PCR, quantitative reverse transcriptase polymerase chain reaction; GABA, gamma aminobutyric acid, major inhibitory transmitter in the brain; D2, dopamine receptor 2; pDyn, pro-dynorphin (opiate peptide); mOTu, medial olfactory tubercle; PFC, prefrontal cortex; GWA, genome wide association.

As used herein, "non-coding RNAs" (ncRNAs) refer to any RNA that functions in gene regulation, dosage compensation and imprinting. In addition to a variety of functions in the nucleus, ncRNAs can function in the cytoplasm to regulate mRNA stability, translation efficiency, and protein transport. The class of ncRNAs includes the well-known groups: ribosomal RNA (rRNA), small nuclear RNA (snRNA), transfer RNA (tRNA), microRNA (miRNA translational regulatory gene IS family), small interfering RNA (siRNA, small interfering RNA), and small nucleolar RNA (snoRNA, involved in rRNA modification).
EVF1 and EVF2

Evf-1 and Evf-2 are long (2.7 kb and 3.7 kb, respectively), polyadenylated, non-coding RNAs co-regulated with Dlx genes by Shh in the developing telencephalon and generated from alternative splicing and alternative transcription initiation (Kohtz et al., 1998, Kohtz and Fishell, 2004, Feng et al. 2006).) Evf-2 non-coding RNA transcripts overlap with the ultraconserved Dlx 5/6 intergenic enhancer (ei) and forms a complex with Dlx2 to activate transcription from the Dlx 5/6 enhancer. The single-stranded, sense Evf2 RNA is transcriptionally active, and a 5' unique, ultraconserved region is necessary and sufficient for transcriptional co-activation of the Dlx 5/6 enhancer with Dlx homeodomain proteins.

Although a direct interaction between Evf2 and Dlx2 has not been identified, complexes of Evf2 RNA and Dlx2 protein in cell lines, tissue extracts and fluorescent in situ/immuno-colocalization in nuclei from isolated embryonic cells were detected (Feng et al. 2006, FIG. 6a-c). Although not intending to be bound by theory, such results indicate that the Evf2 non-coding RNA may positively regulate Dlx 1/2 activity during development.

Evf-2, a form of Evf-1 resulting from alternative transcription initiation as well as alternative splicing, is transcribed from ei, one of the two Dlx 5/6 conserved intergenic regions previously identified by Zerucha et al. (2000) (Feng et al.). Dlx5/6 ei is one of several hundred ultraconserved sequences located close to other key developmental regulators and DNA binding proteins (Santini et al. 2003, Spitz et al. 2003, Bejerano et al. 2004, Boffelli et al. 2004, Sabarinadh et al. 2004, Sandelin et al. 2004, Woolfe et al. 2005). The function of these ultraconserved regions is presently not known. Transcription of the Dlx 5/6 ei has been shown to be conserved in vertebrates, and that the ultraconserved region of Evf-2 cooperates with the homeodomain protein Dlx-2 to increase the activity of the Dlx 5/6 enhancer in a target and homeodomain-specific manner (Feng et al. (2006)). As disclosed herein Evf-1 exhibits similar transcription-regulating activities. The present invention provides, at least in part, that developmentally regulated ncRNAs may function in trans to regulate the transcriptional activity of homeodomain proteins.

Evf-1 (Kohtz et al., 1998) is a downstream target of the patterning protein Sonic hedgehog. Evf1 is a developmentally regulated, 2.7 kb polyadenylated ncRNA, transcribed upstream of the mouse Dlx-6 gene (Kohtz and Fishell, 2004). The Evf-1 non-coding RNA is encoded by two exons separated by a large 37.5 kb intron. The Evf1 exon 1 is 4 kb upstream of the Dlx 6 gene and 8 kb distant from the conserved enhancer ii (eii) (Kohtz and Fishell, 2004). The Evf1 exon 1 overlaps with the Evf2 exon3 sequence (See FIG. 10A) Evf1 expression resembles Dlx-6 sense RNA and antisense RNA (Lui et al., 1997) expression in the ventral forebrain and branchial arches (Kohtz and Fishell, 2004). Vertebrate Dlx genes are part of a homeodomain protein family related to the *Drosophila* Distalless gene (dll) (reviewed by Panganiban and Rubenstein, 2002). Genetic deletion of Dlx genes in mice demonstrates their important role in neuronal differentiation and migration, as well as craniofacial and limb patterning during development (Anderson et al., 1997a, 1997b, Depew et al., 1999, Acampora et al., 1999, Robeldo et al. 2003). Loss of Dlx-1 has been associated with specific neuronal loss and epilepsy (Cobos et al. 2005). The Dlx genes are expressed in bi-gene clusters, and conserved intergenic enhancers have been identified for the Dlx 5/6 and Dlx 1/2 loci (Zerucha et al. 2000, Ghanem et al. 2000). Dlx-2 binds sequences in the conserved Dlx 5/6 intergenic region, as shown by gel shift and CHIP analysis (Zerucha et al. 2000, Zhou et al. 2004). The semaphorin receptor, neuropilin2 has also been shown to be directly repressed by Dlx 1/2 (Le et al. 2007). Evf-1 expression closely resembles Dlx-6 sense RNA and previously identified anti-sense RNA (Lui et al., 1997) expression in the ventral forebrain and branchial arches (Kohtz and Fishell, 2004).

Evf1 and Evf2 show some similarities to other non-coding RNAs. For example, similarities between Evf-2 and the previously characterized ncRNAs H19 (reviewed by Arney, 2003), Air (Sleutels et al. 2002), roX (Amrein and Axel, 1997, Meller et al., 1997), SRA (Lanz et al., 1999), and NRSE (Kuwabura et al. 2004) are apparent. H19 and Evf-2 were isolated in a differential expression screen, are developmentally regulated, polyadenylated and spliced. Their sizes are similar (H19=2.3 kb, Evf-2=3.8 kb). Both H19 and the transcription-regulatory region of Evf-2 contain no open reading frames larger than 200 bp by cross-species sequence conservation analysis and testing by in vitro translation. While it has been shown that H19 ncRNA does not play a role in imprinting the Igf2 locus, a DNA element located near the H19 promoter (H19-DHR) has been found to influence the imprinting of the Igf2 locus (Schmidt et al., 1999, Hark et al. 2000). The trans-acting effects of H19 ncRNA have been linked to tumor suppression, but a mechanism has not been identified. The relationship of Air, a 108 kb polyadenylated, non-spliced ncRNA, transcription through an imprinting control element (ICE) and anti-sense transcription to the Igf2r promoter (Wutz et al. 2001, Zwart et al. 2001) may be similar to the relationship between Evf-2, the Dlx 5/6 enhancer, and the Dlx-6 promoter. The promoter of Air overlaps with the ICE element, and premature transcription termination of Air results in silencing of three genes in the region, two of them non-overlapping with Air (Sleutels et al. 2002). The ability of roX RNAs to activate transcription of the X-chromosome in *Drosophila*, as well as roX DNA to serve as a chromosome entry point for activation may be mechanistically similar to Evf-2. While DNA target specificity of trans-acting roX ncRNAs has not been found, a short 217 bp roX1 DNA fragment is sufficient to produce an ectopic chromatin entry site (Kageyama et al. 2001). Recruitment by roX1 DNA was roX1 ncRNA independent (Kageyama et al. 2000). As shown in more detail in the examples herein, Evf2 transcription is important for recruiting Dlx proteins to Dlx 5/6 enhancer sequences. Therefore, the Evf-2/Dlx-2 complex on the Dlx 5/6 enhancer may function similarly as a specific chromosome entry point. The specificity and co-activator function of Evf-2 is similar to SRA, an ncRNA that specifically co-activates steroid hormone receptor activity (Lanz et al., 1999). More recently, it was shown that interaction between SRA ncRNA-SLIRP protein interactions recruit factors to nuclear receptor binding sites on chromatin (Hatchell et al. 2006). Finally, NRSE is a small double stranded RNA that is involved in neuronal cell fate choice and directly interacts with the transcription factor complex NREST (Kuwabura et al. 2004), exhibiting functional similarity with Evf2. Experiments in this proposal will investigate whether Evf-1, like Evf2, is important for Dlx recruitment in the Dlx 5/6 region.

Similar to the gaining acceptance of new roles for RNAs in biological processes is the idea that dual functions can be attributed to a single molecule. This idea is not only relevant when looking at the H19, Air, roX, and Evf2 examples, where a gene sequence may function at both the level of DNA and RNA, but also in the action of transcription factors. Reports of transcription factors that bind DNA and RNA with distinct roles have been reported (reviewed by Cassiday and Maher, 2002). Three demonstrated (and more hypothesized) examples of this include the following: TFIIIA, a zinc finger containing transcription factor that binds both 5S rDNA and 5S rRNA (Engelke et al., 1980, Clemens et al., 1993), tra-1, another zinc finger transcription factor that regulates developmental genes and binds the tra-2 mRNA 3'UTR (Graves et al., 1999), and bicoid, a homeodomain containing transcription factor that regulates developmental genes and suppresses cad mRNA translation by binding to the cad mRNA 3'UTR (Dubnau and Struhl 1996). In our studies, we show that Dlx-2, a homeodomain-containing transcription factor, known to bind and activate the Dlx 5/6 enhancer, cooperates with Evf-1 or -2 ncRNAs, resulting in an increase of Dlx 5/6 enhancer activity. However, a direct interaction between Evf-2 RNA and Dlx-2 proteins has not been found. The presence of Evf-2/Dlx-2 complexes in two concentrated spots within the nucleus supports a direct role of the Evf-2 ncRNA on Dlx-2 transcriptional activity. Chromatin immunoprecipitation (CHIP) data provided herein shows that in mice lacking Evf2, Dlx proteins fail to be recruited to ei and eii in vivo. However, Evf1 RNA/protein complexes and the effects of loss of Evf1 on transcription factor recruitment has not been performed.

Thus, target-specific transcriptional regulation may provide a common mechanism for homeodomain transcriptional regulation. Reports that the 7SK snRNA (Yang et al. 2001, Nguyen et al. 2001) and 6S RNA (Montzka et al. 2000) affect transcription by modulating RNA polymerase activity as well as the repression of RNApolIII-dependent transcription by the pole cell granule (pgc) ncRNA in *Drosophila* germ cells (Martinho et al. 2004) show that RNAs can effect transcription through a general mechanism. Unlike 7SK snRNA, 6S RNA, and pgc ncRNA, Evfs are a developmentally regulated ncRNA that affects transcriptional activity by cooperation and complex formation with a developmentally regulated homeodomain protein rather than by affecting the general transcriptional machinery through interactions with an RNA polymerase. Thus, other conserved non-protein coding regions and enhancer sequences may be transcribed to generate polyadenylated ncRNAs capable of self-activation and transcription factor complex formation. Although not intending to be limited by theory, the trans-acting effects of Evf-2 on enhancer activity may be based on the identity of the 5 prime region of Evf-2 with the evolutionarily and functionally conserved Dlx 5/6 enhancer ei sequences. Given that conserved intergenic regions have been identified for other Dlx loci (Ghanem et al. 2003), that 97% of the human genome is non-coding with numerous putative and demonstrated non-coding transcripts, and that comparisons between the human and Fugu genomes reveal multiple conserved non-coding sequences (Gilligan et al. 2002), the results provided herein suggest that it will be important to consider the role of enhancer and conserved non-protein coding sequences in transcriptional regulation at both the DNA and RNA levels.

Altered GABAergic Signaling During Drug Addiction

As disclosed in more detail in the examples below, a single non-coding RNA, designated as Evf1, controls development of GABAergic interneurons leading to increased susceptibility to the effects of cocaine. While altered dopamine signaling has been the focus of many cocaine studies, GABA may also be involved in mediating cocaine abuse and/or addiction. Thus, modifications of the expression of Evf1 may affect both dopamine signaling and GABAergic interneuron development. Altered GABA transmission can result from genetic, epigenetic or environmental factors determined during development of in the adult brain.

As provided herein, disruption of non-coding RNA regulates control of GABAergic interneurons during development and can cause reduced GABA transmission in the adult cortex, resulting in increased susceptibility to the effects of cocaine.

Also as disclosed in more detail in the examples below, a single non-coding RNA, designated as Evf2, regulates transcription of the homeodomain transcription factors DLX5 and DLX6 in developing forebrain tissue, and may be important for the proper formation of GABA-dependent neuronal circuitry in adult brain and be involved in various neurological disorders. Thus, modifications of the expression of Evf2 may affect GABAergic interneuron development.

Mutant Animals

Thus, in one embodiment, the present invention provides transgenic non-human animals having mutations that result in a decreased expression of the non-coding RNAs Evf1 or Evf2 or decreased expression of functional non-coding RNAs Evf1 or Evf2. These animals are also referred to as Evf1 TS/TS and Evf2 TS/TS, respectively.

The transgenic animals exhibit decreased expression of functional non-coding RNAs Evf1 and/or Evf2 relative to a corresponding wild-type non-human animal of the same species. The transgenic non-human animals exhibit at least an 80% reduction in the expression, for example, of functional Evf1 and/or Evf2 compared to that exhibited by a wild-type non-human animal of the same species. In other embodiments, the transgenic non-human animals exhibit at least an 85%, 90%, 95%, or 98% reduction in the expression of functional Evf1 and/or Evf2 compared to that exhibited by a wild-type non-human animal of the same species. In other embodiments, the transgenic animal exhibits no detectable expression of functional Evf1 and/or Evf2 as compared to that exhibited by a wild-type animal of the same species.

The mutations that result in the decreased or eliminated expression of the non-coding RNAs can be any mutation that results in the decrease or elimination of expression of Evf1 and/or Evf2 or that results in the expression of a non-functional Evf1 and/or Evf2 RNA. The mutations may result in the reduced or eliminated expression or the expression of a non-functional RNA with respect to either Evf1 or Evf2, but allow for the expression of a functional RNA with respect of the other RNA. For example, mutations may be introduced that result in the expression of a non-functional Evf2 RNA, yet still results in the expression of a functional Evf1 RNA.

With regard to Evf1 mutations, any mutation may be introduced that reduces or eliminates the expression of Evf1. Such mutations may be introduced into any portion of the Evf sequence that results in the reduction or elimination of the transcription of Evf1. In certain embodiments for the Evf1 mutation, mutations may be inserted into the third exon of the Evf sequence. Thus for example, such mutations may be inserted into a genomic location within the first 200 nucleotides of the Evf sequence, or within the first 175, 150, 125, 100, or 50 nucleotides of the Evf1 sequence. In other embodiments, mutations are introduced that reduce or eliminate the expression of Evf1, while providing for the expression of a functional Evf2 RNA sequence.

With regard to Evf2 mutations, any mutation may be introduced that reduces or eliminates the expression of Evf2. Such mutations may be introduced into any portion of the Evf sequence that results in the reduction or elimination of the transcription of Evf2. In one embodiment, the mutations may be introduced into a region of the Evf sequence such that a truncated RNA is transcribed that lacks at least a portion of the ultraconserved Dlx 5/6 ei region. In other embodiments, mutations may be introduced that result in the transcription of an RNA sequence completely lacking the ultraconserved ei region of Dlx5/Dlx6 intergenic region. Such mutations may be introduced to reduce or eliminate the expression of the Evf2 sequence, yet may allow for continued expression of Evf1. For example, such mutations may be introduced into exon 1 of the Evf sequence, which would allow for continued expression of Evf1 since Evf1 is expressed starting from exon 3 of the Evf sequence. In other embodiments, the mutations may be introduced in the first 200, 175, 150, 125, or 100 nucleotides of the Evf2 coding sequence.

As exemplified herein, characterization of the Evf2 TS/TS mutant animals shows a reduction or failure of DLX and MECP2 transcription factor binding to DNA control elements in neurons that will become GABAergic in the adult brain. In addition, decreased GAD67 RNA and reduced synaptic inhibition may also be exhibited in Evf2 TS/TS adults in the adult hippocampus, a region important for higher brain functions. In some embodiments, the Evf2 TS/TS mutants demonstrate a recovery in the number of GABAergic interneurons in adult stages, indicating that GABAergic recovery is possible. The data provided herein also provide a link between MECP2, the neurotransmitted GABA, autism disorders, and non-coding RNA control. The data provided herein also provide a link between MECP2, the neurotransmitted GABA, mood disorders, and non-coding RNA control.

Thus, in one embodiment, the present invention provides transgenic non-human animals having defective GABA neurotransmission. Although the defective GABA neurotransmission may be the result of any mutation effecting GABA neurotransmission, the exemplified animals have been modified through the use of recombinant nucleic acid constructs.

In one embodiment, the present invention provides polyadenylated non-coding RNAs having transcriptional activities. Such polyadenylated non-coding RNAs include Evf1 and its alternatively spliced form Evf2.

In another embodiment, the studies disclosed herein with Evf1 and Evf2 mutant mice demonstrate the ability for polyadenylated non-coding RNAs to control GABAergic interneuron development and adult brain circuitry.

Thus, the mutant mouse model provides support for the linkage of embryonic regulation of GABAergic interneuron precursors to drug sensitivity. In some embodiments, this mouse model contains a mutation that reduces or eliminates the expression of Evf1. Such mutants may provide models for therapeutic discovery of agents for use in treating drug addiction disorders, such as addiction to nicotine or cocaine. The present invention provides a mechanism in which singular changes in polyadenylated non-coding RNAs during development control gene expression, affecting GABA-dependent control of brain circuitry and ultimately drug abuse and addiction. Such a mechanism provides a model animal for understanding how predisposition to drug use may be determined during development, but may also be used, alone or in combination with genome wide association studies, to identify predisposing loci to drug abuse and addiction in humans.

Thus, in another embodiment, the present invention provides a transgenic non-human animal that has reduced or eliminated expression of Evf1 non-coding RNA in identified regions of the animal's brain. The expression of Evf1 may be reduced or eliminated in any brain tissue in the model animal, such as the medial olfactory tubercle (mOTu), nucleus accumbens, and/or the prefrontal cortex (PFC). In some embodiments, the expression of Evf1 is reduced or eliminated in at least the mOTu and PFC tissues, which correspond to adult brain regions involved in regulating psycho stimulant drug response and addiction.

As discussed above, expression of the Evf1 and/or Evf2 sequences can be reduced or eliminated using any method available for the modification of the expression of an endogenous sequence. In one embodiment, transcription stop sequences may be introduced into the Evf sequence that results in the expression of a truncated RNA. Any transcription stop sequence can be used in the production of the animal model herein. For example, as exemplified below, transgenic non-human animals have a triple polyadenylation stop sequence inserted into the Evf1 sequence that prevents Evf1 transcription. The exemplified mice show that the Evf1 mutant PFC contains fewer GABAergic interneurons and expresses genes indicating altered dopamine signaling. The PFC may be activated in humans during cues which result in drug craving, leading to the possibility that addiction usurps normal prefrontal cortical functions to obtain drugs (Hyman et al. 2006, Hyman 2005). For individuals within the human population with slightly imbalanced GABAergic function in the PFC, this diversion may occur more readily, rendering them more susceptible to the addictive properties of drugs.

Thus, the non-coding RNA sequences that can regulate the balance of GABAergic signaling in the PFC (as in the case of Evf1) or hippocampus (as in the case of Evf2), makes the genes coding for these RNAs potential targets for identifying genetic pre-disposition to addiction and mental disorders. For example, the adult expression of Evf1, and possibly other similar non-coding RNAs, may provide novel, highly specific targets for modulating neuronal function in regions of the brain important for drug response. Such targets provide a model for the development of agents that modulate specific RNA targets rather than agonists/antagonists of neurotranmission which interfere with multiple neuronal functions. In another embodiment, the non-coding RNA control of GABAergic interneuron number may be limited to particular development stages, such as embryonic events. The Evf1 mutant animals provide an understanding of how the Evf1 noncoding RNA controls GABAergic signaling in the brain to identify novel treatments and/or prevention of drug addiction, schizophrenia, learning or memory disorders.

Thus, in one embodiment, the models disclosed herein may be useful for the screening and identification of therapeutic agents for the prevention or treatment of drug addiction. It is accepted that psycho stimulants disrupt the normal balance of neurotransmission in different brain regions. Although the major mode of action of the psychostimulants such as cocaine and amphetamine are through dopamine uptake or efflux, multiple systems of neurotransmission are involved in their response and addiction. For example, GABAergic and dopaminoceptive signaling in the medial olfactory tubercle (mOTu), nucleus accumbens and PFC play important roles in the response to psychostimulant drugs.

In addition, multiple correlations provide further support that a genetic for drug addiction in the human population exists. Genome-wide association (GWA) screens are beginning to identify specific loci that may confer genetic pre-disposition to drug addiction. For example, disruptions of genes involved in the GABA pathway have been identified through GW A screens for nicotine addiction (Bierut et al. 2006, Saccone et al. 2006, Li et al. 2007). These results suggest that individuals with slightly imbalanced GABAergic signaling may be more susceptible to the rewarding effects of drugs, and different aspects of addiction that can follow. While imbalanced GABA may derive from mutations in receptors or transporters important for synaptic transmission, cellular and molecular events during development may alter the proper development of subpopulations of GABAergic interneurons may also be a cause.

Methods of Producing Modified Animals

In another embodiment, the present invention provides constructs and methods for the preparation of a modified non-human animal that has reduced or inhibited expression of functional non-coding RNAs Evf1 and/or Evf2.

The non-human animal can be modified by any method available to reduce or eliminate the expression of the endogenous non-coding RNAs. Such methods include, but are not limited to mutagenesis and transgenic methods that result in the reduction or elimination of the expression of functional non-coding RNA involved in the regulation of GABAergic activity. In one embodiment, the modified non-human animal is produced using transgenic methods to introduce Evf1 or Evf2 targeting DNA constructs to introduce mutations into the Evf sequence that are capable of reducing the expression of functional non-coding RNAs, Evf1 and/or Evf2.

The transgenic, non-human animal of the present invention, or any transgenic, non-human animal exhibiting decreased expression of Evf1 or Evf2 relative to wild-type, may be produced by a variety of techniques for genetically engineering transgenic animals. For example, to create a transgenic, non-human animal exhibiting decreased expression of Evf1 and/or Evf2 relative to a corresponding wild-type animal of the same species, an Evf1 and/or Evf2 targeting vector is generated first.

An "Evf1 targeting vector" and/or an "Evf2 targeting vector" refers to an oligonucleotide sequence that comprises a portion, or all, of the Evf1 and/or Evf2, and is sufficient to permit homologous recombination of the targeting vector into at least one allele of the endogenous Evf1 and/or Evf2 sequence within the recipient cell. The targeting vector may further comprise a positive or negative heterologous selectable marker gene (e.g., the positive selection gene, neo). The targeting vector may be a lambda phage-based recombineering vector as generally described in Liu, et al., Genome Res. 13, 476-484 (2003).

DNA constructs for random integration need not include regions of homology to mediate recombination. Where homologous recombination is desired, the DNA constructs will comprise at least a portion of the target gene with the desired genetic modification, and will include regions of homology to the target locus. Conveniently, markers for positive and negative selection may be included. Methods for generating cells having targeted gene modifications through homologous recombination are known in the art. For various techniques for transfecting mammalian cells, see Keown et al. (1990) Methods in Enzymology 185:527-537.

Any method may be used in the preparation of DNA constructs that allows for the modification of the expression of an Evf RNA sequence. In some embodiments, the methods involve the insertion of transcription stop sequences into the Evf sequence to result in the expression of a truncated Evf1 and/or Evf2 sequence. Although such methods may allow for some expression of a full length Evf1 or Evf2 sequence, the methods generally result in the majority of the expressed Evf sequence in a transgenic cell being a truncated Evf sequence, such as a truncated Evf1 or Evf2 sequence.

In methods involving the use of the insertion of transcription stop sequences, any transcription stop sequence may be used in the preparation of the construct. For example, triple polyadenylation (polyA) stop sequences (TS) may be used in the methods disclosed herein. In addition, such transcription stop sequences may be inserted anywhere in the Evf sequence to result in the expression of a truncated Evf1 and/or Evf2 sequence.

In some methods of the present invention, the Evf1 and/or Evf2 targeting vector that has been generated then may be introduced into a recipient cell (comprising a wild-type Evf1 or Evf2 sequence) of a non-human animal, to produce a treated recipient cell. This introduction may be performed under conditions suitable for homologous recombination of the vector into at least one of the wild-type Evf1 and/or Evf2 sequences in the genome of the recipient cell. The non-human animal may be any suitable animal (e.g., cat, cattle, dog, horse, goat, rodent, and sheep), as described above, but is preferably a rodent. More preferably, the non-human animal is a rat or a mouse. The recipient cell may be, for example, an embryonic stem cell, or a cell of an oocyte or zygote.

The Evf1 and/or Evf2 targeting vector of the present invention may be introduced into the recipient cell by any in vivo or ex vivo means suitable for gene transfer, including, without limitation, electroporation, DEAE Dextran transfection, calcium phosphate transfection, lipofection, monocationic liposome fusion, polycationic liposome fusion, protoplast fusion, creation of an in vivo electrical field, DNA-coated microprojectile bombardment, injection with recombinant replication-defective viruses, homologous recombination, viral vectors, and naked DNA transfer, or any combination thereof. Recombinant viral vectors suitable for gene transfer include, but are not limited to, vectors derived from the genomes of viruses such as retrovirus, HSV, adenovirus, adeno-associated virus, Semiliki Forest virus, cytomegalovirus, and vaccinia virus.

In accordance with such methods, the treated recipient cell then may be introduced into a blastocyst of a non-human animal of the same species (e.g., by injection or micro injection into the blastocoel cavity), to produce a treated blastocyst. Thereafter, the treated blastocyst may be introduced (e.g., by transplantation) into a pseudopregnant non-human animal of the same species, for expression and subsequent germline transmission to progeny. For example, the treated blastocyst may be allowed to develop to term, thereby permitting the pseudopregnant animal to deliver progeny comprising the homologously recombined vector, wherein the progeny may exhibit decreased expression of Evf1 and/or Evf2 relative to corresponding wild-type animals of the same species. It then may be possible to identify a transgenic non-human animal whose genome comprises a disruption in its endogenous Evf1 and/or Evf2 sequence. The identified transgenic animal then may be interbred with other founder transgenic animals, to produce heterozygous or homozygous non-human animals exhibiting decreased expression of Evf1 and/or Evf2 relative to corresponding wild-type animals of the same species.

A type of recipient cell for transgene introduction is the embryonal stem cell (ES). ES cells may be obtained from pre-implantation embryos cultured in vitro. Transgenes can be efficiently introduced into the ES cells by standard techniques such as DNA transfection or by retrovirus-mediated transduction. The resultant transformed ES cells can thereafter be combined with blastocysts from a non-human animal. The introduced ES cells thereafter colonize the embryo and contribute to the germ line of the resulting chimeric animal.

In order to produce the gene constructs used in the invention, recombinant DNA and cloning methods, which are well known to those skilled in the art, may be utilized (see Sambrook et al., 1989, Molecular Cloning, A Laboratory Manual, 2nd Ed., Cold Spring Harbor Laboratory Press, NY). In this regard, appropriate Evf1 and/or Evf2 sequences may be generated from genomic clones using restriction enzyme sites that are conveniently located at the relevant positions within the Evf1 and/or Evf2 sequence. Alternatively, or in conjunction with the method above, site directed mutagenesis techniques involving, for example, either the use of vectors such as M13 or phagemids, which are capable of producing single stranded circular DNA molecules, in conjunction with synthetic oligonucleotides and specific strains of *Escherichia coli* (*E. coli*) (Kunkel, T. A. et al., 1987, Meth. Enzymol. 154:367-382) or the use of synthetic oligonucleotides and PCR (polymerase chain reaction) (Ho et al., 1989, Gene 77:51-59; Kamman, M. et al., 1989, Nucl. Acids Res. 17:5404) may be utilized to generate the necessary nucleotide sequences. Appropriate Evf-sequences may then be isolated, cloned, and used directly to produce transgenic animals. The sequences may also be used to engineer the chimeric gene constructs that utilize regulatory sequences other than the Evf promoter, again using the techniques described here. These chimeric gene constructs can then also be used in the production of transgenic animals.

Methods for Identifying Drug Candidates

In another embodiment the transgenic, non-human animal of the present invention can be used for the testing of compounds for the prevention or treatment of brain disorders, and more specifically for the testing of compounds for the treatment of mood disorders. A mood disorder, as used herein, is any one of a group of diagnoses in the Diagnostic and Statistical Manual of Mental Disorders (DSM IV TR) classification system where a disturbance in the person's mood is hypothesized to be the main underlying feature. Two groups of mood disorders are broadly recognized; the division is based on whether the person has ever had a manic or hypomanic episode. Thus, there are depressive disorders, of which the best known and most researched is major depressive disorder (MDD) commonly called clinical depression or major depression, and bipolar disorder (BD), formerly known as "manic depression" and described by intermittent periods of manic and depressed episodes.

In another embodiment the transgenic, non-human animal of the present invention can be used for the testing of compounds for the prevention or treatment of brain disorders, and more specifically for the testing of compounds for the treatment of autism spectrum disorders, addictive disorders, and other psychiatric disorders such as schizophrenia, epilepsy, and Tourette's syndrome.

Drug screening assays in general suitable for use with transgenic animals are known. See, for example U.S. Pat. Nos. 6,028,245 and 6,455,757. Thus, the transgenic animals may be used as a model system for human brain disorders and/or to generate neuronal cell lines that can be used as cell culture models for these disorders. The transgenic animal model systems for brain disorders may be used as a test substrate to identify drugs, pharmaceuticals, therapies and interventions which may be effective in preventing, slowing progression, or treating such disorders. Therapeutic agents may be administered systemically or locally. Suitable routes may include oral, rectal, or intestinal administration; parenteral delivery, including intramuscular, subcutaneous, intramedullary injections, as well as intrathecal, intracerebral, direct intraventricular, intravenous, intraperitoneal, intranasal, or intraocular injections, just to name a few. The response of the animals to the treatment may be monitored by assessing the reversal of one or more symptoms associated with a given brain disorders. With regard to intervention, any treatments which reverse any aspect of the disorder should be considered as candidates for therapeutic intervention. However, treatments or regimes which reverse the constellation of pathologies associated with any of these disorders may be preferred. Dosages of test agents may be determined by deriving dose-response curves. The transgenic animal model systems for brain disorders may also be used as test substrates in identifying environmental factors, drugs, pharmaceuticals, and chemicals which may exacerbate the progression of the disorders that the transgenic animals exhibit. In an alternate embodiment, the transgenic animals of the invention may be used to derive a cell line which may be used as a test substrate in culture, to identify both agents that reduce and agents that enhance the disorders. While primary cultures (e.g. hippocampal neurons) derived from the transgenic animals of the invention may be utilized, continuous cell lines can also be obtained. For examples of techniques which may be used to derive a continuous cell line from the transgenic animals, see Small et al., 1985, Mol. Cell. Biol. 5:642-648.

Also in another particular embodiment the transgenic non-human animal of the present invention will be useful for screening candidate therapeutic agents in order to: (1) analyze the specificity of the candidate agent; (2) monitor for side-effects of the drugs; and (3) follow long-term effects of such agents (e.g., compensatory effects, complications, etc.).

In yet another embodiment the non-human, transgenic animal of the present invention can be used for the testing of agents that specifically affect GABA synthesis. In yet another embodiment cell lines derived from the non-human transgenic animals can be used for the testing of test agents to identify agents that specifically affect the formation of GABA-dependent neuronal circuitry in adult brain tissue. As used herein, "test agent" shall include a protein, polypeptide, peptide, nucleic acid (including DNA, RNA, and an antisense oligonucleotide), antibody (monoclonal and polyclonal, Fab fragment, F(ab')$_2$ fragment), molecule, compound, antibiotic, drug, and any combinations thereof. A Fab fragment is a univalent antigen-binding fragment of an antibody, which is produced by papain digestion. A F(ab')$_2$ fragment is a divalent antigen-binding fragment of an antibody, which is produced by pepsin digestion. The antibody of the present invention may be polyclonal or monoclonal, and may be produced by techniques well known to those skilled in the art.

The identified agents can be used for the manufacture of medicine for the prevention or treatment of neural disorders, such as drug addiction, schizophrenia, autism spectrum disorders, mood disorders (e.g. depression), learning disorders, behavioral disorders, and the like.

Embodiments are further defined in the following Examples. It should be understood that these Examples are given by way of illustration only. From the above discussion and these Examples, one skilled in the art can ascertain the essential characteristics, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

EXAMPLES

Example 1

Preparation and Characterization of Evf2 Mutant Mice

The potential of the genome to code for functional non-coding RNAs (ncRNAs) is only beginning to be uncovered (Prasanth et al. (2007) and Mattick, et al. (2006). Although many ncRNAs belong to classes of small regulatory RNAs, one subset, long, polyadenylated ncRNAs (lpncRNAs), act cooperatively with protein partners (Shamovsky et al. (2006)). It was previously found that Evf2, a lpncRNA target of sonic hedgehog (SHH) signaling in the developing telencephalon, exhibits trans-acting transcriptional cooperativity with DLX homeodomain proteins, increasing Dlx5/6 enhancer activity in a neural stem cell line (Feng et al. (2006)). Identification of an ultraconserved Dlx5/6 intergenic DNA regulatory element (Zerucha et al. (2000) has led to the discovery of more than 1,000 ultraconserved DNA sequences near important developmental regulators or transcription factors (Gilligan et al. (2002), Santini et al. (2003), and Bejerano et al. (2004)). The domain of Evf2 that is necessary and sufficient for its transcription regulating activity lies in this ultraconserved sequence at the 5' end of Evf2 RNA (Feng et al. (2006)). The finding that Evf2 has transcription-regulating activity (Feng et al. (2006)) raised the possibility that subsets of ultraconserved DNA sequences are transcribed and functional. Recently, additional ultraconserved brain lpncRNAs have been identified (Mercer et al. (2008)), supporting the possibility that ultraconserved ncRNAs constitute a new class of transcription-regulating ultraconserved ncRNAs (trucRNAs). In this study, we found, to the best of our knowledge, for first time that the Evf2 trucRNA are important for gene regulation and the development of interneurons that produce GABA, the major inhibitory neurotransmitter in the brain.

The balance between excitation and inhibition in the brain is important for proper function and is maintained by two major classes of neurons: excitatory projection neurons and inhibitory local circuit interneurons. Although excitation is primarily mediated by the neurotransmitter glutamate, GABA primarily mediates inhibition. Recently, multiple regulatory roles of GABAergic interneurons have been identified (Di Cristo (2007)). The dysfunction of GABA-regulated circuits has been implicated in different psychiatric disorders, such as schizophrenia, autism and Tourette's syndrome, as well as epilepsy. In methyl CpG-binding protein (Mecp2) mutant mice (Bienvenu et al. (2006), Moretti et al. (2006), and Chahrour et al. (2007)), a model for the human autism spectrum disorder (ASD) Rett syndrome, GABA-dependent inhibitory cortical activity decreases (Dani et al. (2005)). In dorsal lateral prefrontal cortex of schizophrenic patients, one of the most consistent findings is a reduction in GAD67, the enzyme responsible for GABA synthesis (Lewis et al. (2005)). Therefore, multiple lines of evidence implicate alterations of GABAergic function in a variety of neurological diseases. Exemplified herein is a noncoding RNA that controls development of GABAergic interneurons and adult brain circuitry, making this mechanism a target for studying both development and disease.

Methods:

Generation of Evf2$^{TS/TS}$ Mice.

Triple polyA sequences (TS) were used to modify the expression of Evf2 for their ability to provide a strong transcription stop signal. For the preparation of the Evf2 mutant, a TS was inserted into Evf exon 1, 84 nucleotides from the start of Evf exon 1. The flanking sequences used were as follows:

TTT CTA GAC CCT GAT CAT TG [TS] CTT AAG AGA TAT TCA (SEQ ID NO: 1).

Using this location for the insertion of a TS, the largest possible Evf2 transcript in Evf2TS/TS mice is 84 nucleotides long, lacking the transcription-regulating domain, as defined in Feng et al, 2006.

An Evf2 targeting construct was generated using lambda phage-based recombineering in *E. coli* as described previously (Liu, et al. Genome Res. 13, 476-484 (2003)). Using high-fidelity Taq (Roche), homology arms of approximately 500 bp were PCR amplified (with restriction sites added) from BAC DNA. Using a three fragment ligation, homology arms were cloned into Cla I and Nhe I sites of PL253, with a HindIII site engineered between them. A 16.I-kb region (corresponding to position 6, 809, 651-6, 825, 742 on mouse chromosome 6, NCBI assembly) was retrieved from pBAC e3.6 M8 (M. Ekker) into the retrieval plasmid using recombination-induced EL250 cells (Liu, et al). Further targeting was performed on the retrieved plasmid. The polyadenylation targeting vector was constructed in PL452, a floxed-Neo-containing plasmid. The triple polyadenylation signal was cloned into EcoRI and SalI sites of PL452. Approximately 500 bp of targeting homology arms were cloned sequentially on either side of the polyA-floxed-Neo insert. Briefly, fragments were PCR amplified as described above and cloned into either Cla I and KpnI sites or Not I and SacII sites. This triple polyA-floxed-Neo cassette was targeted into the retrieved 16.I-kb region using recombination-induced EL250 cells. Successful targeting was confirmed by Southern blot analysis of the completed construct using internal probes (NEBlot kit, NEB).

Mouse ES cells were targeted by homologous recombination using standard procedures. Successful targeting in ES cells was confirmed by Southern blot, verifying proper recombination at both the 5' and 3' ends. Probes were generated outside the 16.1-kb homologous region. The 5' probe was 499 bp (chromosome 6 bases 6, 808, 430-6, 808, 928) and the 3' probe was 991 bp (chromosome 6 bases 6, 825, 821-6, 826, 811). Wild-type ApaLI sites are at chromosome 6 bases 6, 828, 765 and 6, 817, 913, yielding a 10.8-kb fragment that hybridizes with the 3' probe. EL250 cells and recombineering plasmids PL253 and PL452 were provided by N. Copeland (also described on the worldwide web at the website: recombineering.ncifcrf.gov/Plasmid.asp).

Evf2TS (flexed-Neo) heterozygotes were verified by Southern blot and crossed to EIIAcre mice (Jackson Labs) for two generations. Neo removal was verified by PCR (data not shown). Mice are kept on a mixed 129/FVB/C57Bl6 background and housed according to IACUC guidelines.

The primer sequences used for the preparation and verification of the Evf2 mutant were as follows. For gene targeting, the following primers for retrieval homology arms were used: CLa I (5'-GAT GCG AAT CGA TCG GCT TAG GCC TCC AGG TTT C-3'; SEQ ID NO: 2), HindIII (5'-AAA CCC TAA GCT TGA CTA GCG TGG CCC AAA GGT-3'; SEQ ID NO: 3), HindIII* (5'-GAT GCG AAA GCT TCT GTC AGT GCC AAA ATG GAA GGA CAT-3'; SEQ ID NO: 4), NheI (5'-GAT GCG AGC TAG CGG GGT TGG GAC CTG GTT TTA GG-3'; SEQ ID NO: 5). For targeting arms, we used Sac II (5'-TTA GTT CCG CGG CCT GGT CCT TTC TTC GTC TCA AGT C-3'; SEQ ID NO: 6), NotI (5'-ATT TGC GGC CGC CTT AAG AGA TAT TCA CCG GGG TAA GTT TTT ATT-3'; SEQ ID NO: 7), ClaI (5'-GAT TTT ATC GAT CAA TGA TCA GGG TCT AGA AAT CTA TAC TGA G-3'; SEQ ID NO: 8), Kpn (5'-GAT TTT GGT ACC TTC AGG GTT TGA TTT GAT CGC TAC TG-3'; SEQ ID NO: 9), 5' ES Southern probes mEvf5'0.1 (5'-TGG TGA AGC TGG AGG AAG GAC-3'; SEQ ID NO: 10) and mEvf5'0.2 (5'-CAC ACT GAC TTC TGA ACA CCC CTG-3'; SEQ ID NO: 11), and 3' Southern probes mEvD'0.1 (5'-GGG GTG AAG GAT GGT GAT TAA AGA GC-3'; SEQ ID NO: 12) and mEvf3'0.1 (5'-GTG GCT GGC TGT CCT TTG GT-3'; SEQ ID NO: 13).

For quantitative reverse transcription PCR, we used the following primers with SYBR Green: Evf2-F (0.2 µM, 5'-CTC CCT CCG CTC AGT ATA GAT TTC-3'; SEQ ID NO: 14), Evf2-R (0.2 µM, 5'-CCT CCC CGG TGA ATA TCT CTT-3'; SEQ ID NO: 15), Dlx2-F (0.15 µM, 5'-CCC TAC GGC ACC AGT TCG T-3'; SEQ ID NO: 16), Dlx2-R (0.15 µM, 5'-TCG GAT TTC AGG CTC AAG GT-3'; SEQ ID NO: 17), Nrp2-F (0.5 pM, 5'-ACT TTT CAG GAC ACG AAG TGA GAA-3'; SEQ ID NO: 18), Nrp2-R (0.5 µM, 5'-GCC AGC ATC TTT GGA ATT CAG-3'; SEQ ID NO: 19), Gad67-F (0.4 µM, 5'-ACT CCT TCG CCT GCA ACC T-3'; SEQ ID NO: 20), Gad67-R (0.4 µM, 5'-CGC CAC ACC AAG TAT CAT ACG T-3'; SEQ ID NO: 21), β-actin-F (0.3 µM, 5'-GCG AGC ACA GCT TCT TTG C-3'; SEQ ID NO: 22) and β-actin-R (0.3 µM, 5'-TCG TCA TCC ATG GCG AAC T-3'; SEQ ID NO: 23). For TaqMan PCR, we used the following primers: Dlx5-probe (0.1 µM, 5'-CAA GCA TCC GAT CCG GCG ACT TC-3'; SEQ ID NO: 24), Dlx5-F (0.1 µM, 5'-TAT GAC AGG AGT GTT TGA CAG AAG AGT-3'; SEQ ID NO: 25), Dlx5-R (0.1 µM, 5'-ACG TCG GGA ACG GAG CTT-3'; SEQ ID NO: 26), Dlx6-probe (0.1 µM, 5'-AAC GCC T AC GGA GCT TCT GAA GGA GAC A-3'; SEQ ID NO: 27), Dlx6-F (0.1 µM, 5'-GAG ACC ACA GAT GAT GTG ACT TCT CT-3'; SEQ ID NO: 28), Dlx6-R (0.1 pM, 5'-CTG CCA TGT TTG TGC AGA TTC T-3'; SEQ ID NO: 29), Evf1-probe (01 µM, 5'-AGA GCT ATG CGA CTG TAG GCA AGC CAT-3'; SEQ ID NO: 30), Evf1-F (01 µM, 5'-GCA TGG AAA CTT TGA TAC CTT GGT-3'; SEQ ID NO: 31), Evf1-R (01 µM, 5'-GCC TTT CAG AAC TAG AAG GGA TTT AAA-3'; SEQ ID NO: 32), β-actin-probe (01 µM, 5'-CAA CGA GCG GTT CCG ATG CCC T-3'; SEQ ID NO: 33), β-actin-F (01 µM, 5'-ACG GCC AGG TCA TCA CTA TTG-3'; SEQ ID NO: 34) and β-actin-R (01 µM, 5'-CAA GAA GGA AGG CTG GAA AAG A-3'; SEQ ID NO: 35). For quantitative PCR, we used the following primers with the SYBR Green PCR Core Reagents Kit: I-F (0.25 µM, 5'-TAT GAA AAG CCC AGG ATT GC-3'; SEQ ID NO: 36), I-R (0.25 µM, 5'-TGT CCC AGC TTC CTA TCA CC-3'; SEQ ID NO: 37), 2-F (0.25 µM, 5'-TGG TTT GAA AGA GGG GAA TG-3'; SEQ ID NO: 38), 2-R (0.25 µM, 5'-AGA GCG CTT ATT CTG AAA CCA-3'; SEQ ID NO: 39), 3-F (0.12 µM, 5'-CCC AGG ATC AAT TCT GAA CAA AG-3'; SEQ ID NO: 40), 3-R (0.50 µM, 5'-TCC CCA ATG TCT GCT TCA AAT-3'; SEQ ID NO: 41), 4-F (0.10 µM, 5'-TGG ATT CCC TGA ACT CCA AG-3'; SEQ ID NO: 42). 4-R (0.10 µM, 5'-AGG GCT TGG GAA CTC AAA CT-3'; SEQ ID NO: 43), 5-F (0.24 µM, 5'-GGC GCA TCT TTG CAA ATT ACA-3'; SEQ ID NO: 44), 5-R (0.50 µM, 5'-GCA GGC TGG ATT AGG ATG CTA-3'; SEQ ID NO: 45), 6-F (1.0 µM, 5'-TCG AAA GTA TTG CGT GGA TG-3'; SEQ ID NO: 46), 6-R (1.0 µM, 5'-GTG TGT ACC AAG CGC ATG TC-3'; SEQ ID NO: 47), 7-F (0.25 µM, 5'-GGC GTG TCA GCA CCT GAT TT-3'; SEQ ID NO: 48) and 7-R (0.25 µM, 5'-GCC AAG TCA CTG CCC ATC TC-3'; SEQ ID NO: 49).

ChIP Methods.

MGE tissue was collected from E13.5 mouse Evf2$^{+/+}$ or Evf2$^{TS/TS}$ embryos (10-15 embryos per group). Tissue was broken into single cells by pipetting and spun through a 70-nm filter. The DNA was crosslinked with 1% paraformaldehyde for 90 min on a rotator and then resuspended in SDS lysis buffer (1% SDS, 50 mM Tris-HCl (pH 8.1) and 10 mM EDTA) and the protease inhibitors PMSF (170 μg ml$^{-1}$), pepstatin (0.7 μg ml$^{-1}$), leupeptin (10 μg ml$^{-1}$) and aprotinin (10 μg ml$^{-1}$). The crosslinked DNA was sonicated on a Microson Ultrasonic Cell Disruptor at power 6 for six pulses of 10 s each. The sonicated mixture was spun down and the supernatant was used for ChIP.

For each immunoprecipitation condition, 20 μg of chromatin was used in a total volume of 1,000 μl TES buffer (50 mM Tris-HCl (pH 8.1), 1 mM EDTA and 150 mM NaCl) plus protease inhibitors. The chromatin was precleared on a rotator at 4° C. We added 75 μl of washed Protein G-Agarose beads for 1 h and incubated the supernatant with 10 μl of rabbit pre-immune serum for 1 h. Afterwards, 75 μl of Protein G-Agarose were added for 1 h and the supernatant was split in half for an antibody condition and a rabbit pre-immune condition. The chromatin was immunoprecipitated at 4° C., Antibody (5 μg) or rabbit preimmune serum (2 μl) were added for 4 h and then 100 μl of Protein G-Agarose was added overnight. The Protein G-Agarose beads were washed twice with low salt buffer (0.1% SDS, 1% Triton X-100, 2 mM EDTA, 20 mM Tris-HCl (pH 9.1) and 150 mM NaCl), once with 500 mM NaCl, twice with LiCl buffer (0.25M LiCl, 1% sodium deoxycholate, 1 mM EDTA, 10 mM Tris-HCl (pH 8.1) and 1% IGEPAL), and twice with TE buffer (10 mM Tris-HCl (pH 8.1) and 1 mM EDTA). The chromatin was then eluted off the Protein G-Agarose beads by incubation with 100 μl of elution buffer (1% SDS, and 0.1 M NaHCO$_3$) twice. The DNA crosslinking was reversed by incubation in 0.5 M NaCl for 5 h at 65° C. Then the DNA was proteinase K treated by adding half a volume of 15 mM EDTA/30 mM Tris-HCl (pH 8.1) and 750 μg ml$^{-1}$ proteinase K for 1 h at 65° C. The uncrosslinked DNA was phenol extracted and ethanol precipitated using glycogen. Rabbit pan-antibody to Dll was produced in the laboratory. Pan-antibodies to Dlx, as originally described (Panganiban, et al., 1995), were made in our laboratory and extensively characterized (Feng, et al. (2006)). Pan-antibodies to Dlx were raised in rabbits against the 62 amino acid butterfly Dll homeodomain-containing fragment, affinity purified and tested by western blot (Dll fragment and zebrafish Dlx 1, 2, 4 and 6, and mouse Dlx2) and immunohistochemistry (neural explants, embryonic forebrain sections). Panantibody to Dlx recognizes zebrafish Dlx family members, including Dlx 1, 2, 4 and 6 (Feng et al. (2006)).

Monoclonal anti-Mecp2 antibodies were obtained commercially (Affinity Bioreagents) and characterized previously (Kishi, et al. (2004)). We verified that these antibodies to Mecp2 bound only two bands in adult olfactory bulb extracts by western analysis (data not shown). Antibodies to HDAC1 were obtained from Sigma. Primers were optimized to concentrations at which they were 100% efficient with a standard curve slope of ~-3.32.

The enrichment of the antibodies and rabbit pre-immune serum were determined by comparing the Ct values of the immunoprecipitation condition to the Ct value of input chromatin using the following formula: $2^{-(Ct(IP)-Ct(Input))}$. Once the enrichments were calculated, the relative enrichment of each antibody was calculated for Evf2$^{+/+}$ and Evf2$^{TS/TS}$ E13.5 MGE tissue by dividing antibody enrichment by pre-immune enrichment.

Immunohistochemistry. Brain tissue was fixed in 4% paraformaldehyde overnight and then sunk consecutively in 15% and then 30% sucrose in phosphate-buffered saline (PBS) overnight. Tissue was cryostat sectioned at 18 μm and air dried before staining. In situ hybridization was carried out as previously published (Feng et al. (2006)). Immunohistochemistry was performed using tyramide amplification (TSA Kit #12, Invitrogen). Tissue was treated with 50% formamide/50% 2×SSC for 2 h at 65° C. and then washed in 2×SSC. Cells were permeabilized with 0.5% Triton X-100 in PBS and endogenous peroxidase activity was quenched by incubating the tissue in 1% hydrogen peroxide in PBS for 30 min. Tissue was blocked in 1% blocking solution (Component D) and labeled overnight with primary antibody, rabbit antibody to GABA (Sigma, 1:500) or pan-antibody to Dll (0.01 mg ml$^{-1}$, purified in the laboratory) in blocking solution. Tissue was washed in PBS and then incubated in secondary antibody, goat antibody to rabbit IgG-horseradish peroxidase conjugate (Component C, 1:100) for 1 h. Tissue was washed in PBS and a working tyramide solution was applied for IS min: Alexa Fluor 488 dye (Component A, 1:100) in amplification buffer (Component E) with 0.0015% hydrogen peroxide (Component F). Finally DAPI stain was applied for nuclear localization.

Western blot. Evf2$^{+/+}$ and Evf2$^{TS/TS}$ E13.5 MOE tissue was homogenized in SDS-PAGE sample buffer, separated on a 12.5% SDS-PAGE gel, transferred to nitrocellulose and probed with primary rabbit antibody to Dlx2 (1:2,000) from D. Eisenstat followed by secondary antibody to rabbit peroxidase (1:5,000, Sigma). Blots were reprobed with mouse antibody to β-actin (1:20,000, AC-15, Sigma). Bands were visualized using a chemiluminescence kit (Perkin Elmer).

Electroporation.

DNA was dissolved to a concentration of 0.1 μg μl$^{-1}$ in H$_2$O and 0.04% trypan blue for visualization during injections. E12.5 Evf2$^{TS/TS}$ embryos were obtained from mating Evf2$^{TS/TS}$ males and females, and dissected in cold L-15 media. The heads were placed in cold PBS and 1.5 μl of DNA was injected into the lateral ventricles of the forebrain under a dissection microscope. Electroporation using the square wave protocol (BioRad Gene Pulser XCell) delivered 5×50-ms pulses of 30 V with 1-s intervals. Each embryo was electroporated twice using electroporation paddles (Pro tech) that were placed laterally on each side and then reversed to electroporate both left and right sides of the brain. The MGE was dissected and cultured in neurobasal medium (DMEM/F12 containing B-27 (Gibco), N2 supplement (Gibco), 200 μM L-glutamine, 0.1 μg ml$^{-1}$ penicillin/streptomycin and 1 μg/ml mitomycin C on 0.02-nm filters (Nunc)). After 24 h in culture, RNA was isolated from pools of four MGE explants for qRT-PCR analysis.

RNA isolation and reverse transcription. Total RNA from pairs of E13.5 MGE tissue was isolated (Chomczynski, et al. (1987)) and treated with RNASE-free DNASE I (NEB) and reverse-transcribed using random hexamers (NEB) and MMoL V reverse-transcriptase (Invitrogen).

Quantitative PCR.

The SYBR Green PCR Core Reagents Kit (Applied Biosystems, 4304886) was used for all quantitative ChIP PCR on the 7500 Fast RealTime PCR System (Applied Biosystems). The following PCR program was used: AMPErase UNG treatment at 50° C. for 2 min, AmpliTaq Gold activation at 95° C. for 10 min, 40 cycles of denaturation at 95° C. for 10 s, anneal at 58° C. for 5 s, and elongate at 72° C. for 32 s. Each 25-μl reaction included 5 μl of a 1:50 immunoprecipitation dilution, 2.5 μl of 10×PCR buffer, 3 μl of 25 mM MgCl$_2$, 2.0 μl of dNTP blend, 0.25 μl of AmpErase UNG and 0.25 µl of AmpliTaq Gold DNA polymerase. Primers were optimized to concentrations at which they were ~100% efficient or had a standard curve slope of ~−3.32.

The TaqMan PCR Core Reagents Kit (Applied Biosystems, N8080228) was used for the rest of the quantitative RT-PCR primers on the 7500 Fast RealTime PCR System (Applied Biosystems). The following PCR program was used: AMPErase UNG treatment at 50° C. for 2 min, AmpliTaq Gold activation at 95° C. for 15 min, 40 cycles of denaturation at 95° C. for 30 s and anneal/elongate at 59° C. for 1 min. Each 25-µl reaction included 50 µg of cDNA, 2.5 µl of 10×PCR Buffer, 5.0 µl of 25 mM $MgCl_2$, 0.75 µl of dATP, 0.75 µl of dGTP, 0.75 µl of dCTP, 0.75 µl of dUTP, 0.25 µl of AmpErase UNG and 0.25 µl of AmpliTaq Gold DNA polymerase.

The fold gene expression of $Evf2^{+/+}$ and $Evf2^{TS/TS}$ E13.5 MGE tissue was determined by comparing the Ct values of the target gene to the Ct value of the control gene (β-actin) using the following formula: $2^{-(Ct(IP)-Ct(Input))}$.

Electrophysiology.

Transverse hippocampal slices (300 nm) were prepared from 3-5-month-old $Evf2^{TS/TS}$ mice. Slices were cut in ice-cold (~4° C.) oxygenated ACSF and then were allowed to recover for 1-2 h before being transferred to the recording chamber where they were continuously superfused with solution heated to 32-34° C. and saturated with 95% $O_2$/5% $CO_2$. The standard extracellular solution contained 124 mM NaCl, 3 mM KCl, 1.25 mM $KH_2PO_4$, 2.0 mM $CaCl_2$, 1.3 mM $MgCl_2$, 26 mM $NaHCO_3$ and 10 mM glucose. The concentration of $MgCl_2$ was raised to 2.0 mM and that of $CaCl_2$ decreased to 1.4 mM in the slicing solution. To isolate GABAergic current, 20 µM CNQX and 50 µM D-AP5 were added to the standard ACSF. Tetrodotoxin (2 µM) was added to the drug solution to isolate minimal IPSCs.

Somatic whole-cell recordings were obtained from CA1 pyramidal neurons under visual guidance using infrared differential interference contrast microscopy. Patch pipettes were pulled from borosilicate glass capillary tubing (A-M Systems). Internal solution for the patch pipettes contained 120 mM cesium methane sulphonate, 10 mM CsCl, 5 mM NaCl, 10 mM HEPES, 10 mM EGTA, 5 mM TEA-Cl, 4 mM Mg-ATP, 0.3 mM GTP and 5 mM QX-314 (pH 7.3-7.4), adjusted with CsOH, osmolarity 290±10 mOsm.

Voltage-clamp recordings were performed using Axopatch-200B (Axon Instruments). In all of our recordings, series resistance was <22 MΩ and was compensated at 80%. The recorded signal was low-pass filtered at 5 kHz and digitized at 10 kHz with a PCI-MIO-16E-4 board (National Instruments). All data were stored on a PC computer with custom software using C++ Builder 5.0 (Borland) and a NI DAQ 6.5 driver (National Instruments).

Evoked IPSCs were elicited at 0.1-0.07 Hz with a bipolar Pt/Ir electrode (2×25 µn) positioned on the stratum radiatum within 150 µm of the cell being recorded (Schaffer collateral-commisural fibers location site). At the beginning of each experiment, stimulus intensity was adjusted to evoke EPSCs with amplitude of 0.4-0.2 nA. Evoked IPSCs were recorded at holding potential from −70 mV to +20 mV with 10-mV voltage steps after blocking EPSCs with a solution containing CNQX and D-AP5.

Spontaneous IPSCs were analyzed using MiniAnalysis 6.0.3 software (Synaptosoft). All events were manually selected on the basis of their kinetics. Between 250 and 450 individual events were analyzed for each cell. Post-recording analyses of evoked IPSPs were carried out using Clampfit 10 (Axon Instruments). All statistical values were evaluated with Origin 8 (MicroCal Software). Values are presented as mean±s.e.m. Statistical differences were established at P<0.05 using the Student t test, unless otherwise indicated.

Animal Use.

Mice were handled under IACUC approval according to institutional guidelines.

Statistical Analysis. Statistical significance was determined using a variety of different tests, as indicated in individual figure legends, with *P<~0.05, P<0.01, and *P<0.001. Error bars on graphs correspond to s.e.m.

Results:

Trans and Cis-gene Regulation by Evf2 in vivo

Figure 1A:
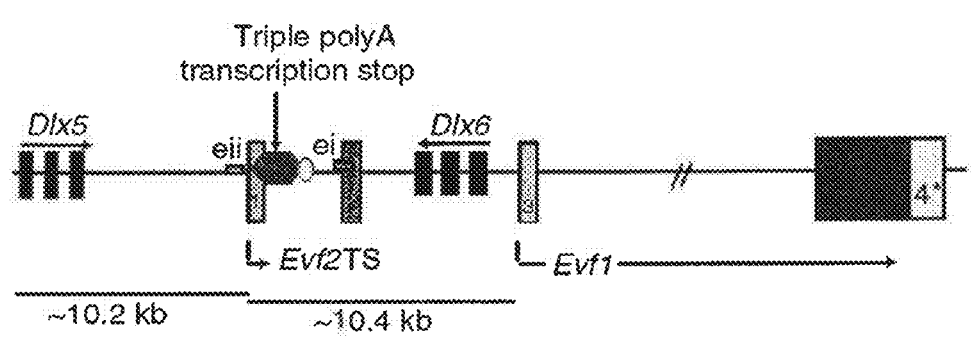
FIGS. 1a-1j.
Figure 1B:
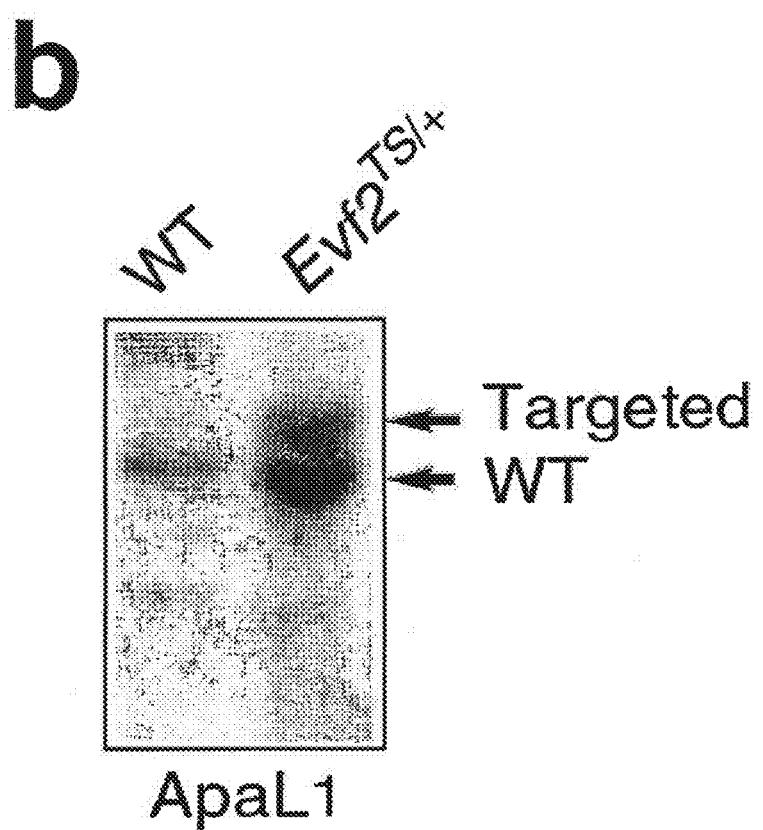
Figures 1C, 1D, 1E, 1F, 1G, 1H:
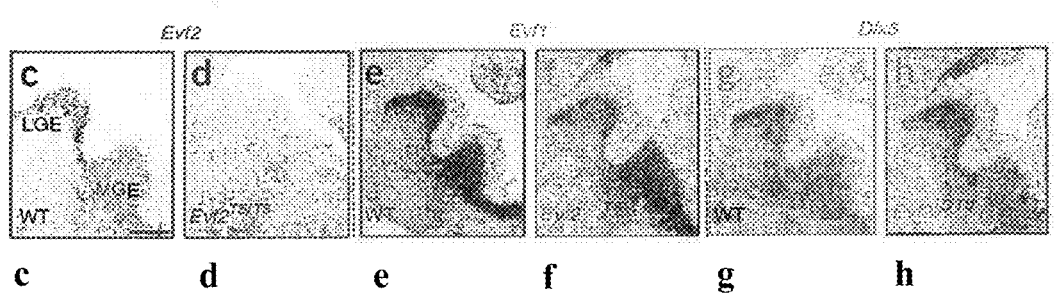
Figures 1I, 1J:
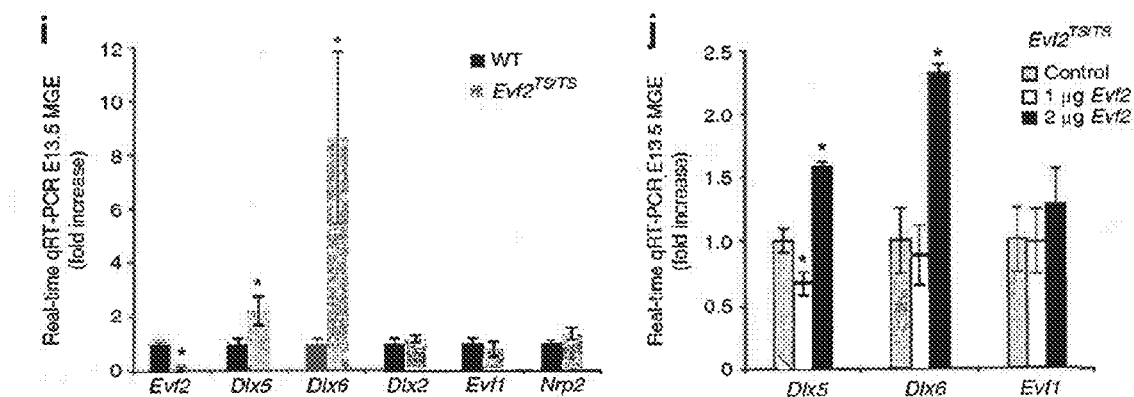

Evf2 loss-of-function mice were developed to determine the role of Evf2 in vivo. Because of the overlap of Evf2 with key Dlx5/6 DNA regulatory elements, transcription termination sites were inserted rather than removing DNA fragments (FIG. 1a). A 19.4-kb fragment spanning the Dlx5, Dlx6 and Evf genes from a mouse BAC were sub cloned. A triple polyadenylation signal (Soriano, (1999)) was then introduced into exon 1 ($Evf2^{TS/TS}$; FIG. 1a). Southern analysis verified correct targeting in embryonic stem (ES) cell lines (FIG. 1b) and mice (data not shown). $Evf2^{TS/TS}$ mutant mice were fertile, lived for at least 1 year and were morphologically indistinguishable from wild-type littermate controls (data not shown). In situ hybridization analysis showed that transcription stop insertion into Evf exon 1 eliminated Evf2, but not Evf1 or Dlx5 expression in embryonic day 13.5 (E13.5) ventral telencephalon (FIG. 1e-h). Realtime qRT-PCR of E13.5 medial ganglionic eminence (MGE) tissue from $Evf2^{TS/TS}$ mice showed that Dlx6 and 5 transcripts increased by eight and twofold, respectively (FIG. 1i). Despite the fact that Evf1 and Dlx5 transcription start sites are approximately equidistant from the triple polyadenylation signal insertion site (FIG. 1a), Dlx5, but not Evf1 transcription was affected in Evf2 mutants (FIG. 1i). Selective transcriptional effects supported the idea that Evf2 loss, rather than insertion of the triple polyadenylation signal sequence, was responsible. If the triple polyadenylation signal insertion were causing the observed transcriptional effects, all Dlx5/6 enhancer activities would be expected to change, including Evf1.

To distinguish between trans and cis-dependent Evf2 RNA regulatory effects, we performed Evf2 electroporation into E12.S $Evf2^{TS/TS}$ brains at two different concentrations (FIG. 1j). At a lower Evf2 concentration (1 µg) Dlx5 expression decreased, whereas Dlx6 and Evf1 concentrations remain unchanged. At a higher Evf2 concentration (2 µg), the concentrations of both Dlx5 and Dlx6 increased, whereas that of Evf1 did not change. The ability of Evf2 to partially rescue Dlx5 increase suggested that Evf2 transregulatory mechanisms were involved in Dlx5 transcriptional control. The inability of ectopically expressed Evf2 to rescue Dlx6 increase in Evf2TS/TS mutants supported the idea that Evf2 reduced Dlx6 expression through anti-sense competition in cis, rather than by trans, mechanisms. At higher concentrations of Evf2 (2 µg), the concentrations of both Dlx5 and Dlx6 increased, supporting previously published results that Evf2 RNA can function as a transcriptional activator of Dlx5 and Dlx6 ei and eii when ectopically expressed (Feng, et al. (2006)). Electroporation of an Evf2siRNA construct into E12.5 brains also increased the levels of Dlx5 transcripts (data not shown), further supporting the idea that an Evf2 trans-acting mechanism regulates Dlx5 expression. Together, these data suggested that Evf2- mediated transcriptional control was concentration dependent, using both trans and cis regulatory mechanisms in vivo.

Evf2 Recruitment of DLX and MECP2 to Intergenic Enhancers

Figures 2A, 2B, 2C, 2D:
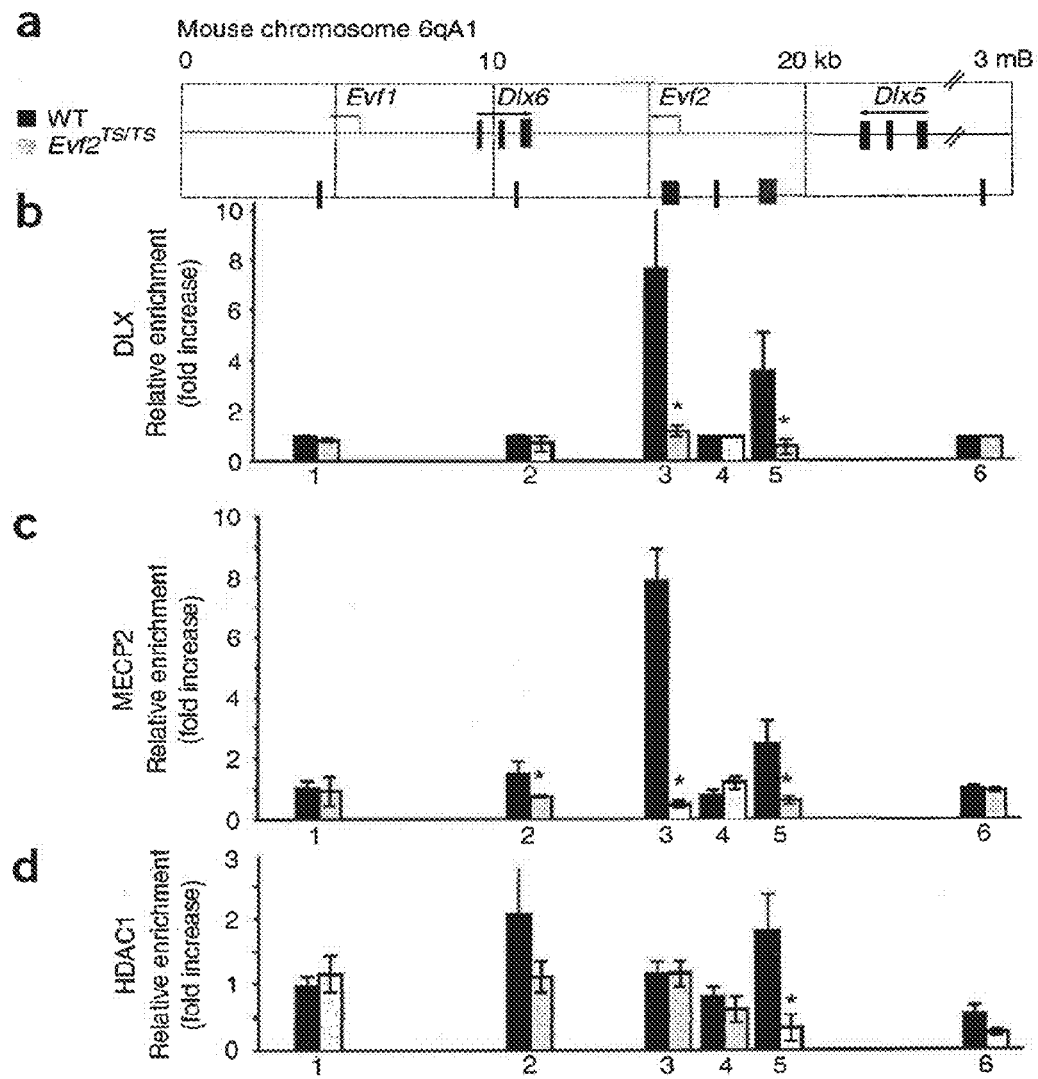
FIGS. 2a-2d provide a graphic representation of the loss of Evf2 affecting DLX and MECP2 binding to Dlx5/6 intergenic enhancers in E13.5 MGE.

It has been shown that Evf2 forms a complex with DLX proteins in vivo and acts as a transcriptional coactivator of DLX activity with both target and homeodomain specificity in C17 cells (Feng et al. (2006)). In addition, a model has been proposed in which Evf2 recruits DLX proteins to Dlx5/6 intergenic enhancers. Here, however, qRT-PCR analysis found that mice lacking Evf2 (FIG. 1i) indicated that the levels of Dlx5 and Dlx6 transcripts increased, suggesting that Evf2 has a negative, rather than positive, transcription-regulating role in vivo. Rescue experiments (FIG. 1j) suggested that increased levels of Dlx6 in $Evf2^{TS/TS}$ mutants resulted from a loss of anti-sense interference in cis, whereas more subtle repressive effects on Dlx5 transcription occurred in trans. To further investigate the mechanism of Evf2-dependent transcriptional control, we used chromatin immunoprecipitation (ChIP) followed by quantitative PCR (ChIP-PCR) on wild-type and $Evf2^{TS/TS}$ mutant E13.5 MGE chromatin to determine whether Evf2 affects DLX binding to Dlx5 and Dlx6 ei and/or eii. Qualitative ChIP assays using antibodies to DLX1 and 2 previously identified Dlx5/6 ei and eii as specific binding sites (Zhou et al. (2004)). In wild-type E13.5 MGE, pan-antibodies to DLX proteins (Feng et al. (2006), Panganiban et al. (1995), Kohtz, et al. (1998), Kohtz, et al. (2001), and Feng et al. (2004)) recognized DLX protein-Dlx5/6 enhancer (ei and eii) complexes (FIG. 2b). In $Evf2^{TS/TS}$ mutant chromatin, DLX did not bind to ei and eii (FIG. 2b), indicating that Evf2 is important for DLX protein recruitment to Dlx regulatory enhancers ei and eii.

Given previous reports that mice lacking both Dlx1 and 2 show reduced expression of Dlx5 and Dlx6 (Anderson, 1997), failure of DLX protein recruitment to Dlx5/6 ei and eii would be expected to decrease Dlx5/6 transcription. However, the number of Dlx5/6 transcripts increased and Dlx2 expression did not change (FIG. 1i). The report that a twofold increase in Dlx5 can occur in the adult prefrontal cortex on loss of the transcriptional repressor Mecp2 (Horike, et al. (2005)) led us to investigate whether loss of Evf2 in the embryonic brain can affect MECP2 binding in the Dlx5/6 region. In the absence of Evf2, MECP2 (Bienvenu, et al. (2006)), a DNA methyl binding protein associated with repressed chromatin, did not bind ei or eii (FIG. 2c). One mechanism that was proposed for MECP2-mediated transcriptional repression is its ability to recruit HDAC, a histone deacetylase responsible for chromatin inactivation (Nan, et al. (1997)). However, loss of MECP2 binding to ei inEvf2 mutants did not alter HDAC binding to ei (FIG. 2d), suggesting that MECP2 binding functions through an alternate mechanism at this site and stage of development. Loss of MECP2 binding at eii did reduce HDAC binding, suggesting that ei and eii differ in how MECP2 function affects transcriptional regulatory activity by these sites. Although site 2 was previously defined as an MECP2- and HDAC-binding site in the adult prefrontal cortex (Horike, et al. (2005)), MECP2 bound minimally to site 2 at this time during development. In addition, HDAC bound to site 2 in wild-type embryonic MGE, but reduction in Evf2TS/TS mutants was not statistically significant (FIG. 2d). Therefore, increased Dlx5 expression in Evf2 mutants may result from a loss of MECP2 binding to ei and eii and subsequent loss of HDAC from eii.

Evf2 recruited DLX and MECP2 to ei and eii, affecting Dlx5/6 enhancer activities in trans on specific nearby genes, such as Dlx5 but not Evf1, and regulating Dlx6 transcription through anti-sense inhibition in cis (FIGS. 1 and 2). Several possibilities may explain how Dlx5, Dlx6 and Evf1 are transcribed in the absence of DLX binding to ei and eii. First, DLX1/2 may only be important for initial activation of Dlx5/6 expression in an Evf2-independent manner; subsequent regulation of Dlx5/6 levels by DLX and MECP2 may then involve Evf2. Second, other DLX-binding sites may compensate in the absence of DLX ei/eii interactions. Third, the major role of DLX1 and 2 may be to prevent MECP2 from binding ei/eii, acting through inhibition rather than as direct activators.

Evf2 Did not Control DLX or MECP2 Nuclear Localization

Figures 3A, 3B, 3C, 3D, 3E, 3F, 3G, 3H, 3I, 3J:
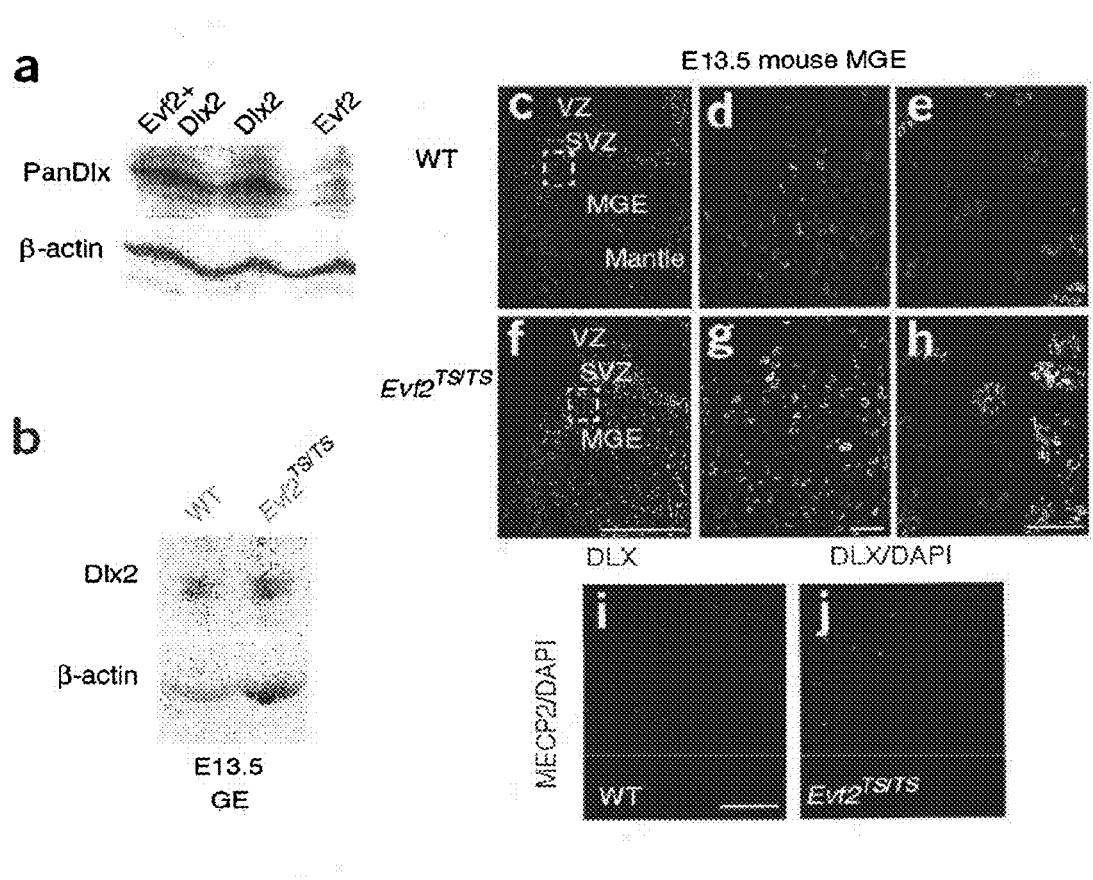
FIGS. 3a-3j provide examples of results indicating that Evf2 does not affect DLX or MECP2 nuclear localization.

The absence of DLX and MECP2 protein binding to ei and eii in Evf2TS/TS mice raised the possibility that Evf2 influences protein stability and/or nuclear localization. In a direct test of the effect of Evf2 on DLX2 protein stability in CI7 neural cells, DLX2 protein levels resulting from co-transfection in the presence or absence of Evf2 did not change (FIG. 3a). In addition, DLX2 protein levels in $Evf2^{TS/TS}$ mutant embryonic ganglionic eminences did not change compared with those of wild type (FIG. 3b). DLX protein distribution in Evf2 mutant nuclei (FIG. 3f-h) was indistinguishable from that in wild type by immunofluorescent visualization (FIG. 3c-e). In addition, transcripts of neuropilin 2 (Nrp2), a direct target of DLX1/2 (Le, et al. (2007)), did not change in $Evf2^{TS/TS}$ mutants (FIG. 1i). If Evf2 were controlling DLX protein stability, all DLX1/2 activities would be affected, including Nrp2, which it is not. These data support a mechanism in which Evf2 recruits DLX to ei and eii, rather than stabilizing DLX protein or directing DLX nuclear localization.

It was next determined whether the loss of MECP2 binding to ei/eii in Evf2 mutants resulted from its effects on nuclear localization. Analysis of MECP2 localization in developing brain shows a gradient of increasing expression in neurons as they mature, with very little expression in immature neurons (Kishi et al. (2004)). However, expression in E13.5 MGE has not been reported. Analysis of MECP2 in E13.5 MGE nuclei in which Evf2 and DLX are normally expressed showed nonhomogeneous, speckled MECP2 localization (FIG. 3i). In $Evf2^{TS/TS}$ mutants, MECP2 distribution is indistinguishable from that in wild type (FIG. 3i, j), indicating that failure of MECP2 recruitment to ei and eii in Evf2 mutants did not result from altered subcellular localization.

Reduced Numbers of $Evf2^{TS/TS}$ Hippocampal Interneurons

The DLX homeodomain protein family is related to the *Drosophila* Distal-less gene (DU)27. Mice lacking Dlx1 and 2 have a substantial loss of GABAergic interneurons in cortex (~75%) and hippocampus (~90%) as a result of defective migration from embryonic MGE (Anderson, et al. (1997), Pleasure, et al. (2000), and Marin, et al. (2003)). Loss of Evf2 affected Dlx5/6 expression and DLX function (FIGS. 1 and 2) in E13.5 MGE, the source of the majority of GABAergic interneuron precursors that will migrate to the hippocampus and dentate gyrus (Pleasure et al. (2000) and Wichterle et al. (2001)). It was then investigated whether GABAergic interneuron development in P2 hippocampus or dentate gyrus was affected in mice lacking Evf2.

Figures 4A, 4B, 4C, 4D, 4E, 4F, 4G, 4H:
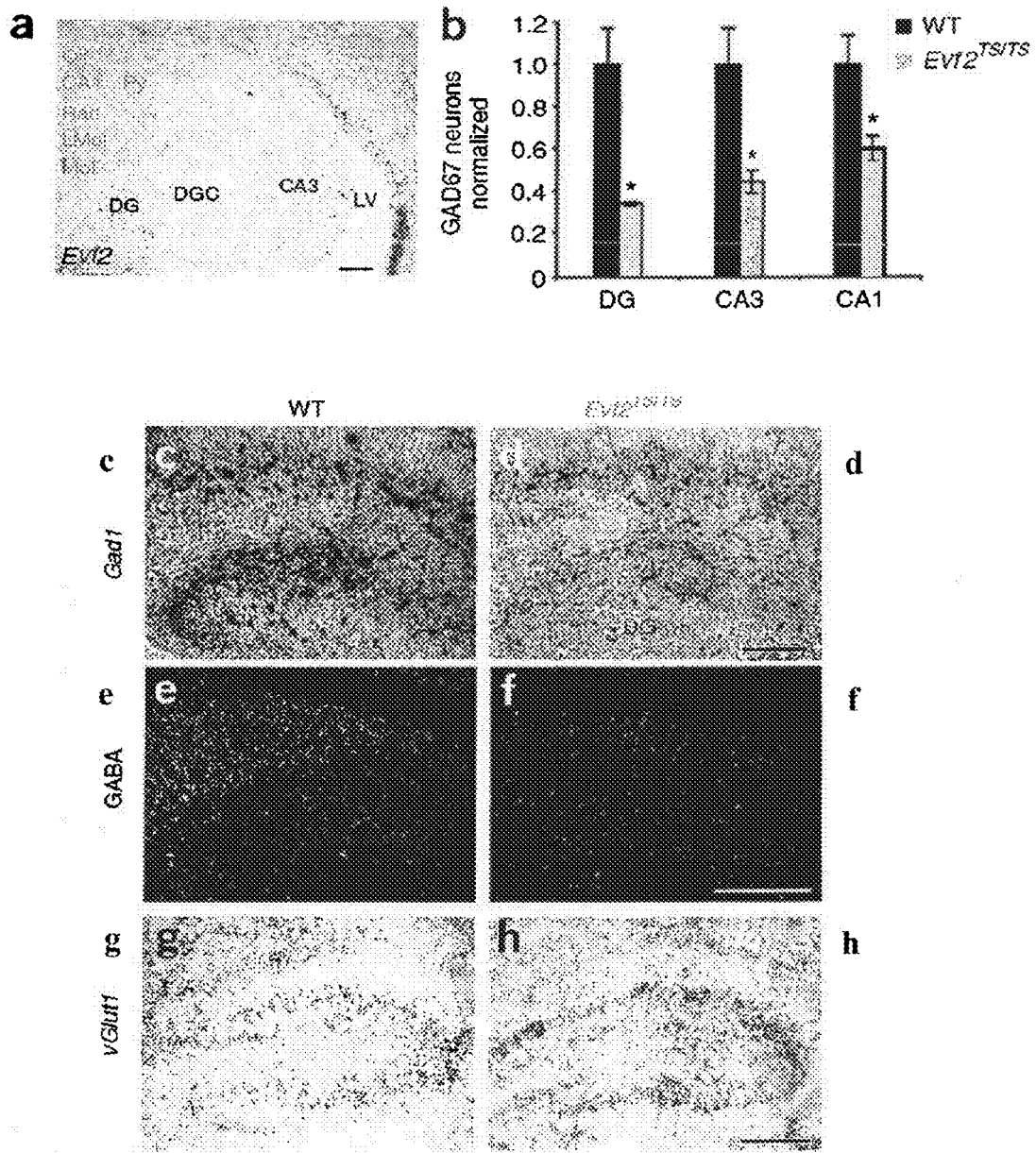
FIGS. 4a-4k provide an example of data supporting GABAergic interneuron loss in the P2 hippocampus and dentate gyrus of Evf2TS/TS mutant mice.
Figures 4I, 4J, 4K:
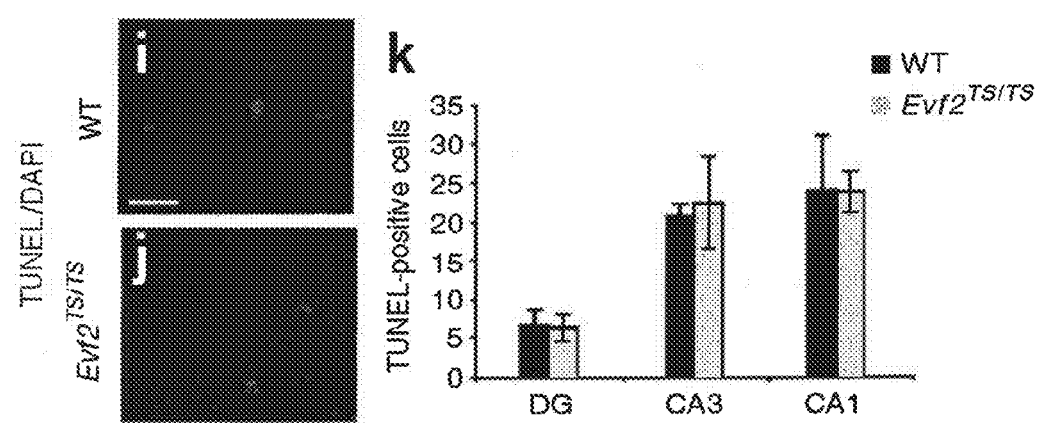

Expression of Evf2 in developing ventral telencephalon/subventricular zone persisted until birth in P2 subventricular zone and cells that appeared to be migrating to the hippocampus (FIG. 4a). However, Evf2 was undetectable in wild-type postnatal day 2 (P2) hippocampus and dentate gyrus, as well as in adult subventricular zone or hippocampus (data not shown). In situ hybridization using a probe against GAD67, an enzyme necessary for converting glutamate to GABA, showed that the number of GABAergic interneurons in Evf2 mutant dentate gyrus and hippocampal CA1 and CA3 layers were reduced by 40-65% (FIG. 4b-d). Reduced Gad1 (the mouse gene coding for GAD67) expression in Evf2 mutants was accompanied by a reduction in GABA, as shown by GABA immunohistochemistry (FIG. 4e, f). In situ hybridization against vesicular glutamate transporter 1 (vGlut1, also known as Slc17a7), a gene expressed specifically in glutamatergic neurons showed that vGlut1 expression in $Evf2^{TS/TS}$ and wild-type hippocampus were similar (FIG. 4g, h). In addition, TUNEL staining of $Evf2^{TS/TS}$ and wild-type hippocampus and dentate gyrus showed similar levels of cell death (FIG. 4i-k). Together, these data indicate that Evf2 is important for proper GABAergic interneuron development and that fate transformation or increased cell death were not responsible for this reduction.

Evf2 Regulated Gad1 in Embryonic, but not Adult Brain

To further understand the role of Evf2 in GABAergic interneuron development, Gad1 RNA levels in E13.5 MGE were analyzed, where GABAergic interneuron precursors first arise. The level of Gad1 transcripts decreased by −30% in $Evf2^{TS/TS}$ compared with wild-type E13.5 MGE (FIG. 5a). Electroporation of Evf2 into $Evf2^{TS/TS}$ E12.5 MGE restored Gad1 levels by −30% compared with a pcDNA control (FIG. 5b). The ability of Evf2 to rescue decreases in Gad1 levels in $Evf2^{TS/TS}$ mutants suggests that Evf2 activates GAD67 transcription through trans-acting mechanisms.

In the forebrain, Evf2 expression was limited to embryonic and early postnatal times of development (FIGS. 1c and 4a) and was undetectable in adult subventricular zone or hippocampus (data not shown). We next asked whether reduced embryonic expression of Gal1 and reduction of GABAergic interneurons seen in early postnatal hippocampus persisted into adulthood. At P60, $Evf2^{TS/TS}$ Gad1 transcript levels were comparable with those in wild type (FIG. 5c). In addition, the number of GABAergic interneurons in 8-month-old Evf2TS/TS and wild-type hippocampus and dentate gyrus were similar (FIG. 5d). This suggests that Gad1 expression and GABAergic interneuron number in Evf2 mutants recovered to normal levels sometime between early postnatal and 2-month-old hippocampal development, temporally correlating with the timing of Evf2 downregulation.

Reduced Synaptic Inhibition in Evf2TS/TS S Pyramidal Neurons $Dlx1^{-/-}$ mice show a loss of a specific population of hippocampal GABAergic interneurons, which subsequently results in reduced synaptic inhibition (Cobos, et al. (2005)). Analysis of $Evf2^{TS/TS}$ hippocampus not only showed a greater percentage loss of total GABAergic interneurons in early postnatal hippocampus (FIG. 4b) than $Dlx1^{-/-}$ mice (Cobos et al. (2005)), but also showed that GABAergic defects appeared earlier. In addition, unlike $Dlx1^{-/-}$ mice, $Evf2^{TS/TS}$ mice showed recovery of GABAergic interneurons in older animals (FIG. 5c, d). This led us to ask whether lower levels of embryonic and perinatal Gad1 can cause long-lasting effects on adult synaptic activity, despite apparent transcriptional recovery.

To answer this question, inhibitory postsynaptic currents (IPSCs) were compared in CA1 pyramidal cells from $Evf2^{TS/TS}$ and wild-type littermates at ages older than P60, when Gad1 mRNA levels have recovered to normal levels. First, we analyzed spontaneous inhibitory postsynaptic potentials (sIPSC) and minimal inhibitory postsynaptic currents (mIPSCs). To maximize outward inhibitory current in artificial cerebrospinal fluid (ACSF) containing glutamate receptor antagonists (20 μM 6-ciano-7-dinitroquinoxaline-2,3-dione (CNQX) and 50 μM D(−)-2-amino-5-phosphonovaleric acid (D-AP5)), recorded at +20 mV. We added tetrodotoxin (2 μM) to isolate mIPSCs (FIG. 6a, b). All mice were divided into two age groups: adult (3-5 months old) and old (<12 months old) mice. The two age groups allowed us to distinguish any persistent differences between mutant and wild-type mice from those that might be attributable to specific developmental stages.

Both $Evf2^{TS/TS}$ age groups showed a significant reduction in sIPSCs event frequency in CA1 pyramidal cells. sIPSC mean frequency in the adult group was lower in mutant mice by 42% compared with those in wild-type mice. In old mice, sIPSCs event frequency in mutant mice was lower by 38% than in wild types. We observed similar significant reductions in mIPSCs event frequencies in adult and old $Evf2^{TS/TS}$ groups compared with wild types. Cumulative probability plots and corresponding Koimogorov-Smimov statistical analysis further confirmed the reduction in IPSC frequency in $Evf2^{TS/TS}$ mice (FIG. 6c, d). In contrast, we did not find significant differences in sIPSP amplitude or mIPSP amplitude between wild-type and mutant mice (FIG. 6e, f). This suggested that Evf2 did not control the properties of synaptic contacts or GABA receptors formed by normally differentiated interneurons, but instead reduced the numbers of GABAergic synapses that formed on CA1 pyramidal neurons.

Notably, the frequency of sIPSCs and mIPSCs were lower in old mice than in adult mice, but the comparable age-dependent changes occurred in both $Evf2^{TS/TS}$ and wild-type mice. Thus, the difference between mutant and wild-type mice persisted. Likewise, the amplitude of sIPSCs increased in old mice. These age differences are consistent with those reported previously (Potier, et al. (2006) and Xu, et al. (2009)).

To further determine whether inhibitory input in CA1 pyramidal neurons were altered in the mutants, we measured the evoked IPSCs in CA1 pyramidal neurons from the adult mice group on stimulation of the stratum radiatum. First, we recorded evoked excitatory postsynaptic currents (EPSCs) with amplitude 0.4-0.2 nA at −70 mV, adjusting the stimulus intensity as necessary. Glutamatergic antagonists blocked EPSCs (see above), and a series of evoked IPSCs were recorded at different holding potentials (−70 m V to +20 m V). The I-V plot constructed from these recordings was normalized to the amplitude of evoked EPSCs at −70 m V (FIG. 6g). We included only cells with similar biophysical characteristics in the analysis (wild type, n=5; mutant, n=4). Evoked IPSCs were significantly smaller in mutant mice (P<0.01, paired t test), further suggesting that CA1 pyramidal neurons received less GABAergic innervation.

Finally, we did not find significant changes in the rise or decay times for spontaneous and evoked IPSCs. When added in the recording ACSF, 0.25 mM picrotoxin abolished both spontaneous and evoked IPSCs in all our recordings, confirming the evolvement of $GABA_A$ receptors. Therefore, GABAergic interneuron recovery in older mice did not result in the recovery of normal synaptic inhibition in the hippocampus.

Discussion:

These results indicate that the Evf2 noncoding RNA is important for balanced gene regulation in developing ventral forebrain In Evf2$^{TS/TS}$ mutants, Dlx6 transcripts increased by about eightfold. The inability to rescue increased Dlx6 in Evf2$^{TS/TS}$ mutants supports the idea that Evf2 anti-sense transcriptional inhibition of Dlx6 occurs in cis through opposite-strand transcription rather than anti-sense annealing. Data showing that higher Evf2 levels caused an increase rather than a decrease in Dlx6 (FIG. 1j) support opposite-strand transcriptional inhibition, as would be expected with an anti-sense annealing mechanism. Although it cannot be ruled out that the triple polyadenylation signal insertion, rather than the loss of Evf2 anti-sense interference, resulted in an increase in Dlx6 transcription, it is unlikely that the triple polyadenylation signal insertion disrupted Dlx5/6 ei or eii, given that Evf1 transcription remained unaffected in Evf2$^{TS/TS}$ mutants. Furthermore, the triple polyadenylation signal insertion in the 5' end of the Air noncoding RNA (Sleutels et al. (2002)) does not affect adjacent transcription. Together, these data suggest that in vivo Evf2 transcription, rather than Evf2 RNA, negatively regulated Dlx6 transcription through competitive anti-sense inhibition in cis.

In contrast with its effects on Dlx6, the ability of Evf2 to rescue increased Dlx5 and decreased Gad1 indicated that Evf2 RNA negatively regulated Dlx5 and positively regulated Gad1 in trans. Therefore, Evf2-mediated trans-acting transcription-regulating effects were target and concentration dependent; low levels of Evf2 repressed Dlx5 and higher levels activated Dlx5, Dlx6 and Gad1. These results also support previous data that identified trans-acting transcriptional activation of Dlx5/6 ei and eii by Evf2 (Feng, et al. (2006)). Further support for the idea that Evf2 acts in trans to repress Dlx5 stems from our knockdown studies (Data not shown).

Studies have shown that SHH activates Dlx and Evf genes and an embryonic form of Gad1 in embryonic forebrain (Feng et al. (2006) and Kohtz et al. (1998)). In addition, ectopic expression of Dlx2 and Dlx5 activates Gad1 in embryonic forebrain slices (Stuhmer et al. (2002). Together, these data identify Evf2 and DLX as components of a signaling cascade that activates GAD67, supporting the idea that reduced Gad1 levels in Evf2$^{TS/TS}$ mutants may result from interference with Evf2/DLX regulation of GAD67. However, both our results and previous results do not distinguish whether the loss of Evf2 directly or indirectly affects Gad1 transcription. Of the two known direct targets of DLX1/2 signaling, Evf2 loss affected Dlx5/6 (Zerucha, et al. (2000)), but not Nrp2 (Le, et al. (2007)) (FIG. 1i), indicating that Evf2 did not affect all Dlx1/2 activities. Therefore, it is possible that unidentified targets of Evf2 may be responsible for GAD67 regulation. An important question raised by these experiments is whether Evf2/DLX directly or indirectly regulates GAD67 expression.

Transcription Factor Recruitment by Noncoding RNAs

Our results indicate that the Evf2 trucRNA is important for positive (DLX) and negative (MECP2) transcription factor recruitment to ultraconserved DNA regulatory elements Dlx5/6 ei and Dlx5/6 eii (FIG. 2) in developing ventral forebrain. The loss of Evf2 prevented the recruitment of a known transcriptional activator (DLX) to positively acting DNA regulatory elements (Dlx5/6 ei and eii), with an unexpected increase, rather than decrease, in Dlx5 transcription. Evf2-mediated recruitment of MECP2, a known transcriptional repressor, was lost from both ei and eii and propose that MECP2 loss may explain Dlx5 deregulation. Despite differences between embryonic and adult MECP2-binding sites in the Dlx5/6 region, a twofold increase in Dlx5 in adult brain occurred on loss of MECP2 (Horike, et al. (2005)) and supports a repressive role for MECP2 on Dlx5/6 ei activity. At eii, MECP2 loss was accompanied by HDACI loss, suggesting that chromatin in eii was more active in Evf2 mutants, which in turn could increase Dlx5 transcription. However, HDACI binding to ei did not change, suggesting that an alternative regulation mechanism was employed at this site. Recent evidence suggests that MECP2 can act as a transcriptional activator in some cases, associating with CREBI at activated targets (Chahrour et al. (2008)). Our data indicate that MECP2 recruitment is dependent on Evf2, supporting the possibility that trans-acting RNAs may influence the choice between activator or repressor activities, either through co-recruitment of additional factors or by an unknown mechanism.

The mechanism of Evf2-mediated recruitment of MECP2 and DLX proteins was analyzed to determine whether recruitment occurs competitively, equally on both alleles or in a mutually exclusive manner (data not shown). Allelic imbalance causes both subtle (1.5-fold) and marked (ninefold) changes in gene regulation and occurs in 20-50% of tested genes (Cowles et al. (2002), Van et al. (2002), and Doss et al. (2005)). Similarly, it is possible that the level of Evf2 localized at specific alleles may determine the extent or identity of the factor(s) recruited. Previous fluorescent RNA in situ hybridization data support the idea that E13.5 MGE nuclei have heterogeneous distribution of Evf2 between alleles; in an E13.5 MGE section, Evf2 transcripts may be distributed on single, equal double and unequal double alleles (Feng et al. (2006)). We found that DLX and MECP2 were also distributed nonhomogenously among different cells and in MGE nuclei (FIG. 3c-j). These data suggest that unequal distribution of Evf2, DLX and MECP2 may have a role in regulating allelic imbalance in different populations of neuronal precursors, leading to neuronal diversity or phenotypic variation.

In humans, 15-25% of genes participate in anti-sense transcription (Yeiin et al. (2003)); however, there are only a few reports of an in vivo mechanism that employs specific anti-sense transcriptional regulation (Prasanth et al. (2007)). Among these, in vivo roles of anti-sense transcripts have been described for Air (Sleutels, et al. 2002) and Kcnq lot I (Mancini-DiNardo, et al. (2006)) in imprinting control. The data from our Evf2 mutant analysis, combined with that from our rescue experiments, suggests that Evf2, an anti-sense transcript of Dlx6, negatively regulated Dlx6 transcription in cis through opposite-strand transcriptional competition. However, the ability of Evf2 to regulate Dlx5 and Gad1 in trans raises the possibility that anti-sense transcripts may not be limited to cis-acting mechanisms or even to local regulation. Given the number of known anti-sense transcripts in non imprinted regions, it will be important to determine how often anti-sense transcripts have trans-regulatory effects and the role of this regulation in various biological processes.

Noncoding RNA-dependent GABAergic Interneuron Development

The embryonic MGE is regulated by Dlx-dependent mechanisms and produces GABAergic interneuron precursors that will later populate the hippocampus (Pleasure et al. (2000)). The loss of Evf2 resulted in imbalanced gene expression in the embryonic MGE, leading to decreased GABAergic interneurons in early postnatal (P2) hippocampus and dentate gyrus. Furthermore, this decrease in GABAergic interneurons in P2 Evf2 mutants did not result from increased cell death or a cell-fate transformation in the hippocampus (FIG. 4g-k).

There are several possible reasons why GABAergic interneurons may be decreased in P2 Evf2 mutant hippocampus. One possibility is that decreased Gad1 in E13.5 Evf2 mutant MGE reduced GABA levels in interneuron precursors, altering their tangential ventral to dorsal migration and reducing the number of GABAergic interneurons that reach their destination in the hippocampus. This is supported by reports that GABA affects neuronal migration in multiple contexts (Heng et al. (2007)), including tangential migration from MGE to cortex (Cowles et al. (2002), Cuzon et al. (2006), and López-Bendito (2003)). In addition, the interference with DLX1/2 activity that was seen in Evf2 mutants would be expected to impair GABAergic interneuron migration from E13.5 MGE (Anderson et al. (1997) and Pleasure et al. (2000)). If the majority of GABAergic interneurons derive from embryonic and early postnatal ventral sources that are defective in Evf2 mutants, there are again several possibilities of how GABAergic interneuron numbers recover in the adult Evf2 mutant hippocampus. One possibility is that the Evf2 mutant adult compensates by neurogenesis of GABAergic interneurons in either the hippocampal subgranular zone or rostral subventricular zone. If so, it is clear from our electrophysiology experiments that these neurons were not functionally equivalent at the synaptic level to their embryonically generated counterparts. An alternate possibility is that GABAergic precursors in Evf2 mutants migrated at the appropriate time and to the proper destination, but produced lower levels of Gad1 in the absence of Evf2. If migration defects are found, future experiments may be needed to investigate why the numbers of GABAergic interneurons decrease at P2, how they eventually recover and what is the basis for their synaptic defects.

SHH signaling in the embryonic ventral forebrain initiates a transcriptional cascade that involves DLX proteins, Evf2, MECP2 and GAD67 for proper GABAergic interneuron development (data not shown). Although a large body of literature suggests that the postnatal effects of MECP2 are likely to be critical for Rett syndrome (Guy, et al. (2007) and Giacometti (2007)), our results raise the possibility that Evf2 loss and MECP2 loss share a common mechanism, in which transcriptional effects in embryonic MGE cause adult GABAergic defects at the synaptic level. Efforts to identify single or multiple targets of MECP2 in the etiology of Rett syndrome have been inconclusive. Controversial evidence has raised the possibility that deregulation of Dlx5 in adult Mecp2$^{-/-}$ brains may be responsible for GABAergic defects (Horike et al. (2005) and Schule et al. (2007)). However, analysis of Evf2 mutants reveals that the correlation between MECP2 loss, increased Dlx5 and GABAergic defects may be indirect.

Given that DLX5 is an activator of GAD67 (Stuhmer et al. (2002)), GABAergic interneuron loss would not be a predicted effect of the twofold Dlx5 increase in Evf2 mutants. In fact, Evf2 rescue experiments suggested against Dlx5 upregulation as a cause for GABAergic defects in Evf2 mutants and suggested that the mechanism involved in Evf2 regulation of Dlx genes is separate from Evf2 regulation of GAD67. Our rescue experiments suggested that Evf1 controls Gad1, Dlx5 and Dlx6 through distinct trans and cis mechanisms. In addition, at the 2 µg Evf1 rescue concentration, Dlx5 increased while GAD67 was rescued. If a twofold Dlx5 increase were the cause of GABAergic defects, GAD67 would not be expected to increase. These experiments suggest that Gad1 reduction, rather than increased Dlx5, is more likely to cause GABAergic interneuron defects.

To the best of our knowledge, these findings describe the first demonstration that an ncRNA-dependent mechanism is important for early GABAergic interneuron development can determine GABAdependent connectivity in the adult brain. The inability to recover proper connectivity, regardless of restored Gad1 and GABAergic interneuron number in adult brain, reinforces the idea that important factors in the developing embryo influence GABAergic interneuron function in adult. This is especially important given the long-standing question of whether mental disorders, in the absence of apparent physiological adult deficits, can result from altered embryonic development.

These data indicate that Evf2 TS/TS mice will not only be useful for studying the normal development of GABAergic interneurons, but will also shed light on the etiology of autism and learning behavior. Such a mouse model may be used to test potential therapeutic agents for effectiveness for preventing or treating a wide range of brain disorders such as autism including autism spectrum disorders, learning disorders, memory disorders, and social disorders.

Example 2

Preparation and Characterization of Evf1 Mutant Mice

An Evf1 mutant was prepared using similar techniques as for the preparation of the Evf2 mutant, by inserting a transcription stop sequence into the Evf sequence. For the preparation of the Evf1 mutant, the TS sequence was inserted into exon 3 of the Evf sequence, one (I) nucleotide from the start of Evf exon 3. The flanking sequences used were as follows: TCA AAG ATG GAC TGG [TS] GGA AAG ACA TTA AGT (SEQ ID NO: 50)

The largest possible Evf1 transcript in Evf1 TS/TS mice therefore would be 1 nt long.

A BAC containing the Evf1 exons upstream of the Dlx 5/6 region (schematized in FIG. 19) was constructed, electroporated into ES cells, and cells screened for single copy, non-homologous recombination by PCR and Southern. Dlx 6 was replaced by ER-cre-IRES-GFP in order to deliver a cytoplasmic form of tamoxifen-inducible ere and mark cells containing the rescue construct with GFP. A triple polyA site was inserted into the 5 prime end of exon3, flanked by loxP sites, using the sequence described above. Crosses were made with Evf1 TS/TS×Evf1 rescue, and tamoxifen treatment is performed at E9.5, E17.5, or P30. Adult brains at P60 were then analyzed for PFC expression of D2 receptor, pDyn, and GAD67 as disclosed above.

One of the most dramatic effects of loss of Dlx 1/2 in mice is ~90% reduction of GABAergic interneurons that migrate from the embryonic ganglionic eminences (MGE and CGE) to the hippocampus (Pleasure et al. 2000). In situ hybridization analysis shows that Evf-1 and Evf-2 are expressed along with Dlx genes in postnatal hippocampus, with Evf1 expression persisting in the adult (FIG. 11). At P2, Evf-1 and Evf-2 expression overlap in SVZ and dorsally migrating cells. Similar to Dlx-1 and 5, Evf-2 is expressed at P12 in subventricular zone cells as they exit and migrate dorsally along the external capsule. Evf-1 and Dlx-6 are not detected in these cells at this stage. However, Evf-1 and Dlx-6 are expressed within the P60 hippocampus; the radiatum (Rad) is enriched in Evf-1 expression. Dlx-2 expression was not detected at either of these ages in the hippocampus. Interestingly, it has previously been reported that the earliest expression of Dlx-2 in the embryonic hippocampus (E15.5) is enriched in the stratum radiatum and cell density in this layer is decreased in Dlx 1/2–/– mice (Pleasure et al. 2000). GABAergic interneurons in the stratum radiatum are most affected in the Dlx 1/2–/– mice (Pleasure et al. 2000).

Important roles for Dlx genes in GABA and tyrosine hydroxylase expressing olfactory bulb neurons have also been demonstrated (Qui et al., 1995, Bulfone et. al. 1998, Long et al. 2003). FIG. 12 shows that Dlx genes overlap with Evf1, but not Evf2 in post-natal olfactory bulb.

Analysis of Evf1 and Evf2 in the developing ganglionic eminences shows overlapping expression patterns in the subventricular zone (Kohtz and Fishell 2004, Feng et al. 2006). However, only Evf1 is expressed in postnatal hippocampus and olfactory bulb. In addition to the olfactory bulb, progenitors from the lateral ganglionic eminence migrate to the olfactory tubercle (Wichterle et al. 2001), a region that exhibits a greater response to cocaine than the nucleus accumbens (Ikemoto). FIG. 13 shows that Evf1 expression persists in postnatal day 12 and adult olfactory tubercle, whereas Evf2 expression is not detected. Evf1 expression overlaps with GAD67 expressing neurons, in the Islands of Calleja, and in large nuclei similar to where dopamine receptor 3 expression has previously been shown to be concentrated.

In addition to the hippocampus, another region that is populated by GABAergic progenitors migrating from the embryonic medial ganglionic eminence is the cortex. Examination of the adult dorsal medial frontal cortex (also known as the PFC) shows that the total GABAergic interneuron numbers decrease in Evf1 TS/TS compared to wild type controls (FIG. 14). This is accompanied by a dramatic increased number of neurons expressing D2 receptors, as well as decreased numbers of neurons expressing prodynorphin (pDyn), both indicators of altered dopamine signaling. Since D2 receptor activation and GABA converge on the same pathway, it is possible that increased expression of D2 receptors may result from reduced GABA in this region. Whether D2 receptor activation occurs in the remaining GABAergic interneuron population as a result of a compensatory mechanism in response to reduced GABAergic signaling can also be determined.

The mutant mice are also analyzed for an altered cocaine response. Given that Evf1 TS/TS brains exhibit altered GABAergic/dopaminoceptive signaling in regions known to regulate drug response and reward, Evf1 TS/TS mutants were tested for an altered cocaine response. An unbiased conditioned place preference (CPP) assay was performed using 5.0 mg/kg cocaine, the threshold dose normally required to elicit a weak response in wild-type animals. At this 5.0 mg/kg cocaine dose, Evf1 TS/TS mice (blue) exhibit a preference for the cocaine side, whereas Evf1+/+wild-type littermates (yellow) do not exhibit a preference for the cocaine side (FIG. 15). Additional tests may be performed using an increased number of animals tested in CPP to 15, as well as different drug (cocaine) doses. While it is possible that higher cocaine doses (7 mg/kg) will mask the differences between Evf1 TS/TS and wildtype mice, it is also possible that they will generate more significant differences. Increased CPP response at lower doses would further support that Evf1 loss increases cocaine potency. In FIG. 16, a mechanistic model for increased cocaine potency in Evf1 TS/TS mice is proposed. This data further supports the link between Evf1-dependent control of specific neuronal subpopulations and cocaine response.

Example 3

Summary of Results

Two developmentally and spatially restricted, non-coding RNAs (Evfs) with overlapping expression patterns with the Dlx 5 and 6 homeobox genes have been identified. Like the Dlx genes, Evfs are targets of the key signaling protein, Sonic hedgehog. In cooperation with Dlx-2, Evf-1 or 2 can transcriptionally activate the mouse and zebrafish Dlx 5/6 and 4/6 enhancers. This cooperative effect on the Dlx 5/6 enhancer is both target specific, as well as limited to Dlx homeodomain containing proteins. Although the expression of Evfs and Dlx 5/6 overlap in the developing ventral forebrain, and post-natal subventricular zone, they diverge in hippocampus, olfactory bulb, and olfactory tubercle after birth. The close functional and developmental association between Evfs and Dlxs during development suggest that Evfs playa role in Dlx 5/6 regulation in vivo, and that disruption of this regulation may result in alterations in developmental processes known to be disrupted in Dlx mutant analysis.

Phenotypic analysis of Evf2 loss of function mutants is consistent with reduced Dlx 1/2 signaling. While loss of function Evf2 mutants are morphologically indistinguishable from wild-type littermate controls, reduced numbers of GABAergic interneurons in postnatal day 2 hippocampus and dentate gyrus are observed. Evf2 mutants exhibit reductions in GAD67 expressing interneurons in postnatal olfactory bulb, with variability between embryos (not shown). In postnatal day 2 Evf2 mutants, the ventral Evf1 SVZ domain is expanded (not shown).

However, real-time qRT-PCR and qCHIP-PCR show that loss of Evf2 up-regulates Dlx 5 and Dlx 6, despite a failure of Dlx proteins to be recruited to the ei and eii enhancers. FIG. 17 proposes a model to explain how recruitment of both positive and negative transcription factors to Dlx 5/6 intergenic enhancers may explain Dlx 5/6 increase upon Evf2 loss. The foregoing data supports that (1) the Evf2 RNA regulates enhancer activity through recruitment of positive (Dlx) and negative (Mecp2) transcriptional regulators; (2) Dlx proteins promote Dlx 5/6 ei and eii regulated transcription by preventing Mecp2 binding; and (3) Mecp2 represses Dlx 5/6 gene expression by preventing Dlx transcription factor binding.

FIG. 18 provides one model to explain the role of Evfs in GABAergic interneuron development. It is well established that Shh from the ventral midline induces Dlx genes and Evfs in the embryonic ganglionic eminences. Loss of Dlx genes has been shown to result in significant loss of GABAergic interneurons that originate in the ganglionic eminences. This invention shows, in part, that Evf2 loss results in the loss of a subpopulation of GABAergic interneurons from the hippocampus and olfactory bulb. Together, these data suggest that Evf2 controls Dlx genes by regulating both expression and activity, and that the proper balance of Dlx's and Evf's are important for the development of subpopulations of GABAergic interneurons.

Evf1 TS/TS mice exhibit loss of GABAergic interneurons in a different region, the adult PFC, accompanied by discloses the respective embryonic and adult roles of Evf1-non-coding RNA control of interneurons involved in cocaine response.

Example 4

Additional Analysis of Evf1 Mutants

Additional analysis is conducted to further support that Evf1 in the developing brain produces imbalanced signaling in the adult brain leading to increased susceptibility to psychostimulants, such as cocaine. Such additional analysis is conducted to provide further support for Evf1 being an important factor for proper formation of a subset of GABAergic interneurons in the prefrontal cortex. In addition, it may provide further support that GABAergic interneuron loss in Evf1 mutant prefrontal cortex results from defective migration of precursors during development. Furthermore, it may provide further support that embryonic expression of Evf1 plays an important role in GABAergic and dopamine balance in the adult prefrontal cortex and that embryonic expression of Evf1 controls adult increased susceptibility to psychostimulants such as cocaine.

Thus, one set of additional investigations may be used to determine the effect of Evf1 loss on specific neuronal populations in brain regions involved in cocaine response. Analysis of adult Evf1 TS/TS PFC shows that the number of GABAergic interneurons and prodynorphin-expressing neurons are reduced, whereas the number of D2 receptor-expressing cells is increased. This supports the idea that Evf1 is involved in maintaining balanced GABAergic and dopamine signaling in the PFC.

The following experiments may be performed to further characterize and support the cellular changes that cause altered GABAergic and dopaminoceptive signaling in Evf1 mutant PFC:

1: Characterize Different GABAergic Interneuron and D2 Receptor-expressing Populations in the Evf1TS/TS Adult Prefrontal Cortex.

In the developing brain, analysis of Dlx 1/2 double mutant mice reveals ~75% reduction of GABAergic interneurons in the cortex and nearly complete loss (~90%) from the hippocampus with the exception of the dentate granule cell layer (Anderson et al., 1997, and Pleasure et al. 2000). The hippocampus is more severely affected than cortex in both Dlx 1/2 double and Dlx 1 single mutant analysis (Cobos et al. 2005). In addition, Dlx 1 single mutants exhibit subtype-specific loss of GABAergic interneurons in the hippocampus. Dlx 5−/− mice display decreased GABAergic and dopaminergic neurons in the olfactory bulb (Long et al. 2003). Analysis of GABAergic interneuron migration to the cortex and hippocampus has not been reported for Dlx 5/6−/− mice, presumably because these mice exhibit severe brain deformities. The following lines of evidence support a role of Evf1 in GABAergic interneuron development in the PFC (1) Evf1 is expressed in the E13.5 MGE, where GABAergic interneuron precursors that will populate the PFC are generated; (2) Homotypic transplantation experiments using labelled progenitors from E13.5 MGE transplanted into E13.5 MGE show that the MGE gives rise to cortical GABAergic interneurons (Wichterle et al. 2001); and (3) Evf1 TS/TS adult PFC contains reduced numbers of GABAergic interneurons (disclosed herein).

Procedure: RNA in situ hybridization (RISH) for GAD67, an enzyme required for the conversion of glutamate to GABA, identifies GABAergic interneurons. In FIG. 18, GAD67 RISH of Evf1 TS/TS adult PFC shows a reduction in the number of GABAergic interneurons. However, since the majority of GABAergic interneurons remains, the question of whether all GABAergic interneuron subtypes are slightly reduced, or a specific subtype is preferentially lost, as reported for Dlx 1−/− hippocampus (Cobos et al. 2005) remains. Evf1 TS/TS and wild type littermate control PFC sections will be examined for GABAergic interneuron subtype-specific expression of parvalbumin (PV), neuropeptide Y (NPY), and somatostatin (SOM) using previously characterized antibodies. At least two fields from 4 sections in 3 different brains will be counted for each genotype. Counting will be determined at the same relative rostral/caudal position as determined by Bregma coordinates and morphological criteria, at the level of the dorsal medial frontal cortex, as defined by the mouse brain atlas (Paxinos). In addition, D2 receptors in the PFC have been shown to be expressed by GABAergic interneurons (Mrzljak et al. 1996). Therefore, RISH for GAD67 combined with immunohistochemistry for D2R will be used to determine if ectopic activation of D2 receptors occurs on remaining GABAergic interneurons.

Evf1 may act similarly to Evf2 to affect a subset of Dlx 1/2-dependent transcriptional events in the embryonic ganglionic eminences, and these experiments may determine whether GABAergic interneuron loss in the Evf1 TS/TS adult PFC restricted to a specific subtype.

One possibility is that Evf1 loss reduces the number of subtype-specific GABAergic interneurons reported to be lost in Dlx 1−/− hippocampus (NPY+, SOM+, PV−). It is also possible that Evf1 affects transcription factors other than Dlx 1/2 and its targets. In the latter case, multiple GABAergic interneuron subtypes will be affected. In addition, loss of adult Evf1 expression is likely to play an unknown role in GABAergic interneuron function and/or maintenance. It is possible that adult Evf1 expression is necessary for the survival of specific GABAergic interneurons. Definition of the exact sub-type(s) of GABAergic loss will aid in understanding the imbalanced signaling defects that appear in the PFC of adult Evf1 TS/TS brains.

The outlined investigation may also assist in determining whether D2 receptor activation occur in GABAergic interneurons.

Protocols for anti-NPY, SOM and PV have already been established. However, characterization of the subtype or total loss of GABAergic interneurons may not reveal why such a loss occurs. Therefore, in addition to characterizing subtypes, it may also be determined whether GABAergic-specific or neuron-specific changes in cell death occur in the adult PFC, as previously shown by Tunel staining in Dlx 1−/−mutants (Cobos et al. 2005). Tunel staining, an indicator of cell death that detects DNA fragmentation, in Evf2 mutant hippocampus does not detect differences when compared to wt controls (FIGS. 14i-k).

Determine the Developmental Timing of Gabaergic Loss, Decreased pDyn, and Activation of D2 Receptor Expression in the PFC of Evf1 TS/TS mutants.

In order to further investigate how GABAergic/dopaminoceptive imbalance occurs, it may be determined when these changes are first detected. Evf1 is first expressed at E11.5 in the telencephalic subventricular zone (Kohtz and Fishell, 2004), and is expressed in E13.5 MGE GABAergic precursors as they first migrate to the cortex. At E17.5, GAD67 expressing interneurons can be detected in different cortical layers. Although the exact time that ventral to dorsal migration stops has not been determined, it is thought that by P12, the majority of the migration has occurred.

GAD67, D2 receptor and pDyn RISH are performed on E13.5 and E17.5 telencephalon, and post-natally at P2, P 12 and P30 PFC from Evf1 TS/TS and wild type controls. Established stereological methods of comparisons are utilized, comparing a minimum of 4 sections from 3 different brains at equivalent rostral/caudal positions. In embryonic brains, this is determined by morphological criteria. In post-natal and adult brains, this is not only determined by morphological criteria, but also by distance from Bregma, as defined by the mouse Atlas (Paxinos). Individual neurons can be identified using RISH by each of these probes. Therefore, the numbers obtained are counted using OPEN-LAB software, and compared as shown in FIG. 18 for adult PFC.

Analysis of Evf2 TS/TS GABAergic loss in the hippocampus shows that the reduction of GAD67 expressing interneurons in the hippocampus is not detected until just after birth (FIG. 14 postnatal day 2, E17.5 analysis not shown). In Dlx1−/− mutants, reduced GAD67 numbers are not observed until 2 months old (Cobos et al. 2005). Therefore, in Evf1 mutants, it may be expected that GABAergic loss will be detected postnatally (P12) and not earlier. It is also possible that GABAergic loss will not be detected until adulthood. Since Evf1 is expressed in the adult SVZ and adult cortex, it is possible that new precursors continue to be produced and migrate in the adult brain. Alternately, Evf1 may be important for survival of specific GABAergic interneurons in the adult. Dopamine plays a role in the ventral to dorsal migration of GABAergic precursors (Crandall et al. 2007). Therefore, ectopic D2 receptor activation could occur at anytime during development or postnatally. If D2 receptor increase/pDyn decrease occurs before GABAergic interneuron loss, this would suggest that altered dopamine signaling occurs independent of GABAergic interneuron loss. If D2 receptor increase/pDyn decrease coincide or follow GABAergic interneuron loss, then altered dopamine signaling could be a result of GABAergic interneuron loss. This would be in accordance with the model proposed in FIG. 17 in which increased D2 receptors may occur in response to reduced GABA levels and elevated dopamine.

The experiments as outlined provide further support for when GABAergic interneuron loss is first detected in the Evf1 TS/TS cortex, as well as when does altered dopamine signaling occur in relation to decreased GABAergic signaling in Evf1 TS/TS mice.

RISH using these probes and different stages of development have previously been performed. If it is found that GABAergic interneuron loss is only detectable in adult cortex, this does not necessarily mean that embryonic perturbations do not contribute to the phenotype. It is possible that slight differences in migration and/or differentiation in the embryo could still be responsible for the phenotype. A conditional rescue experiment may be conducted as disclosed below to address this issue. However, the experiments may aid in determining the relationship between GABAergic interneuron loss and increased D2R expression.

If altered dopamine signaling in the cortex is not detected during embryonic stages, it is still possible that it occurs independently of cortical GABAergic interneuron loss. Given that Evf1 is expressed in the post-natal olfactory bulb, changes in the numbers of olfactory bulb dopaminergic neurons that innervate the olfactory tubercle may indirectly affect cortical dopamine signaling. In order to test this possibility, the number of dopamine neurons in the Evf1 TS/TS olfactory bulb in Evf1 TS/TS mutants may be compared to wild-type control. The adult olfactory bulbs of Evf1 TS/TS and wildtype littermate control mice are stained for tyrosine hydroxylase (TH), an enzyme important for generating dopamine, and specific to dopaminergic neurons. Both anti-TH and TH RISH are performed in order to confirm that cell bodies express TH at the mRNA level. While dopaminergic loss or gain from olfactory bulb neurons is possible, the effects of this loss would indirectly affect dopamine signalling in the PFC.

Determine the Effects of Evf1 Loss on Migration from the Medial Ganglionic Eminence to the Cortex.

Disruptions in neuronal fate specification, differentiation and/or migration in the MGE results in altered GABAergic interneuron numbers in the cortex. The first demonstration that cortical interneurons are generated from this ventral to dorsal migration event came from the characterization of the Dlx 1/2 double knock out mouse (Anderson et al. 1997). Subsequently, migration from the E13.5 MGE to cortex was shown in vivo by homotypic transplantation experiments (Wichterle et al. 2001). As disclosed herein Evf1 loss results in a reduction of GABAergic interneurons in the PFC. In this regard, experiments may be designed to test whether this loss results from reduced ability of MGE-derived GABAergic precursors to migrate to the cortex.

Ultrasound-guided (ultrasound biomicroscope, UBM), homotopic transplantation injections of actGFP labelled progenitors derived from E13.5 Evf1 TS/TS or wild-type MGE will be performed and transplanted into wild-type E13.5 recipients, as previously described (Wichterle et al. 2001). The cortex will be co-stained with anti-OFP and anti-TUJ1 (pan-neuronal), anti-GFP and anti-GABA (GABAergic interneurons) to determine whether Evf1 plays a role in neuronal migration from the MGE.

A cell non-autonomous effect of loss of Evf1 will be determined by performing the reverse experiment, where wild-type MGE will be transplanted into Evf1 TS/TS, or wild-type E13.5 MGE and GFP labeled neurons in cortex analyzed.

The experiments as outlined add further support for Evf1 control of migration of neurons from the MGE to the cortex. The demonstration that fewer neurons are co-labelled with GFP in the cortex when Evf1 TS/TS MGE donor tissue is used would suggest that Evf1 affects migration of neuronal precursors in the embryo. In addition, if the wild-type LGE donor tissue transplanted into mutant MGE results in failure to migrate to the cortex, this would suggest that Evf1 loss causes a cell-nonautonomous effect on migration.

Ultrasound-guided (UBM) injections of retroviruses into mouse E9.5 brains (Feng et al. 2006, FIG. 2*b*) will be performed, as well as UBM injections of E13.5 MGE precursors into the MGE at E13.5, in vivo (not shown). The results reproduce those of Wichterle et al. (2001) in that transplanted MGE-derived precursors (fluorescently labeled with the dye PKH), but not LGE precursors migrate to the cortex. Evf1 TS/TS mice can be crossed with ActGFP to obtain Evf1 TS/TS-ActGFP donor tissue. Therefore, these mice can be used to perform these experiments. In addition, mutant donor tissue (GFP labelled) may be co-injected with wild-type donor tissue from mCherry mice (Jackson Labs) in order to provide a positive internal control.

It is possible that MGE/cortical migration defects will not be detected in Evf1 TS/TS embryos. The loss of GABAergic interneurons may be due to other mechanisms such as decreased proliferation, increased cell death or altered cell fate specification in the subventricular zone during development, or in adult. Further investigation of this type will be guided by the results from the characterization of different GABAergic interneuron and D2 receptor-expressing populations in Evf1 TS/TS adult PFC, which defines the time at which Evf1 TS/TS phenotypes first appear.

Determine the Effect of Evf-1 Loss on Response to the Psychostimulant Cocaine.

While the mOTu plays an important role in the rewarding effects of cocaine, the PFC has been proposed to play a role in the craving aspects of cocaine addiction. Together with the finding that Evf1 may be involved in balancing GABAergic and dopaminoceptive signaling in the PFC, this raises the possibility that Evf1 mutants may exhibit altered cocaine responses. The following experiments are performed in order to provide further support for an altered cocaine response in Evf1 TS/TS mice:

Compare Cocaine-induced Gene Expression Changes in Evf1 TS/TS and Control Mice.

In the embryonic brain, Evf1 and Evf2 expression are activated in response to Shh signaling (Kohtz et al. 1998, Feng et al. 2006). Signaling factors that activate Evf1 expression in the adult are not known. However, adult expression of Evf1 in the mOTu and cortex raises the possibility that Evf1 responds to external signals in these regions, playing a role in gene regulation. Evf1 may be regulated in response to cocaine administration, or may be involved in regulating genes involved in response. However, determining the relative timing of these events may provide additional information as to the role of Evf1 in cocaine response.

One of the first responses to drug administration is the immediate early gene, c-fos. Therefore, anti-fos immunohistochemistry provides a read-out of the immediate response (after 1 hour) to cocaine exposure. It may identify whether there is a difference between the number or spatial distribution of c-fos expressing cells in different brain regions, with particular attention to the PFC and mOTu of Evf1 TS/TS adult mice compared to wild-type controls after cocaine injection at different concentrations (5, 10, and 15 mg/kg). Since the stress of injection can also have an effect, saline injections will be used as a control to distinguish between stress and drug-dependent effects. Next, RISH will be used to determine if Evf1 expression is altered after cocaine injection, using a time course analysis: 1 hour, 6 hours, and 24 hours. D1 receptor/enkephalin, D2 receptor/pDyn expression are analyzed in the brains of Evf1 TS/TS and wild type controls to determine if there is a differential response to cocaine-induced increased dopamine signaling, with particular focus on PFC and mOTu.

These experiments provide support for the role of Evf1 in the immediate early response to cocaine. C-fos is an early indicator of drug response. Comparison of c-fos expression in the mOTu and PFC of Evf1 TS/TS compared to wildtypes in response to different doses of cocaine determine whether Evf1 loss changes the brain's initial response at the immediate early stage. If dopamine levels are increased in Evf1 TS/TS PFC due to reduced GABA levels and reduced dopamine uptake, then lower doses of cocaine could be sufficient to elicit similar responses in Evf1 TS/TS compared to wt controls.

These experiments may also provide support for the alteration Evf1 expression by cocaine. The loss of Evf1 in the developing brain produces imbalanced signaling in the adult brain that may lead to increased sensitivity to cocaine. Based on the experiments, imbalanced signaling is predicted prior to cocaine exposure, as would be in the case of predisposition. If Evf1 RNA is modulated in response to cocaine exposure, this would suggest an additional level at which the RNA may play a role in drug response, beyond that of predisposition or dose sensitivity. This possibility will be addressed by determining whether Evf1 RNA expression changes in a dose or time-dependent manner, as described in this experiment.

These experiments also may provide support for the role of Evf1 in cocaine-induced alterations in dopamine signaling. In Evf1 TS/TS mice, increased D2 receptor and decreased pDyn expression are indicators of altered dopamine signaling (see FIG. 16). If dopamine increase causes Evf1 TS/TS PFC mis-expression or increased D2 receptors, then it is possible that cocaine injection will further increase dopamine levels, producing a super-sensitive state. However, the relationship between D2 receptor expression and dopamine is clearly dependent on context, as decreased D2 receptor expression occurs in the striatum of dopamine transporter−/− mice exhibiting 100 times more extracellular dopamine than control (Giros et al. 1996). Although it is likely that Evf1 TS/TS and control brains will differ in their response to cocaine, and possibly a difference between mOTu and PFC responses as well, the exact nature of these will depend on the nature of the imbalance of GABA and dopamine caused by Evf1 loss.

In order to study effects of Evf1 loss on cellular responses to cocaine, Evf1, D1 and D2 receptors, pDyn and enkephalin are studied using immunohistochemistry and in situ hybridization. Although this gives a spatial resolution to the changes observed, RISH is not a quantitative measure of changes in RNA levels. Real-time qRT-PCR is used to measure cocaine-induced changes in gene expression in the adult mOTu and PFC of Evf1 TS/TS using wild-type littermates as comparison.

Compare Cocaine-induced Locomotor Sensitization in Evf1 TS/TS and Control Mice.

Psychostimulants such as cocaine and amphetamine interfere with dopamine uptake or efflux increasing stereotypy and locomotor behavior (Ritz et al. 1987, Jaber et al. 1995). Injection of cocaine into the mOTu induces robust locomotion and rearing (Ikemoto, 2002). Given the high level of expression of Evf1 in the mOTu, Evf1 mutants may display an altered locomotor sensitization profile from wild-type control animals.

Locomotor sensitization to cocaine assays are also performed. Animals are bred and genotyped, then studied for behavioral analysis. The locomotor sensitization to cocaine tests (Birnbaum et al.) are performed as follows: on the first three days of the locomotor sensitization experiments, mice are injected with saline (i.p.) and then placed individually into a plastic mouse cage (18 cm×28 cm) that is similar to their homecage but which contains a small amount of bedding and is located inside a dark Plexiglas box. For the last 5 days of the locomotor sensitization, the mice are injected with cocaine (5, 10, or 15 mg/kg) and immediately placed into the testing apparatus. The first day of the cocaine injection is the acute activity induced by a cocaine injection. Movement is monitored by 5 photobeams in one dimension (Photobeam Activity System, San Diego Instruments, San Diego, Calif.) for 2 hours, with the number of beam breaks recorded every 5 min. Movement is characterized in three ways: repetitive beam breaks of a single beam is classified as stereotypy, consecutive beam breaks of two or more beams is classified as ambulatory movements, and total beam breaks during each 5 min interval. 15 Evf1 TS/TS mutant and 15 wild type control mice will be used at each dose. Depending on the variability obtained, mice may be increased to 20 for each genotype for statistical significance.

Compare Conditioned Place Preference in Evf1 TS/TS and Control Mice.

Using both self administration and conditioned place preference (CPP) behavioral assays in rats shows that, of different brain regions tested including the nucleus accumbens, the mOTu mediates the most robust rewarding effects of cocaine (Ikemoto, 2003). Given the concentrated expression of Evf1 in the mOTu, Evf1 TS/TS mutant mice may behave differently from control mice in the CPP assay.

Initial CPP assays on Evf1 mutant and wild type littermates (FIG. 15) are performed as follows: The place preference apparatus consists of two distinct conditioning chambers (different colors/patterns on the wall as well as different floor textures) connected by a third small distinct chamber. Location of the animal is determined by 16 photo beams connected to a computer running Med PC IV software (Med Associates, St. Albans, Vt.). On the first day (pretest), the mice are placed into the center chamber and freely allowed to explore all three chambers for 20 min. If an animal shows a strong pretest bias for one chamber, they are excluded from the study. On a subsequent day, animals are injected with cocaine (2, 5, or 7 mg/kg, i.p.) and immediately confined to one chamber for 30 min. The following day the animals are injected with saline (i.p.) and confined to the opposite chamber for 30 min. The drug treatments continue for 4 consecutive days (2 days cocaine alternating with 2 days saline). On the test day mice are placed back into the apparatus in a drug free state and freely allowed to explore all three chambers for 20 min to determine which side they preferred. For data analysis, the time spent in the saline paired chamber is subtracted from the time spent in the cocaine paired chamber, resulting in a preference score for cocaine paired chamber (in sec). 15 Evf1 TS/TS mutant and IS wild type control mice are used at each dose. Alternatively, this number may be raised to 20-25, to obtain statistical significance ($p<0.05$) depending on the variability obtained at different doses. However, the preliminary CPP test at 5 mg/kg and 5 mice in each group produced a $p=0.025$ significance. Therefore, it is expected that n=15 for each genotype will be sufficient to obtain statistically significant data ($p<0.05$).

Evf1 is expressed in the embryonic ganglionic eminences (Kohtz et al. 1998, Kohtz and Fishell, 2004), the source for medium spiny neurons that will populate the mOTu (Wichterle et al. 2001) and GABAergic interneurons that will populate the adult cortex (Anderson et al. 1997). Although RISH analysis does not identify significant changes in numbers of neurons expressing D2, pDyn and GAD67, in the mOTu, Nissl staining shows significant altered morphology of neurons overlapping with GABAergic interneurons. In contrast, characterization of the Evf1 mutant PFC reveals decreased numbers of GABAergic interneurons as well as dopamine signalling. PFC GABAergic interneurons have been shown to express D2 family receptors (Mrzljak et al. 1996). Dopamine binding to D2 receptors results in GABA release, increasing inhibition of firing by pyramidal neurons (Bunney and Aghajanian, 1976). GABA can reduce dopamine release (Dewey et al. 1992), thus providing a self-regulatory mechanism. In Evf1 TS/TS mice, PFC GABAergic interneuron numbers are reduced (FIG. 14), lowering GABA levels. This results in increased levels of dopamine and increased expression of D2R's in a sub-population of neurons. However, it is unlikely that increased GABA release from this subpopulation of PFC interneurons is sufficient to overcome the loss of GABAergic interneurons observed in the Evf1 TS/TS PFC. The Evf1 TS/TS PFC may contain higher levels of extracellular dopamine resulting from reduced GABA. By preventing re-uptake of dopamine, cocaine treatment would further increase extracellular dopamine concentrations in Evf1 TS/TS compared to wt control mice. This model predicts that the concentration of cocaine sufficient for an acute response, as in the locomotor sensitization assay or to elicit cocaine conditioned preference will be lower in Evf1 TS/TS mice than in wt controls. This is in accordance with Dewey et al. (1997), who reported that the GABA agonist GVG, administered 3 hours prior to cocaine, can attenuate locomotor response. The data shown in FIG. 15 support that Evf1 TS/TS mutants show an increased preference for the cocaine chamber in the CPP assay. These effects rely on the nature and extent of the defects in both the mesolimbic and mesocortical pathways.

Evf1 TS/TS mice do not differ from wild-type controls in tests for motor skills. Therefore, motor skill defects will not confound the locomotor or CPP assays. Since the CPP assay has a learning component, differences in learning and memory may contribute to the results. Specifically, animals must remember the chamber where they received the drug in order to return there. If a mutation affects memory, increasing or decreasing this ability, the CPP results may be affected. Evf1 mutants have been found to display increased susceptibility to the effects of cocaine in the CPP assay. Therefore, they can remember where the drug chamber is as well as their wild-type littermates. However, control experiments to directly test the possible contribution of increased or decreased learning and memory abilities in Evf1 mutants are also be performed. Two tests are performed: fear conditioning and Morris water maze. Fear conditioning measures learning and memory by testing the ability of the animal to remember the context or auditory signal associated with a mild electric shock. Testing occurs in two stages: 1) Context Test: 24-48 hrs after training, the animal is returned to the testing chamber and its movement is monitored for 5-10 min for freezing behavior, defined as complete immobility aside from respiration. 2) Cue Test: 24-48 hrs after training, the animal is returned to a modified testing chamber which has a different light source, a plastic insert has been used to alter the texture and size of the arena and a small amount of vanilla is added to the bedding beneath the testing chamber to alter the smell. Mice are allowed to explore the "new" chamber for 3-5 min and then the auditory stimulus is played for another 3-5 min. The freezing behavior of the animals is monitored during the entire session. In the Morris water maze test, animals are trained to locate a hidden platform in a swimming pool over a 10 day period. After removal of the platform, animals are tested for their ability to identify the location of the platform using specific spatial cues. If it is found that Evf1 mutants have decreased learning and memory, but continue to display increased CPP, this would suggest that their memory deficits do not interfere with their ability to remember the location of the chamber. It is possible that Evf1 mutants have increased learning and memory abilities and that this enables them to remember the chamber where they received the drug better than wild-types. In this case, the results of the locomotor assay will aid distinguishing the relative roles of drug response and enhanced memory in the CPP assay. It is also possible that Evf1 mutants will not display increased locomotor sensitivity, but continue to display increased CPP, suggesting that more complex reward-seeking pathways have been affected rather than acute motor response. These positive results would suggest that more complex cocaine reinforcement paradigms could also be used to determine if Evf1 TS/TS mutants exhibit changes in other reward-seeking assays. Specifically, a fixed ratio (3 weeks) followed by progressive ratio (6 days) cocaine self-administration schedule would reveal how hard animals will work to obtain cocaine. Distinguish the Roles of Embryonic and Adult Evf1 on Cortical GABAergic Interneuron Number and Response to the Psychostimulant Cocaine.

Evf1 controls gene expression in the embryonic region responsible for generating the majority of adult cortical interneurons. In addition, Evf1 expression persists in the adult cortex. The following experiments are performed to determine the relative roles of embryonic and adult Evf1:

Determine Whether Embryonic or Adult Evf1 Controls GABAergic Interneuron Numbers in the PFC.

Evf1 is expressed during development and persists in the adult. While the characterization above delineates its embryonic and adult roles, a direct test is to re-introduce Evf1 into the Evf1 TS/TS mutant at different times during development, and test the effects on the Evf1 TS/TS phenotype.

E9.5 is the earliest day used for tamoxifen treatment (TE9.5) of Evf1 TS/TS×Evf1 rescue, as this is 2 days before endogenous Evf1 is first detected in the ventral telencephalon. Rescue, partial or whole, is defined as 1. GABAergic interneuron increase, 2. pDyn increase, 3. D2 receptor decrease. It is expected that TE9.5 treated brains will rescue part or whole of the Evf1 TS/TS phenotype. If similar rescue is observed with TP30 treatment, then it would suggest that adult expression of Evf1 plays a role in maintaining GABAergic and/or dopaminoceptive signaling in the PFC. The experiments provide support for Evf1 expression in the adult PFC playing a role in maintaining balanced GABAergic and/or dopaminoceptive signaling. In addition, the data provides support for determining whether adult expression of Evf1 rescue the phenotype observed upon loss of Evf1.

The Evf1rescue construct may be unable to rescue any aspect of the PFC phenotype observed in Evf1 TS/TS homozygotes, regardless of the timing of administration. This would be the case if the phenotypic results of Evf1 loss derive from cis-acting rather than trans-acting effects of the non-coding RNA in vivo. This is unlikely given that we detect trans-acting transcriptional activities of the RNA in transfection assays (FIG. 8). However, in order to directly address this we have already made an Evf1 rescue transgenic line that expresses Evf1 under Dlx1/2 1a regulatory sequences, as previously defined by Ghanem et al. (2007). If this line successfully rescues the GABAergic interneuron phenotype, then timed conditional rescue using a BAC construct as described above will be possible. However, if the rescue is not possible using the transgenic line, a conditional Evf1 deletion construct will be made (FIG. 20). This construct is electroporated into ES cells, screened by PCR and Southern for homologous recombination, and used to generate germline mice containing a conditionally removed exon 3, removing the critical region of Evf1 as defined in transcription assays. Once heterozygotes are obtained, they are crossed to Evf1 TS/+/ROSA-ERcre mice to generate animals where Evf1 transcription has been stopped at different times using tamoxifen treatment (E9.5, E17.5, and P30). Although the results may be similar to those obtained from the rescue, they have slightly different implications. Both address the question of the significance of the adult vs embryonic roles of Evf1, but the rescue experiments address whether re-expression of Evf1 can compensate for embryonic loss. This is especially important when considering non-coding RNAs as targets for drug therapy.

Determine Whether Embryonic or Adult Evf1 Controls Cocaine Conditioned Place Preference A set of experiments is conducted to determine whether embryonic or adult Evf1 controls GABAergic interneuron loss in the cortex. Depending on the outcome, this raises the question of whether embryonic or adult GABAergic rescue by Evf1 reintroduction also reverses the increased effects of cocaine exhibited by Evf1 TS/TS mice in the CPP assay.

Evf1 TS/TS (embryonic or adult rescue) will be compared with Evf1 TS/TS littermates in the CPP assay as described in more detail above.

Where reintroduction of Evf1 into Evf1 TS/TS mice results in rescued GABAergic interneurons, it is expected that this will reverse the enhanced cocaine effects observed in the CPP assay. If such rescue is possible in the adult, it will suggest that direct manipulation of Evf1 in adults may alter GABA-dependent cocaine responses. If rescue is only possible during development, this would indicate that manipulation of Evf1 in the adult is unlikely to be an effective therapeutic tool. Instead, these studies would suggest that environmental, maternal and/or genetic factors that affect non-coding RNA expression and GABAergic interneurons during development should be a topic of future studies to understand how predisposition to drug susceptibility may be controlled or prevented.

REFERENCES

1. Acampora, D., Merlo, G., Paleari, L., Zerega, B., Mantero, S., Barbieri, O., Postiglione, M. P., Simeone, A., Levi, G., 1999. Craniofacial, vestibular and bone defects in mice lacking the Distal-less-related gene Dlx5. Development 126, 3795-3809
2. Amrein H and Axel R (1997) Genes expressed in neurons of adult male *Drosophila*. Cell, 88:459-469.
3. Anderson S A, Eisenstat D D, Shi L, Rubenstein J L. Related Articles, Links (1997b) Interneuron migration from basal forebrain to neocortex: dependence on Dlx genes. Science 278:474-6.
4. Anderson S A, Qui, M., Bulfone, A., Eisenstat, D., Meneses, J., Pedersen, R., Rubenstein, J. L. (1997a) Mutations of the homeobox genes Dlx-1 and Dlx-2 disrupt the striatal subventricular zone and differentiation of late born striatal neurons. Neuron 19, 27-37.
5. Bejerano G., Pheasant M., Makunin I., Stephen S., Kent W. J., Mattick J. S., Haussler D. 2004. Ultraconserved elements in the human genome. Science 304: 1321-1325.
6. Bienvenu, T. & Chelly, J. Molecular genetics of Rett syndrome: when DNA methylation goes unrecognized. Nat. Rev. Genet. 7, 415-426 (2006).
7. Bierut L J, Madden P A, Breslau N, Johnson E O, Hatsukami D, Pomerleau O F, Swan G E, Rutter J, Bertelsen S, Fox L, Fugman D, Goate A M, Hinrichs A L, Konvicka K, Martin N G, Montgomery G W, Saccone N L, Saccone S F, Wang J C, Chase G A, Rice J P, Ballinger D G Novel genes identified in a high-density genome wide association study for nicotine dependence. Hum Mol Genet. 2007 Jan. 1; 16(1):24-35. Epub 2006 Dec. 7.
8. Boffelli D., Nobrega M A, Rubin E. M. 2004. Comparative genomics at the vertebrate extremes. Nat. Rev. Genet. 5: 456-465.
9. Bulfone A, Wang F, Hevner R, Anderson S, Cutforth T, Chen S, Meneses J, Pedersen R, Axel R, Rubenstein J L. (1998) An olfactory sensory map develops in the absence of normal projection neurons or GABAergic interneurons. Neuron. 2: 1273-82.
10. Caine S B, Negus S S, Mello N K, Patel S, Bristow L, Kulagowski J, Vallone D, Saiardi A, Borrelli E. (2002) Role of dopamine D2-like receptors in cocaine self-administration: studies with D2 receptor mutant mice and novel D2 receptor antagonists. J Neurosci. 2002 22(7) :2977-88.
11. Casarosa, S., Fode, C., Guiellemot, F. (1999) MASH-1 regulates neurogenesis in the ventral telencephalon. Development 126, 525-534.
12. Cassiday, L. A and Maher, L. J. (2002) Having it both ways: transcription factors that bind DNA and RNA Nucleic Acids Research 30: 4118-4126.
13. Centonze D, Picconi B, Baunez C, Borrelli E, Pisani A, Bernardi G, Calabresi P. (2002) Cocaine and amphetamine depress striatal GABAergic synaptic transmission through D2 dopamine receptors. Neuropsychopharmacology; 26: 164-75.
14. Chahrour, M. et al. MeCP2, a key contributor to neurological disease, activates and represses transcription. Science 320, 1224-1229 (2008).
15. Chahrour, M. & Zoghbi, H. Y. The story of Rett syndrome: from clinic to neurobiology. Neuron 56, 422-437 (2007).
16. Chiang, C., Litingtung, Y., Lee, E., Young, K. E., Corden, J. L., Westphal, H., and Beachy, P A (1996). Cyclopia and defective axial patterning in mice lacking Sonic Hedgehog gene function. Nature 383, 407-413.
17. Chomczynski, P. & Sacchi, N. Single-step method of RNA transcription by acid guanidinium thiocyanate-phenol-chloroform extraction. Anal. Biochem. 162, 156-159 (1987).
18. Clemens, K. R., Wolf, V., McBryant, S. J., Zhang, P., Liao, X., Wright, P. E. and Gottesfeld, J. M. (1993) Molecular basis for specific recognition of both RNA and DNA by a zinc finger protein. Science, 260, 530-533.
19. Cobos I, Calcagnotto M E, Vi lay thong A J, Thwin M T, Noebels J L, Baraban S C, Rubenstein J L. (2005) Mice lacking Dlx1 show subtype-specific loss of interneurons, reduced inhibition and epilepsy. Nat Neurosci. 8:1059-68
20. Corbin, J., Gaiano, N., Machold, R. P., Langston, A., Fishell, G. (2000) The Gsh-2 homeodomain gene controls multiple aspects of telencephalic development. Development 127, 5007-5020.
21. Cowles, C. R., Hirschhorn, J. N., Altshuler, D. & Lander, E. S. Detection of regulatory variation in mouse genes. Nat. Genet. 32, 432-437 (2002).
22. Crandall J E, Hackett H E, Tobet S A, Kosofsky B E, Bhide P G. (2004) Cocaine exposure decreases GABA neuron migration from the ganglionic eminence to the cerebral cortex in embryonic mice. Cereb Cortex. 14(6):665-75
23. Crandall J E, McCarthy D M, Araki K Y, Sims J R, Ren J Q, Bhide P G. (2007) Dopamine receptor activation modulates GABA neuron migration from the basal forebrain to the cerebral cortex. J Neuroscience 27:3813-22.
24. Cuzon, V. C., Yeh, P W., Cheng, Q. & Yeh, H. H. Ambient GABA promotes cortical entry of tangentially migrating cells derived from the medial ganglionic eminence. Cereb. Cortex 16, 1377-1388 (2006).
25. Dalley J W, Fryer T D, Brichard L, Robinson E S, Theobald D E, Laane K, Peiia Y, Murphy E R, Shah Y, Probst K, Abakumova I, Aigbirhio F I, Richards H K, Hong Y, Baron J C, Everitt B J, Robbins T W. (2007) Nucleus accumbens D2/3 receptors predict trait impulsivity and cocaine reinforcement. Science 315(5816): 1267-70.
26. Dani, Y. 5. et al. Reduced cortical activity due to a shift in the balance between excitation and inhibition in a mouse model of Rett syndrome. Proc. Natl. Acad. Sci. USA 102, 12560-12565 (2005).
27. Depew, M. I., Liu, J. K., Long, J. E., Presley, R., Meneses, J. I., Pedersen, R., Rubenstein, J. L. R., 1999. Dlx5 regulates regional development of the branchial arches and sensory capsules. Development 126, 3831-3846
28. DePrimo, S. E., Stambrook, P. J. & Stringer, J. R. (1996) Human placental alkaline phosphatase as a histochemical marker of gene expression in transgenic mice. Transgenic Res. 5, 459-466.
29. Dewey S L, Chaurasia C S, Chen C E, Volkow N D, Clarkson F A, Porter S P, Straughter-Moore R M, Alexoff D L, Tedeschi D, Russo N B, Fowler J S, Brodie J D. (1997) GABAergic attenuation of cocaine-induced dopamine release and locomotor activity. Synapse. 25(4):393-8.
30. Dewey S L, Smith G S, Logan J, Brodie J D, Yu D W, Ferrieri R A, King P T, MacGregor R R, Martin T P, Wolf A P, et al. (1992) GABAergic inhibition of endogenous dopamine release measured in vivo with 11C-raclopride and positron emission tomography. J Neurosci. 12(10):3773-80.
31. Di Cristo, G. Development of cortical GABAergic circuits and its implications for neurodevelopmental disorders. Clin. Genet. 72, 1-8 (2007).
32. Doss, S., Schadt, E. E., Drake, 1. A. & Lusis, A J. Cis-acting expression Quantitative trait loci in mice. Genome Res. 15, 681-691 (2005).
33. Drake, R. E.; A. I. Alterman; and S. R. Rosenberg. (1993) "Detection of Substance Use Disorders in Severely Mentally Ill Patients." Community Mental Health Journal 29: 175-192.
34. Dubnau, J., and Struhl, G. (1996) RNA recognition and translational regulation by a homeodomain protein. Nature 379, 694-699.
35. Engelke, D. R., Ng, S.-Y., Shastry, B. S. and Roeder, R. G. (1980) Specific interaction of a purified transcription factor with an internal control region of 5S RNA genes. Cell, 19, 717-728.
36. Erdmann, V A, Barciszewska, M. Z., Hochberg, A., deGroot, N., Barciszewski, J. (2001) Regulatory RNAs. Cellular and Molecular Life Sciences 58: 960-977.
37. Feng, J. et al. Synergistic and antagonistic roles of the Sonic hedgehog N- and C-terminal lipids. Development 131, 4357-4370 (2004).
38. Feng, J., Bi, C., Clark, B., Mady, R., Shah, P., Kohtz, J. D. (2006) The Evf-2 non-coding RNA is transcribed from the Dlx 5/6 ultraconserved region and functions as a Dlx-2 homeodomain transcriptional coactivator. Genes and Development, 20: 1470-1484.
39. Gerfen C R. (1992) The neostriatal mosaic: multiple levels of compartmental organization. Trends Neurosci. 15(4):133-9.
40. Gerfen, C. R. and Wilson, C. J. (1996) The basal ganglia. In Handbook of Chemical Neuroanatomy, 12: Integrated Systems of the CNS, III, 371-468.
41. Ghanem, N., Jarinova O., Amores, A., Long, Q., Hatch, G., Park, B K, Rubenstein, J. L. R., Ekker, M.

(2003) Regulatory Roles of Conserved Intergenic Domains in Vertebrate Dlx Bigene Clusters. Genome Research 13: 533-543.

42. Giacometti, E., Luikenhuis, S., Beard, C. & Jaenisch, R. Partial rescue of MeCP2 deficiency by postnatal activation of MeCP2. Proc. Natl. Acad. Sci. USA 104, 1931-1936 (2007).

43. Gilligan, P., Brenner, S., Venkatesh, B. (2002) Fugu and human sequence comparison identifies novel human genes and conserved non-coding sequences. Gene 294, 35-44.

44. Giros B, Jaber M, Jones S R, Wightman R M, Caron M G. (1996) Hyperlocomotion and indifference to cocaine and amphetamine in mice lacking the dopamine transporter. Nature 379:606-12.

45. Graham D L, Edwards S, Bachtell R K, DiLeone R J, Rios M, Self D W. (2007) Dynamic BDNF activity in nucleus accumbens with cocaine use increases self-administration and relapse. Nat Neurosci. 10: 1029-37

46. Graves, L. E., Segal, S. and Goodwin, E. B. (1999) TRA-1 regulates the cellular distribution of the tra-2 mRNA in *C. elegans*. Nature, 399, 802-805.

47. Guillemot, F. and Joyner, A. (1993) Dynamic expression of the murine Achaete¬ Scute homologue Mash-1 in the developing nervous system. Mech. Dev. 42, 171-185.

48. Guy, J., Gan, J., Selfridge, J., Cobb, S. & Bird, A. Reversal of neurological defects in a mouse model of Rett syndrome. Science 315, 1143-1147 (2007).

49. Hark, A. T. et al. (2000) CTCF mediates methylation-sensitive enhancer-blocking activity at the H19/lgf2 locus. Nature 405, 486-489.

50. Hatchell E C, Colley S M, Beveridge D J, Epis M R, Stuart L M, Giles K M, Redfern A D, Miles L E, Barker A, MacDonald L M, Arthur P G, Lui J C, Golding J L, McCulloch R K, Metcalf C B, Wilce J A, Wilce M C, Lanz R B, O'Malley B W, Leedman P J. (2006) SLIRP, a small SRA binding protein, is a nuclear receptor corepressor. Mol Cell. 22(5):657-68.

51. Heng, J. I., Moonen, G. & Nguyen, L. Neurotransmitters regulate cell migration in the telencephalon. Eur. J. Neurosci. 26, 537-546 (2007).

52. Horike S, Cai S, Miyano M, Cheng J F, Kohwi-Shigematsu T. (2005) Loss of silent-chromatin looping and impaired imprinting of DLX5 in Rett syndrome. Nat Genet. 37:31-40.

53. Hyman S E, Malenka R C, Nestler E J. (2006) Neural mechanisms of addiction: the role of reward-related learning and memory Annu Rev Neurosci. 29:565-98.

54. Hyman S E. (2005) Addiction: a disease of learning and memory. Am J Psychiatry. 162:1414-22.

55. Ikemoto S, Qin M, Liu Z H. (2005) The functional divide for primary reinforcement of D-amphetamine lies between the medial and lateral ventral striatum: is the division of the accumbens core, shell, and olfactory tubercle valid? J Neurosci. 25:5061-5.

56. Ikemoto S. (2002) Ventral striatal anatomy of locomotor activity induced by cocaine, D-amphetamine, dopamine and D1/O2 agonists. Neuroscience. 113:939-55.

57. Ikemoto S. (2003) Involvement of the olfactory tubercle in cocaine reward: intracranial self-administration studies. J Neurosci. 23:9305-11.

58. Ingham, P W., and McMahon, A. P. 2001. Hedgehog signaling in animal development: paradigms and principles. Genes & Development 15: 3059-3087.

59. Jaber M, Cador M, Dumartin B, Normand E, Stinus L, Bloch B. (1995) Acute and chronic amphetamine treatments differently regulate neuropeptide messenger RNA levels and Fos immunoreactivity in rat striatal neurons. Neuroscience. 65(4):1041-50.

60. Juan, V., Crain, C., Wilson, C. (2000) Evidence for evolutionarily conserved secondary structure in the H19 tumor suppressor RNA. Nucleic Acids Research 28: 1221-1227.

61. Kageyama Y. Mengus G. Gilfillan G. Kennedy H G. Stuckenholz C. Kelley R L. Becker P B. Kuroda M I. (2001) Association and spreading of the *Drosophila* dosage compensation complex from a discrete roX1 chromatin entry site. EMBO Journal. 20, 2236-45.

62. Kellendonk C, Simpson E H, Polan H J, Malleret G, Vronskaya S, Winiger V, Moore H, Kandel E R. (2006) Transient and selective overexpression of dopamine D2 receptors in the striatum causes persistent abnormalities in prefrontal cortex functioning. Neuron. 49:603-15.

63. Kelly M A, Rubinstein M, Phillips T J, Lessov C N, Burkhart-Kasch S, Zhang G, Bunzow J R, Fang Y, Gerhardt G A, Grandy D K, Low M J. (1998) Locomotor activity in D2 dopamine receptor-deficient mice is determined by gene dosage, genetic background, and developmental adaptations J Neurosci. 18(9):3470-9.

64. Kishi, N. & Macklis, J. D. MECP2 is progressively expressed in post-migratory neurons and is involved in neuronal maturation rather than cell fate decisions. Mol. Cell. Neurosci. 27, 306-321 (2004).

65. Kohtz, J. D. and Fishell, G. 2004. Developmental Regulation of EVF-1, a Novel Non-coding RNA Transcribed Upstream of the Mouse Dlx6 Gene. Mechanisms of Development Gene Expression Patterns 4: 407-412.

66. Kohtz, J. D., Baker, D. P. Cortes, G., Fishell, G. (1998) Regionalization within the mammalian telencephalon is mediated by changes in responsiveness to Shh. Development 125, 5079-5089.

67. Kohtz, J. D., Lee, H. Y., Gaiano, N., Segal, J. D., Ng, E., Larson, T A, Baker, D. P., Garber, E A, Williams, K. P., Fishell, G. (2001) N-terminal fatty-acylation of Sonic Hedgehog enhances the induction of rodent ventral forebrain neurons. Development 128:2351-2363.

68. Kuwabara T, Hsieh J, Nakashima K, Taira K, Gage F H. (2004) A small modulatory dsRNA specifies the fate of adult neural stem cells. Cell: 19; 116:779-93.

69. Lanz, R. B., McKenna, N. J., Onate, S A, Albrecht, U., Wong, J., Tsai, S. Y., Tsai, M. J., O'Malley, B. 1999. A Steroid Receptor Coactivator, SRA, Functions as an RNA and Is Present in an SRC-1 Complex. Cell 97: 17-27

70. Le, T N, Du, G., Fonseca, M., Zhou, O. P., Wiglell, J T, Eisenstat, o. o. (2007) Dlx Homeobox Genes Promote Cortical Interneuron Migration from the Basal Forebrain by Direct Repression of the Semaphorin Receptor Neuropilin-2. J. Biol. Chem., 282: 19071-19081.

71. Lee M. P., DeBaun, M R, Mitsuya, K., Galonek, H. L., Brandenburg, S., Oshimura, M. et al. (1999) Loss of imprinting of a paternally expressed transcript with antisense oritntation to KVLQT1 occurs frequently in Beckwith-Wiedemann syndrome and is independent of insulin-like growth factor II imprinting. Proc. Natl Acad Sci. USA 96: 5203-5208.

72. Lee, E C, Yu, D, de Velasco, J M, Tessarollo, L., Sing, D A, Court, D., Jenkins, N A, Copeland, N G. (2001) A highly efficient *E. coli* based chromosome engineering system adapted for recombinogenic targeting and subcloning of BAC DNA. Genomics 73: 56-65.

73. Lee, J. T., Davidov, L. S., and Varshawsky, D. (1999) Tsix, a gene antisense to Xist at the X-inactivation centre. Nat. Genet. 21: 400-404.

74. Levi, G., Puche, A. C., Mantero, S., Barbieri, O., Trombino, S., Paleari, L., Egeo, A., Merlo, G. R., 2003. The Dlx5 homeodomain gene is essential for olfactory development and connectivity in the mouse. Mol. Cell. Neurosci. 22, 530-543.

75. Lewis, D. A., Hesturncto. T. & Yolk, O W. Cortical inhibitory neurons and schizophrenia. Nat. Rev. Neurosci. 6, 312-324 (2005).

76. Liu J K, Ghattas I, Liu S, Chen S, Rubenstein J L. (1997) Dlx genes encode DNA-binding proteins that are expressed in an overlapping and sequential pattern during basal ganglia differentiation. Developmental Dynamics, 210, 498-512.

77. Liu J, Wang J, Hu J, Tian B. (2005) A method for aligning RNA secondary structures and its application to RNA motif detection BMC Bioinformatics. 10.1186/1471-21 05-6-89.

78. Liu P, Jenkins N A & Copeland N G. A highly efficient recombineering-based method for generating conditional knockout mutations. Genome Res. 13, 476-484 (2003).

79. Lois C and Alvarez-Buylla A. (1994). Long-distance neuronal migration in the adult mammalian brain. Science 264, 1145-1148.

80. Long J E, Garel S, Depew M J, Tobet S, Rubenstein J L R. 2003. DLX5 regulates development of peripheral and central components of the olfactory system. J. Neurosci. 23, 568-578.

81. Lopez-Bandito, G. et al. Blockade of GABA(B) receptors alters the tangential migration of cortical neurons. Cereb. Cortex 13, 932-942 (2003).

82. Lou X Y, Ma J Z, Sun D, Payne T J, Li M D. Fine mapping of a linkage region on chromosome 17p13 reveals that GABARAP and DLG4 are associated with vulnerability to nicotine dependence in European-Americans. Hum Mol Genet. 2007 Jan. 15; 16(2):142-53. Epub 2006 Dec. 12.

83. Mancini-DiNardo D, Steele S J, Levorse J M, Ingram R S & Tilghman S M. Elongation of the Kcnq lot I transcript is required for genomic imprinting of neighboring genes. Genes Dev. 20, 1268-1282 (2006).

84. Marin O and Rubenstein J L. (2003) Cell migration in the forebrain Annu Rev Neurosci. 26:441-83.

85. Marin O, Anderson S A, Rubenstein J L. (2000) Origin and specification of striatal interneurons. J. Neuroscience 20, 6063-6076.

86. Martinez D, Brott A, Foltin R W, Slifstein M, Hwang D R, Huang Y, Perez A, Frankie W G, Cooper T, Kleber H D, Fischman M W, Laruelle M. (2004) Cocaine dependence and d2 receptor availability in the functional subdivisions of the striatum: relationship with cocaine-seeking behavior. Neuropsychopharmacology. 29(6): 1190-202.

87. Martinho R G, Kunwar P S, Casanova J, and Lehmann R. (2004) A Noncoding RNA Is Required for the Repression of RNApolII-Dependent Transcription in Primordial Germ Cells Current Biology, 14, 159-165.

88. Mattick J S. (2007) A new paradigm for developmental biology. The Journal of Experimental Biology 210, 1526-1547

89. Maxwell I H, Harrison G S, Wood W M, and Maxwell F. (1989) A DNA cassette containing a trimerized SV40 polyadenylation signal which efficiently blocks spurious plasmid-initiated transcription. Biotechniques 7, 276-280.

90. Meller V H, Wu K H, Roman G, Kuroda M I, Davis R L. (1997) roX1 RNA paints the X chromosome of male *Drosophila* and is regulated by the dosage compensation system. Cell 88, 445-457.

91. Mercer T R, Dinger M E, Sunkin S M, Mehler M E & Mattick J S. Specific expression of long noncoding RNAs in the mouse brain. Proc. Natl. Acad. Sci. USA 105, 716-721 (2008).

92. Montzka Wassarman, and K., Storz, G. (2000) 6S RNA Regulates *E. coli* RNA Polymerase Activity. Cell, 101, 613-623.

93. Moretti, P. & Zoghbi, H. Y. MeCP2 dysfunction in Rett syndrome and related disorders. Curr. Opin. Genet. Dev. 16, 276-281 (2006).

94. Mrzljak L, Bergson C, Pappy M, Huff R, Levenson R, Goldman-Rakic P S. (1996) Localization of dopamine D4 receptors in GABAergic neurons of the primate brain.) Nature. 1996 May 16; 381(6579):245-8.

95. Nader M A, Morgan D, Gage H D, Nader S H, Calhoun T L, Buchheimer N, Ehrenkaufer R, Mach R H. (2006) PET imaging of dopamine D2 receptors during chronic cocaine self-administration in monkeys. Nat Neurosci. 9(8): 1050-6.

96. Nan, X., Campoy, E J. & Bird, A. MeCP2 is a transcriptional repressor with abundant binding sites in genomic chromatin. Cell 88, 471-481 (1997).

97. National Association of State Mental Health Program Directors and National Association of State Alcohol and Drug Abuse Directors. National Dialogue on Co-Occurring Mental Health and Substance Abuse Disorders. Alexandria, Va.: NASMHPD and NASADAD, 1999

98. Nemes J P, Benzow K A, and Koob M D. (2000) The SCA8 transcript is an anti-sense RNA to a brain-specific transcript encoding a novel actin-binding protein. Hum. Mol. Genet. 9: 1543-1551.

99. Nery S, Fishell G, Corbin J G (2002) The caudal ganglionic eminence is a novel source of distinct cortical and subcortical cell populations. Nat Neurosci 5:1279-1282.

100. Nguyen V T, Kiss T, Michaels A A, Bensaude (2001) 7SK small nuclear RNA binds to and inhibits the activity of CDK9/cyclin T complexes. Nature 414, 322-325.

101. Ninomiya et al. (1996) Isolation of a testis-specific cDNA on chromosome 17q from a region adjacent to the breakpoint of t(12, 17) observed in a patient with acampomelic campomelic dysplasia and sex reversal. Hum. Mol. Genet. 5: 69-72.

102. Panganiban G. Rubenstein J L. (2002) Developmental functions of the Distalless/Dlx homeobox genes. Development 129, 4371-86.

103. Panganiban G, Sebring A, Nagy L, and Carroll S. (1995). The development of crustacean limbs and the evolution of arthropods. Science 270, 1363-1366.

104. Piazza P V, Rouge-Pont F, Deminiere J M, Kharoubi M, Le Moal M, Simon H. (1991) Dopaminergic activity is reduced in the prefrontal cortex and increased in the nucleus accumbens of rats predisposed to develop amphetamine self administration. Brain Research 567 (1):169-74.
105. Pleasure S J, Anderson S, Hevner R, Bagri A, Marin O, Lowenstein D H, Rubenstein J L. (2000) Cell migration from the ganglionic eminences is required for the development of hippocampal GABAergic interneurons. Neuron 28:727-40.
106. Potier B, Jcwenceau A, Epelbaum J & Dutar P. Age-related alterations of GABAergic input to CA1 pyramidal neurons and its control by nicotinic acetylcholine receptors in rat hippocampus. Neuroscience 142, 187-201 (2006).
107. Prasanth K V, Spector D L (2007) Eukaryotic regulatory RNAs: an answer to the 'genome complexity' conundrum GENES & DEVELOPMENT 21: 11-42.
108. Ritz M C, Lamb R J, Goldberg S R, Kuhar M J. (1987) Cocaine receptors on dopamine transporters are related to self-administration of cocaine. Science. 237: 1219-23
109. Robledo R F, Rajan L, Li X, Lufkin T. (2002) The Dlx5 and Dlx6 homeobox genes are essential for craniofacial, axial, and appendicular skeletal development. Genes and Development 16: 1089-1101.
110. Role of dopamine D2-like receptors in cocaine self-administration: studies with D2 receptor mutant mice and novel D2 receptor antagonists. J Neurosci. 22(7):2977-88 (2002).
111. Sabarinadh C, Subramanian S, Tripathi A, Mishra R K 2004. Extreme conservation of noncoding DNA near HoxD complex of vertebrates. BMC Genomics 5: 75.
112. Saccone S F, Hinrichs A L, Saccone N L, Chase G A, Konvicka K, Madden P A, Breslau N, Johnson E O, Hatsukami D, Pomerleau O, Swan G E, Goate A M, Rutter J, Bertelsen S, Fox L, Fugman D, Martin N G, Montgomery G W, Wang J C, Ballinger D G, Rice J P, Bierut L J Cholinergic nicotinic receptor genes implicated in a nicotine dependence association study targeting 348 candidate genes with 3713 SNPs. Hum Mol Genet. 2007 Jan. 1:16(1):36-49. Epub 2006 Nov. 29.
113. Sanchez-Elsner T, Gou D, Kremmer E, Sauer F. (2006) Noncoding RNAs of trithorax response elements recruit *Drosophila* Ash1 to Ultrabithorax. Science 311:1118-23.
114. Sandelin A, Bailey P, Bruce S, Engstrom P G, Klos J M, Wasserman W W, Ericson J, Lenhard B. 2004. Arrays of ultraconserved non-coding regions span the loci of key developmental genes in vertebrate genomes. BMC Genomics 5: 99.
115. Santini S., Boore J. L., Meyer A 2003. Evolutionary conservation of regulatory elements in vertebrate Hox gene clusters. Genome Res. 13: 1111-1122.
116. Sasaki, H., Hui, C. C., Nakafuku, M., Kondoh, H. (1997) A binding site for Gli proteins is essential for the HNF-3b floor plate enhancer activity in transgenics and can respond to Shh in vitro. Development 124, 1313-1322.
117. Schaeren-Wiemers, N. and Gerfin-Moser, A (1993) A single protocol to detect transcripts of various types and expression levels in neural tissue and cultured cells; in situ hybridization using digoxigenin-labeled cRNA probes. Histochemistry 100, 431-440
118. Schmidt, J. V., Levorse, J. M. & Tilghman, S. M. (1999) Enhancer competition between H19 and Ig12 does not mediate their imprinting. Proc. Natl Acad. Sci. USA 96, 9733-9738.
119. Schule, B., Li, H. H., Fisch-Kohl, C., Purmann, C. & Francke, U. DLX5 and DLX6 expression is biallelic and not modulated by MeCP2 deficiency. Am. J. Hum. Genet. 81, 492-506 (2007).
120. Shamovsky, I. & Nudler, E. Gene control by large noncoding RNAs. Sci. STKE 2006, pe40 (2006).
121. Sleutels, F., Zwart, R., Barlow, D. P. (2002) The non-coding Air RNA is required for silencing autosomal imprinted genes. Nature 415, 810-813.
122. Snyder E. Y., Deitcher, D. L., Walsh, C., Arnold-Aldea, S., Hartwieg, E A, Cepko, C. L. (1992). Mutipotential neural cell lines can engraft and participate in development of mouse cerebellum. Cell 68, 33-51.
123. Soriano P. (1999) Generalized lacZ expression with the ROSA26 Cre reporter strain. Nat. Genet. 21: 70-71.
124. Stuhmer T, Anderson S A, Ekker M, Rubenstein J L. 2002. Ectopic expression of the Dlx genes induces glutamic acid decarboxylase and Dlx expression. Development. 129:245-52
125. Sui, G., Soohoo, C., Ajar el, B., Gay, F., Shi, Y. and Forrester, W. C. (2002) A DNA vector based RNAi technology to suppress gene expression in mammalian cells. Proc. Natl. Acad. Sci. USA 99, 5515-5520.
126. Sussel, L., Marin, O., Kimura, S., Rubenstein, J. L. (1999) Loss of Nkx2.1 homeobox gene function results in a ventral to dorsal molecular respecification within the basal telencephalon: evidence for a transformation of the pallidum into the striatum. Development 126, 3359-3370.
127. Sutherland, H F, Wadey, R., McKie J. M., Taylor C., Atif U., Johnstone K A, et. al. (1996) Identification of a novel transcript disrupted by a balanced translocation associated with DiGeorge Syndrome. Am. J. Hum. Genet. 59: 23-31.
128. Szucsik, J. C., Witte, D. P., Li, H., Pixley, S K, Small, K. M. and Potter, S. S. (1997) Altered forebrain and hindbrain development in mice mutant for the Gsh-2 homeobox gene. Dev. Biol. 191, 230-242.
129. Thomson, A. M., J. T., Rogers, Walker, C. E., Staton, J. M., Leedman, P. J. (1999) Optimized RNA Gel-shift and UV cross-linking assays for characterization of cytoplasmic RNA-Protein interactions. Biotechniques 27: 1032-1039.
130. Torreson, H., Potter, S. S., Campbell, K. (2000) Genetic control of dorsal-ventral identity in the telencephalon: opposing roles of Gsh2 and Pax6. Development 127, 4361-4371.
131. Trantham-Davidson H, Neely L C, Lavin A, Seamans J K. (2004) Mechanisms underlying differential D1 versus D2 dopamine receptor regulation of inhibition in prefrontal cortex. J Neurosci. 24:10652-9.
132. Volkow N D, Fowler J S, Wang G J, Hitzemann R, Logan J, Schlyer D J, Dewey S L, Wolf A P (1993) Decreased dopamine D2 receptor availability is associated with reduced frontal metabolism in cocaine abusers. Synapse 14(2):169-77.
133. Washietl S, Hofacker I L, Lukasser M, Huttenhofer A, Stadler P F. (2005) Mapping of conserved RNA secondary structures predicts thousands of functional noncoding RNAs in the human genome. Nat Biotechnol. 23:1383-90.
134. Wichterle, H., Turnbull, D. H., Nery, S., Fishell, G., and Alvarez-Buylla, A. (2001). In utero fate mapping reveals distinct migratory pathways and fates of neurons born in the mammalian basal forebrain. Development 128, 3759-3771.

135. Woloshin, P., K. Song, C. Degnin, A. M. Killary, D. J. Goldhamer, D. Sassoon, and M. J. Thayer. 1995. MSX1 inhibits MyoD expression in fibroblast 3×10T1/2 cell hybrids. Cell 82:611-620.
136. Woolfe A, Goodson M, Goode D K, Snell P, McEwen G K, Vavouri T, Smith S F, North P, Callaway H, Kelly K, Walter K, Abnizova I, Gilks W, Edwards Y J, Cooke J E, Elgar G. 2005. Highly conserved non-coding sequences are associated with vertebrate development. PLoS Biol. 3(1):e7.
137. Wutz, A. et al. (2001) Non-imprinted Igf2r expression decreases growth and rescues the Tme mutation in mice. Development 128, 1881-1887.
138. Xu, C., Cui, C. & Alkon, D. L. Age-dependent enhancement of inhibitory synaptic transmission in CA1 pyramidal neurons via GluR5 kainate receptors. Hippocampus (2009).
139. Yan, H., Yuan, W., Veiculescu, V. E., Vogel stein, B. & Kinzler, K W. Allelic variation in human gene expression. Science 297, 1143 (2002).
140. Yang, Z., Zhu, Q., Luo, K., Zhou, Q. (2001) The 7S K small nuclear RNA inhibits the CDK9/cyclin T1 kinase to control transcription. Nature 414, 317-322.
141. Yelin, R. et al. Widespread occurrence of antisense transcription in the human genome. Nat. Biotechnol. 21, 379-386 (2003).
142. Yun, K., Potter, S., Rubenstein, J. L. (2001) Gsh2 and Pax6 play complementary roles in dorsal ventral patterning of the mammalian telencephalon. Development 128, 193-205.
143. Zerucha, T. et al. A highly conserved enhancer in the Dlx5/Dlx6 intergenic region is the site of cross-regulatory interactions between Dlx genes in the embryonic forebrain. J. Neurosci. 20, 709-721 (2000).
144. Zhang H. Hu G. Wang H. Sciavolino P. Her N. Shen M M. Abate-Shen C. Heterodimerization of Msx and Dlx homeoproteins results in functional antagonism. (1997) Molecular & Cellular Biology. 17:2920-32.
145. Zhou, Q. P. et al. roentncencn of a direct Dlx homeodomain target in the developing mouse forebrain and retina by optimization of chromatin immunoprecipitation. Nucleic Acids Res. 32, 884-892 (2004).
146. Zwart, R., Sleutels, F., Wutz, A., Schinkel, A. H. & Barlow, D. P. (2001) Bidirectional action of the Igf2r imprint control element on upstream and downstream imprinted genes. Genes Dev. 15, 2361-2366.

The invention claimed is:

1. A transgenic mouse characterized by having reduced expression of a functional non-coding RNA Evf1, wherein the reduced expression is achieved by the introduction of a recombinant nucleic acid construct comprising an Evf1 sequence having a transcription stop sequence inserted into the Evf1 sequence, wherein the transgenic mouse is homozygous for the insertion, and wherein the transgenic mouse exhibits abnormal development of GABAergic interneurons, an altered dopamine response in the brain cortex or an altered cocaine response.

2. The transgenic mouse of claim 1, wherein the transcription stop sequence comprises a triple polyA sequence.

3. The transgenic mouse of claim 1, wherein the transgenic mouse exhibiting the abnormal development of GABAergic interneurons has decreased total GABAergic interneuron numbers in the prefrontal cortex relative to a wild type mouse.

4. The transgenic mouse of claim 1, wherein the transgenic mouse has reduced expression of the functional non-coding RNA Evf1 in brain tissue.

5. The transgenic mouse of claim 1, wherein the transgenic mouse has reduced expression of the functional non-coding RNA Evf1 in a prefrontal cortex.

6. A transgenic mouse characterized by having reduced expression of a functional non-coding RNA Evf1, wherein the reduced expression is achieved by the introduction of a recombinant nucleic acid construct comprising an Evf1 sequence having a transcription stop sequence inserted into the Evf1 sequence, wherein the transgenic mouse is homozygous for the insertion, and wherein the transgenic mouse has an increased number of neurons expressing dopamine 2 receptors relative to a wild type mouse or a decreased number of neurons expressing prodynorphin relative to a wild type mouse.

7. The transgenic mouse of claim 1, wherein the reduced expression of the functional non-coding RNA Evf1 is achieved by the introduction of a recombinant nucleic acid construct comprising an Evf sequence having a transcription stop sequence inserted in exon 3 of the Evf sequence.

8. The transgenic mouse of claim 7, wherein the recombinant nucleic acid construct comprises SEQ ID NO: 50.

9. The transgenic mouse of claim 1, wherein the mouse has reduced expression of a functional non-coding RNA Evf2.

10. The transgenic mouse of claim 9, wherein the reduced expression is achieved by the introduction of a recombinant nucleic acid construct comprising an Evf sequence having a transcription stop sequence inserted in exon 1 of the Evf sequence.

11. The transgenic mouse of claim 6, wherein the transcription stop sequence comprises a triple polyA sequence.

12. The transgenic mouse of claim 6, wherein the transgenic mouse has reduced expression of the functional non-coding RNA Evf1 in brain tissue.

13. The transgenic mouse of claim 6, wherein the transgenic mouse has reduced expression of the functional non-coding RNA Evf1 in a prefrontal cortex.

14. The transgenic mouse of claim 6, wherein the reduced expression of the functional non-coding RNA Evf1 is achieved by the introduction of a recombinant nucleic acid construct comprising an Evf sequence having a transcription stop sequence inserted in exon 3 of the Evf sequence.

15. The transgenic mouse of claim 14, wherein the recombinant nucleic acid construct comprises SEQ ID NO: 50.

16. The transgenic mouse of claim 6, wherein the mouse has reduced expression of a functional non-coding RNA Evf2.

17. The transgenic mouse of claim 16, wherein the reduced expression is achieved by the introduction of a recombinant nucleic acid construct comprising an Evf sequence having a transcription stop sequence inserted in exon 1 of the Evf sequence.

* * * * *

```
SEQUENCE LISTING

<160> NUMBER OF SEQ ID NOS: 54

<210> SEQ ID NO 1
<211> LENGTH: 35
<212> TYPE: DNA
<213> ORGANISM: Artificial Sequence
<220> FEATURE:
<223> OTHER INFORMATION: Evf2 mutant flanking sequence
<220> FEATURE:
<221> NAME/KEY: misc_feature
<222> LOCATION: (20)..(21)
<223> OTHER INFORMATION: Triple poly-A sequence

<400> SEQUENCE: 1
tttctagacc ctgatcattg cttaagagat attca                              35

<210> SEQ ID NO 2
<211> LENGTH: 34
<212> TYPE: DNA
<213> ORGANISM: Artificial Sequence
<220> FEATURE:
<223> OTHER INFORMATION: primer for retrieval homology arm; CLa I

<400> SEQUENCE: 2
gatgcgaatc gatcggctta ggcctccagg tttc                               34

<210> SEQ ID NO 3
<211> LENGTH: 33
<212> TYPE: DNA
<213> ORGANISM: Artificial Sequence
<220> FEATURE:
<223> OTHER INFORMATION: primer for retrieval homology arm; HindIII

<400> SEQUENCE: 3
aaaccctaag cttgactagc gtggcccaaa ggt                                33

<210> SEQ ID NO 4
<211> LENGTH: 39
<212> TYPE: DNA
<213> ORGANISM: Artificial Sequence
<220> FEATURE:
<223> OTHER INFORMATION: primer for retrieval homology arm;
```

HindIII(star)

<400> SEQUENCE: 4
gatgcgaaag cttctgtcag tgccaaaatg aaggacat                    39

<210> SEQ ID NO 5
<211> LENGTH: 35
<212> TYPE: DNA
<213> ORGANISM: Artificial Sequence
<220> FEATURE:
<223> OTHER INFORMATION: primer for retrieval homology arm; NheI

<400> SEQUENCE: 5
gatgcgagct agcggggttg ggacctggtt ttagg                       35

<210> SEQ ID NO 6
<211> LENGTH: 37
<212> TYPE: DNA
<213> ORGANISM: Artificial Sequence
<220> FEATURE:
<223> OTHER INFORMATION: primer for targeting arms; Sac II

<400> SEQUENCE: 6
ttagttccgc ggcctggtcc tttcttcgtc tcaagtc                     37

<210> SEQ ID NO 7
<211> LENGTH: 45
<212> TYPE: DNA
<213> ORGANISM: Artificial Sequence
<220> FEATURE:
<223> OTHER INFORMATION: primer for targeting arms; Not1

<400> SEQUENCE: 7
atttgcggcc gccttaagag atattcaccg gggtaagttt ttatt            45

<210> SEQ ID NO 8
<211> LENGTH: 43
<212> TYPE: DNA
<213> ORGANISM: Artificial Sequence
<220> FEATURE:
<223> OTHER INFORMATION: primer for targeting arms; Cla1

<400> SEQUENCE: 8
gattttatcg atcaatgatc agggtctaga aatctatact gag              43

<210> SEQ ID NO 9
<211> LENGTH: 38
<212> TYPE: DNA
<213> ORGANISM: Artificial Sequence
<220> FEATURE:
<223> OTHER INFORMATION: primer for targeting arms; Kpn

<400> SEQUENCE: 9
gattttggta ccttcagggt ttgatttgat cgctactg                    38

<210> SEQ ID NO 10
<211> LENGTH: 21
<212> TYPE: DNA
<213> ORGANISM: Artificial Sequence
<220> FEATURE:
<223> OTHER INFORMATION: 5' ES Southern probe mEvf5'.1

<400> SEQUENCE: 10
tggtgaagct ggaggaagga c                                      21

```
<210> SEQ ID NO 11
<211> LENGTH: 24
<212> TYPE: DNA
<213> ORGANISM: Artificial Sequence
<220> FEATURE:
<223> OTHER INFORMATION: 5' ES Southern probe mEvf5'.2

<400> SEQUENCE: 11
cacactgact tctgaacacc cctg                                          24

<210> SEQ ID NO 12
<211> LENGTH: 26
<212> TYPE: DNA
<213> ORGANISM: Artificial Sequence
<220> FEATURE:
<223> OTHER INFORMATION: 3' Southern probe mEvD'.1

<400> SEQUENCE: 12
ggggtgaagg atggtgatta aagagc                                        26

<210> SEQ ID NO 13
<211> LENGTH: 20
<212> TYPE: DNA
<213> ORGANISM: Artificial Sequence
<220> FEATURE:
<223> OTHER INFORMATION: 3' Southern probe mEvf3'.1

<400> SEQUENCE: 13
gtggctggct gtcctttggt                                               20

<210> SEQ ID NO 14
<211> LENGTH: 24
<212> TYPE: DNA
<213> ORGANISM: Artificial Sequence
<220> FEATURE:
<223> OTHER INFORMATION: primer; Evf2-F

<400> SEQUENCE: 14
ctccctccgc tcagtataga tttc                                          24

<210> SEQ ID NO 15
<211> LENGTH: 21
<212> TYPE: DNA
<213> ORGANISM: Artificial Sequence
<220> FEATURE:
<223> OTHER INFORMATION: primer; Evf2-R

<400> SEQUENCE: 15
cctccccggt gaatatctct t                                             21

<210> SEQ ID NO 16
<211> LENGTH: 19
<212> TYPE: DNA
<213> ORGANISM: Artificial Sequence
<220> FEATURE:
<223> OTHER INFORMATION: primer; Dlx2-F

<400> SEQUENCE: 16
ccctacggca ccagttcgt                                                19

<210> SEQ ID NO 17
<211> LENGTH: 20
<212> TYPE: DNA
<213> ORGANISM: Artificial Sequence
<220> FEATURE:
<223> OTHER INFORMATION: primer; Dlx2-R
```

```
<400> SEQUENCE: 17
tcggatttca ggctcaaggt                                               20

<210> SEQ ID NO 18
<211> LENGTH: 24
<212> TYPE: DNA
<213> ORGANISM: Artificial Sequence
<220> FEATURE:
<223> OTHER INFORMATION: primer; Nrp2-F

<400> SEQUENCE: 18
acttttcagg acacgaagtg agaa                                          24

<210> SEQ ID NO 19
<211> LENGTH: 21
<212> TYPE: DNA
<213> ORGANISM: Artificial Sequence
<220> FEATURE:
<223> OTHER INFORMATION: primer; Nrp2-R

<400> SEQUENCE: 19
gccagcatct ttggaattca g                                             21

<210> SEQ ID NO 20
<211> LENGTH: 19
<212> TYPE: DNA
<213> ORGANISM: Artificial Sequence
<220> FEATURE:
<223> OTHER INFORMATION: primer; Gad67-F

<400> SEQUENCE: 20
actccttcgc ctgcaacct                                                19

<210> SEQ ID NO 21
<211> LENGTH: 22
<212> TYPE: DNA
<213> ORGANISM: Artificial Sequence
<220> FEATURE:
<223> OTHER INFORMATION: primer; Gad67-R

<400> SEQUENCE: 21
cgccacacca agtatcatac gt                                            22

<210> SEQ ID NO 22
<211> LENGTH: 19
<212> TYPE: DNA
<213> ORGANISM: Artificial Sequence
<220> FEATURE:
<223> OTHER INFORMATION: primer; Beta-actin-F

<400> SEQUENCE: 22
gcgagcacag cttctttgc                                                19

<210> SEQ ID NO 23
<211> LENGTH: 19
<212> TYPE: DNA
<213> ORGANISM: Artificial Sequence
<220> FEATURE:
<223> OTHER INFORMATION: primer; Beta-actin-R

<400> SEQUENCE: 23
tcgtcatcca tggcgaact                                                19

<210> SEQ ID NO 24
<211> LENGTH: 23
```

```
<212> TYPE: DNA
<213> ORGANISM: Artificial Sequence
<220> FEATURE:
<223> OTHER INFORMATION: primer for taqMan PCT; Dlx5-probe

<400> SEQUENCE: 24
caagcatccg atccggcgac ttc                                            23

<210> SEQ ID NO 25
<211> LENGTH: 27
<212> TYPE: DNA
<213> ORGANISM: Artificial Sequence
<220> FEATURE:
<223> OTHER INFORMATION: primer for taqMan PCT; Dlx5-F

<400> SEQUENCE: 25
tatgacagga gtgtttgaca gaagagt                                        27

<210> SEQ ID NO 26
<211> LENGTH: 18
<212> TYPE: DNA
<213> ORGANISM: Artificial Sequence
<220> FEATURE:
<223> OTHER INFORMATION: primer for taqMan PCT; Dlx5-R

<400> SEQUENCE: 26
acgtcgggaa cggagctt                                                  18

<210> SEQ ID NO 27
<211> LENGTH: 28
<212> TYPE: DNA
<213> ORGANISM: Artificial Sequence
<220> FEATURE:
<223> OTHER INFORMATION: primer for taqMan PCT; Dlx6-probe

<400> SEQUENCE: 27
aacgcctacg gagcttctga aggagaca                                       28

<210> SEQ ID NO 28
<211> LENGTH: 26
<212> TYPE: DNA
<213> ORGANISM: Artificial Sequence
<220> FEATURE:
<223> OTHER INFORMATION: primer for taqMan PCT; Dlx6-F

<400> SEQUENCE: 28
gagaccacag atgatgtgac ttctct                                         26

<210> SEQ ID NO 29
<211> LENGTH: 22
<212> TYPE: DNA
<213> ORGANISM: Artificial Sequence
<220> FEATURE:
<223> OTHER INFORMATION: primer for taqMan PCT; Dlx6-R

<400> SEQUENCE: 29
ctgccatgtt tgtgcagatt ct                                             22

<210> SEQ ID NO 30
<211> LENGTH: 27
<212> TYPE: DNA
<213> ORGANISM: Artificial Sequence
<220> FEATURE:
<223> OTHER INFORMATION: primer for taqMan PCT; Evf1-probe

<400> SEQUENCE: 30
```
agagctatgc gactgtaggc aagccat          27

<210> SEQ ID NO 31
<211> LENGTH: 24
<212> TYPE: DNA
<213> ORGANISM: Artificial Sequence
<220> FEATURE:
<223> OTHER INFORMATION: primer for taqMan PCT; Evf1-F

<400> SEQUENCE: 31
gcatggaaac tttgatacct tggt             24

<210> SEQ ID NO 32
<211> LENGTH: 27
<212> TYPE: DNA
<213> ORGANISM: Artificial Sequence
<220> FEATURE:
<223> OTHER INFORMATION: primer for taqMan PCT; Evf1-R

<400> SEQUENCE: 32
gcctttcaga actagaaggg atttaaa          27

<210> SEQ ID NO 33
<211> LENGTH: 22
<212> TYPE: DNA
<213> ORGANISM: Artificial Sequence
<220> FEATURE:
<223> OTHER INFORMATION: primer for taqMan PCT; Beta actin probe

<400> SEQUENCE: 33
caacgagcgg ttccgatgcc ct               22

<210> SEQ ID NO 34
<211> LENGTH: 21
<212> TYPE: DNA
<213> ORGANISM: Artificial Sequence
<220> FEATURE:
<223> OTHER INFORMATION: primer for taqMan PCT; Beta-actin-F

<400> SEQUENCE: 34
acggccaggt catcactatt g                21

<210> SEQ ID NO 35
<211> LENGTH: 22
<212> TYPE: DNA
<213> ORGANISM: Artificial Sequence
<220> FEATURE:
<223> OTHER INFORMATION: primer for taqMan PCT; Beta-actin-R

<400> SEQUENCE: 35
caagaaggaa ggctggaaaa ga               22

<210> SEQ ID NO 36
<211> LENGTH: 20
<212> TYPE: DNA
<213> ORGANISM: Artificial Sequence
<220> FEATURE:
<223> OTHER INFORMATION: primer for quantitative PCT; I-F

<400> SEQUENCE: 36
tatgaaaagc ccaggattgc                  20

<210> SEQ ID NO 37
<211> LENGTH: 20
<212> TYPE: DNA
<213> ORGANISM: Artificial Sequence

```
<220> FEATURE:
<223> OTHER INFORMATION: primer for quantitative PCT; I-R

<400> SEQUENCE: 37
tgtcccagct tcctatcacc                                                   20

<210> SEQ ID NO 38
<211> LENGTH: 20
<212> TYPE: DNA
<213> ORGANISM: Artificial Sequence
<220> FEATURE:
<223> OTHER INFORMATION: primer for quantitative PCT; 2-F

<400> SEQUENCE: 38
tggtttgaaa gagggaatg                                                    20

<210> SEQ ID NO 39
<211> LENGTH: 21
<212> TYPE: DNA
<213> ORGANISM: Artificial Sequence
<220> FEATURE:
<223> OTHER INFORMATION: primer for quantitative PCT; 2-R

<400> SEQUENCE: 39
agagcgctta ttctgaaacc a                                                 21

<210> SEQ ID NO 40
<211> LENGTH: 23
<212> TYPE: DNA
<213> ORGANISM: Artificial Sequence
<220> FEATURE:
<223> OTHER INFORMATION: primer for quantitative PCT; 3-F

<400> SEQUENCE: 40
cccaggatca attctgaaca aag                                               23

<210> SEQ ID NO 41
<211> LENGTH: 21
<212> TYPE: DNA
<213> ORGANISM: Artificial Sequence
<220> FEATURE:
<223> OTHER INFORMATION: primer for quantitative PCT; 3-R

<400> SEQUENCE: 41
tccccaatgt ctgcttcaaa t                                                 21

<210> SEQ ID NO 42
<211> LENGTH: 20
<212> TYPE: DNA
<213> ORGANISM: Artificial Sequence
<220> FEATURE:
<223> OTHER INFORMATION: primer for quantitative PCT; 4-F

<400> SEQUENCE: 42
tggattccct gaactccaag                                                   20

<210> SEQ ID NO 43
<211> LENGTH: 20
<212> TYPE: DNA
<213> ORGANISM: Artificial Sequence
<220> FEATURE:
<223> OTHER INFORMATION: primer for quantitative PCT; 4-R

<400> SEQUENCE: 43
agggcttggg aactcaaact                                                   20
```

```
<210> SEQ ID NO 44
<211> LENGTH: 21
<212> TYPE: DNA
<213> ORGANISM: Artificial Sequence
<220> FEATURE:
<223> OTHER INFORMATION: primer for quantitative PCT; 5-F

<400> SEQUENCE: 44
ggcgcatctt tgcaaattac a                                            21

<210> SEQ ID NO 45
<211> LENGTH: 21
<212> TYPE: DNA
<213> ORGANISM: Artificial Sequence
<220> FEATURE:
<223> OTHER INFORMATION: primer for quantitative PCT; 5-R

<400> SEQUENCE: 45
gcaggctgga ttaggatgct a                                            21

<210> SEQ ID NO 46
<211> LENGTH: 20
<212> TYPE: DNA
<213> ORGANISM: Artificial Sequence
<220> FEATURE:
<223> OTHER INFORMATION: primer for quantitative PCT; 6-F

<400> SEQUENCE: 46
tcgaaagtat tgcgtggatg                                              20

<210> SEQ ID NO 47
<211> LENGTH: 20
<212> TYPE: DNA
<213> ORGANISM: Artificial Sequence
<220> FEATURE:
<223> OTHER INFORMATION: primer for quantitative PCT; 6-R

<400> SEQUENCE: 47
gtgtgtacca agcgcatgtc                                              20

<210> SEQ ID NO 48
<211> LENGTH: 20
<212> TYPE: DNA
<213> ORGANISM: Artificial Sequence
<220> FEATURE:
<223> OTHER INFORMATION: primer for quantitative PCT; 7-F

<400> SEQUENCE: 48
ggcgtgtcag cacctgattt                                              20

<210> SEQ ID NO 49
<211> LENGTH: 20
<212> TYPE: DNA
<213> ORGANISM: Artificial Sequence
<220> FEATURE:
<223> OTHER INFORMATION: primer for quantitative PCT; 7-R

<400> SEQUENCE: 49
gccaagtcac tgcccatctc                                              20

<210> SEQ ID NO 50
<211> LENGTH: 30
<212> TYPE: DNA
<213> ORGANISM: Artificial Sequence
<220> FEATURE:
<223> OTHER INFORMATION: Evf1 mutant flanking sequence
```

```
<220> FEATURE:
<221> NAME/KEY: misc_feature
<222> LOCATION: (15)..(16)
<223> OTHER INFORMATION: Triple poly-A sequence

<400> SEQUENCE: 50
tcaaagatgg actggggaaa gacattaagt                                     30

<210> SEQ ID NO 51
<211> LENGTH: 385
<212> TYPE: RNA
<213> ORGANISM: Mus musculus

<400> SEQUENCE: 51
agacagagcc ucugcccuga gacucagaga aacgcucucc ugugccuccc uccgcucagu    60
auagauuucu agacccugau cauugcuuaa gagauauuca ccggggaggu ccuacgucuc   120
ugcaauuugu guaugaauaa cagaauaauu ucccucuuuu guuucgccuu uccuguuccu   180
gaaucuaaau aaagauggcu uuuuaguauu aaaaguggaa gaaaauuaca gguaauuauc   240
uuugacggua aaaacgcugu aaucagcggg cuacaugaaa aauuacucua auuauggcug   300
cauuuaagag aauggaaaaa aaccuucuug uggauaaaaa ccuuaaauug uccccaaugu   360
cugcuucaaa uuggauggca cugca                                        385

<210> SEQ ID NO 52
<211> LENGTH: 3456
<212> TYPE: RNA
<213> ORGANISM: Mus musculus

<400> SEQUENCE: 52
agacagagcc ucugcccuga gacucagaga aacgcucucc ugugccuccc uccgcucagu    60
auagauuucu agacccugau cauugcuuaa gagauauuca ccggggaggu ccuacgucuc   120
ugcaauuugu guaugaauaa cagaauaauu ucccucuuuu guuucgccuu uccuguuccu   180
gaaucuaaau aaagauggcu uuuuaguauu aaaaguggaa gaaaauuaca gguaauuauc   240
uuugacggua aaaacgcugu aaucagcggg cuacaugaaa aauuacucua auuauggcug   300
cauuuaagag aauggaaaaa aaccuucuug uggauaaaaa ccuuaaauug uccccaaugu   360
cugcuucaaa uuggauggca cugcagcugg aggcuuuguu cagaauugau ccuggggagc   420
uacgaaccca aguuucaca guaggaaggg ggaaaaaaga aaagaaaaca uuuuccuaa    480 uguaacaaug cgaaugcuag aaaaugacaa gacugaucgg uuuuaaacca uucugaagac   540
ugacugagcg uggaaguugc ucaacaaaaa agggaacggg gauauucaga accagagaga   600
aaccuacgcc cagaagaaca ugucccugga uugcuuuccc acugcugugg agugucuuga   660
acacugguuc cuggacacca acuucaagaa gacuucaugg auggcugucc agucuuauga   720
gccacaguuu ccccucuaca uuuucuucac uccagcgagg cucuuaucag ggucagauca   780
gagaugaacc agcuggacga cagauuggag cgcugaccuc uuagagugcu aacagugaac   840
aguguggggu cagaucuaua gaaagauaau aauaagaaaa cacccuauau gcaagggaga   900
gggaugguuc auaauuucuu aaagauugaa aucaaggaac aaucaaaaua uagaagaaug   960
uggacguguu uugcugcagg acuucuguuu ugucccauu ggaauaugua uuaugguauu   1020
ccuguuggau caggacucag gggcaaggcu aagcauucca guggucccuc uacuuagcuc   1080
uuguccuuuc guaagaaaca ccaacucauu agcucuauaa uuacuucucu guacuguaga   1140
ucugcauucu ugaucugaga gauauuggca augacacucu guaugauaa agcucaauga   1200
```

```
uaagaguacu ucaaacccccc uugaacuuuu uguuuauaca ucaaguggug acauugugua    1260
uugagcuaau uagaucaaug gagucacagg gugauacuga acucuuuuaa aauauuuggc    1320
ugaaacauga cauuguaguu auuuguagaa gagaacauua uggaauauga aaaacaucac    1380
agaacacaga acuagcagca gaaacuagca gcagguagac auuuuuccuu uuccauagag    1440
cuuucaacca aaugucucug uagaaaauag uggcuaucgu guauauauau agccacauag    1500
auguccuuga guguacccug uagcagugg gagaguuccu acugccacag ucauggccau    1560
ggcuauguuc ucuaagccua cauuuuauaa acacucugug aaucuugacu acuuucuuu    1620 agcaagcauu gcaaaguccu gggaugucag agaagugccu gggguuggca ggguuucuag    1680
agaggaaauu guuaaaugau uugaaccaga aaacaaacag gggauggggu ucagaaccaa    1740
caauuaccuc uauucuaugu aggaaaccac aacaugaaau augcggggca uggaaacuuu    1800
gauaccuugg uuuuucauuc uuuuuaaaaa uuaauacuaa agagcuaugc gacuguaggc    1860
aagccauuuc ccauccccug ugaauaucuc ccagaugacu uuaaauccuu ucuaguucug    1920
aaaggcuuuu aacaucaggg cccaggcucc aguggccagu ucaaaauac ccucccuuuu    1980 gauguuaggu uacauaaaca uuguucuuuu uagggaggg ucucuuuuau caacuuuuaa    2040
aaacacacau cagguucucu gguauuaaaa agaugccauc ucgagucccc cuacuaucug    2100
ugcugccugc cuuccuccu guucuuuccu uauucccauc ccauugaac uugugcuaug    2160 caguaugcau caggaugug uuagcuuugg ggauacauga uagauaaacu ggacacacag    2220
ggucuuccca uucucuucug gaauuuucuu uggagggagc cucuuguauc uagacagacc    2280
gugcuguggu accccagagg uaaccaccua caggcuucac ucugccuaag caauuuugcu    2340
gugcacuaag auacacauuc aaguaacuuu agauuaccac aauaacuuuc uccagguaug    2400
aggaaaagag auaauuuacu ucugagaugu guauaggaua gcccuccauc cugggaagaa    2460
cagugacuac ucccugcauc ccgaccuugc ccagggaaag cuaauguuuc ucuguguuau    2520
cccugugacu ugccacuucu uuaaaaagga augggcaaac aauaaacaga caaaaauguu    2580
gucugaccuc auuggaaauc cuuuuaagaa uuaauccuuu cuaucuccuu cauuaucaac    2640
aaaucuauug aauacuuauc ucugagucca gggcauauuu uauaauacau aaaacaaugg    2700
aauuucaaaa uuggagcacu gacauacaau auugguuuug aguauuuuua uuauagggaa    2760
ugacuuuaga cauugcaauu uaugacuuaa cugauaaaau ggaugacucu ugacuuucaa    2820
uuuucauuuu caguucaguc gaggaauagc uuccuccagg uaaugucuau acuuccuau    2880 gacuaagggc ucuaacuauc ucuguugcuu ucuuuaugu aggcauaugu uaguauuuau    2940
uuucuauaug acaaauguau uaagaaagc augaaauuaa ugagauaaac uuuucagaua    3000
ggaguuuaga aaaucaaggg gccaagauaa auaaaugaaa aaucaacuua aauaauuaac    3060
auauuccaga uauauuggaa uaaauguuua uuguacccuu ugguuuugu cuggguuau    3120 uuuuucuua ucucacugau uuuuuuucu uuccuuuuua gcuuuuugu cuuuuugau    3180 uuuguuguu gcguuucucc uuuuuuuuuu ucuuguugau guuguugu uguuguuug    3240 uuuguuuuuu gagaaagaac agaagguugg uuggauaggg agguggggaa gaucuaucug    3300
gauggaguug ggaggaggga aaauacacga ucaaaauaua uuuugugaug ggcagggcau    3360 aguggauacau gucuuuaauc ucagcacucu ggaggcagag gcagguggau cucuaugaga    3420
uggaggcuag ccugauauac aaagugagac cagaac                                3456
```

<210> SEQ ID NO 53
<211> LENGTH: 117

```
<212> TYPE: RNA
<213> ORGANISM: Mus musculus

<400> SEQUENCE: 53
ggggaaagac auuaaguuug gagcagcuca gugcuacgga ucuagccucu cucccucggg      60
ucuccagacu cacuuggucc aagcugcgga gcagggacag cggagcucag gcggcca       117

<210> SEQ ID NO 54
<211> LENGTH: 3006
<212> TYPE: RNA
<213> ORGANISM: Mus musculus

<400> SEQUENCE: 54
ggggaaagac auuaaguuug gagcagcuca gugcuacgga ucuagccucu cucccucggg      60
ucuccagacu cacuuggucc aagcugcgga gcagggacag cggagcucag gcggccacgu     120
ucaggcccag ccaccacaga accagagaga aaccuacgcc cagaagaaca ugucccugga     180
uugcuuuccc acugcugugg agugucuuga cacugguccc cuggacacca acuucaagaa     240
gacuucaugg auggcugucc agucuuauga gccacaguuu ccccucuaca uuuucuucac     300
uccagcgagg cucuuaucag ggucagauca gagaugaacc agcugacga cagauuggag     360 cgcugaccuc uuagagugcu aacagugaac agugugggu cagaucuaua gaaagauaau      420
aauaagaaaa cacccuauau gcaagggaga gggauggeuuc auaauuucuu aaagauugaa    480
aucaaggaac aaucaaaaua uagaagaaug uggacugugu uugcugcagg acuucuguuu     540
ugucCCcauu ggaauaugua uuaugguauu ccuguuggau caggacucag gggcaaggcu     600
aagcauucca guggucCucc acuuagcuc uguccuuuc guaagaaaca ccaacucauu       660
agucucuaua uuacuucucu guacuguaga ucugcauucu ugaucugaga gauauuggca    720
augacacucu uguaugauaa agcucaauga uaagaguacu caaaccccc uugaacuuuu       780 uguuuauaca ucaagguguu acauuguua uugagcuaau uagaucaaug gagucacagg      840
gugauacuga acucuuuuaa aauauuuuggc ugaaacauga cauuguaguu auuuguagaa    900
gagaacauua uggaauauga aaaacaucac agaacacaga acuagcagca gaaacuagca     960
gcagguagac auuuuucccuu uuccauagag cuuucaacca aaugucucug uagaaaauag   1020
uggcuaucgu guauauauau agccacauag augccuuuga guguacccug uagucagugg    1080
gagaguuccu acugccacag ucauggccau ggcuauguuc ucuaagccua cauuuuauaa    1140
acacucugug aaucuugacu acuuuucuuu agcaagcauu gcaaagaccu gggauggucag   1200 agaagugccu gggguuggca ggguuucuag agaggaaauu guuaaaugau uugaaccaga    1260
aaacaaacag gggauggggu ucagaaccaa caauuaccuc uauucuaugu aggaaaccac    1320
aacaugaaau augcugggca uggaaacuuu gauaccuugg uuuucauuc uuuuuaaaaa    1380 uuaauacuaa agagcuaugc gacuguaggc aagccauuuc ccauccccug ugaauaucuc   1440
ccagaugacu uuuaaaucccu ucuaguucug aaaggcuuuu aacaucaggg cccaggcucc    1500
aguggccagu uucaaaauac ccucccuuuu gauguuaggu acauaaaca uuguucuuuu     1560 uuagggaggg ucucuuuuau caacuuuuaa aaacacacauu caagguucucu gguauuaaaa    1620 agaugccauc ucugagucCc cuacuauCug ugcugccugc cuuccuccuu gucuuuccuu     1680
uauucccauc ccuauugaac uugugcuaug caguaugcau cagguaugug uuagcuuugg    1740
ggauacauga uagauaaacu ggacacacag ggcuuccca uucucuuucu gaauuuucuu     1800
uggagggagc cucuuguauc uagacagacc gugcucuggu accccagagg uaaccaccua    1860
```

-continued

```
caggcuucac ucugccuaag caauuuugcu gugcacuaag auacacauuc aaguaacuuu    1920
agauuaccac aauaacuuuc uccagguaug aggaaaagag auaauuuacu ucugagaugu    1980
guauaggaua gcccuccauc cugggaagaa cagugacuac ucccugcauc ccgaccuugc    2040
ccagggaaag cuaauguuuc ucuguguuau cccugugacu ugccacuucu uuaaaaagga    2100
augggcaaac aauaaacaga caaaaauguu gucugaccuc auuggaaauc cuuuuaagaa    2160
uuaauccuuu cuaucuccuu cauuaucaac aaaucuauug aauacuuauc ucgagucca    2220 gggcauauuu uauaauacau aaaacaaugg aauuucaaaa uuggagcacu gacauacaau    2280
auugguuuug aguauuuuua uuauagggaa ugacuuuaga cauugcaauu uaugacuuaa    2340
cugauaaaau ggaugacucu ugacuuucaa uuuucauuuu caguucaguc gaggaauagc    2400
uuccuccagg uaaugucuau acuuuccuau gacuaagggc ucuaacuauc ucuguugcuu    2460
uucuuuaugu aggcauaugu uaguauuuau uuucuauaug acaaauguau uaaagaaagc    2520
augaaauuaa ugagauaaac uuuucagaua ggaguuuaga aaaucaaggg gccaagauaa    2580
auaaaugaaa aaucaacuua aauaauuaac auauuccaga uauauuggaa uaaauguuua    2640
uuguacccuu uugguuugu cuugggguuau uuuuuucuua ucucacugau uuuuuuucu     2700 uuccuuuuua gcuuuuugu cuuuuugau uuuuguugu gcguuucucc uuuuuuuuu      2760 ucuuguugau guuguuugu uguuuguug uuuguuuu gagaaagaac agaagguugg       2820
uuggauaggg aggugggaa gaucuaucug gauggaguug ggaggaggga aaauacacga     2880
ucaaaauaua uuuugugaug ggcagggcau agugguacau gucuuuaauc ucagcacucu    2940
ggaggcagag gcagguggau cucuaugaga uggaggcuag ccugauauac aaagugagac    3000
cagaac                                                              3006
```